(12) United States Patent
Fulton et al.

(10) Patent No.: US 8,865,642 B2
(45) Date of Patent: Oct. 21, 2014

(54) NATURAL PLANT PRODUCTS FOR CONTROL OF CANCER METASTASIS

(75) Inventors: Amy Fulton, Baltimore, MD (US); Namita Kundu, Columbia, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 13/635,095

(22) PCT Filed: Dec. 17, 2010

(86) PCT No.: PCT/US2010/061073
§ 371 (c)(1),
(2), (4) Date: Sep. 14, 2012

(87) PCT Pub. No.: WO2011/115651
PCT Pub. Date: Sep. 22, 2011

(65) Prior Publication Data
US 2013/0017225 A1    Jan. 17, 2013

Related U.S. Application Data

(60) Provisional application No. 61/314,210, filed on Mar. 16, 2010.

(51) Int. Cl.
| | | |
|---|---|---|
| *A61K 38/00* | (2006.01) | |
| *A61P 35/00* | (2006.01) | |
| *A61K 38/16* | (2006.01) | |
| *A61K 36/888* | (2006.01) | |
| *A61K 38/56* | (2006.01) | |

(52) U.S. Cl.
CPC ............. *A61K 36/888* (2013.01); *A61K 38/168* (2013.01); *A61K 38/56* (2013.01)
USPC .......................................... 514/1.1; 514/19.4

(58) Field of Classification Search
None
See application file for complete search history.

(56) References Cited

U.S. PATENT DOCUMENTS

| | | |
|---|---|---|
| 2001/0024664 A1* | 9/2001 | Obukowicz et al. .......... 424/725 |
| 2002/0132021 A1 | 9/2002 | Raskin et al. |
| 2004/0241137 A1 | 12/2004 | Segal et al. |
| 2009/0041803 A1 | 2/2009 | Yang et al. |

OTHER PUBLICATIONS

Bezerra et al., Plant Molecular Biology, 1995, 28: 137-144.*
Hirai et al., Jpn. J. Genet., 1993, 68: 229-236.*
Gura, Science, v278, 1997, pp. 1041-1042.*
Kaiser, Science, 2006, 313, 1370.*
Bodey et al, Expert Opinion Biological Therapy, 2001, 1(4): 603-17.*

* cited by examiner

*Primary Examiner* — Hong Sang
(74) *Attorney, Agent, or Firm* — Nevrivy Patent Law Group P.L.L.C.

(57) ABSTRACT

The invention provides compositions comprising soluble extracts or isolated polypeptides from the edible roots of the plant *Colocasia*, such as *Colocasia esculenta*, commonly known as Taro, and from *Xanthosoma*, such as *Xanthosoma sagittifolium*, commonly known as Malanga Blanca or Yautia. The compositions exhibit inhibitory effects on metastasis of cancer cells in particular breast and prostate cancer cells and have therapeutic pharmacological activity, Pharmaceutical compositions for the treatment of cancer by inhibiting metastasis which comprises an effective amount of the described extract or isolated polypeptide thereof and optionally a pharmaceutical acceptable carrier are described.

4 Claims, 28 Drawing Sheets

Taro Corm

```
              Peak-I:     LGTNYLLSGQTLNTDGHLKNGDFD  SEQ ID NO: 1
Tarin    ---MAXILLFLLPATLGLLIPR---SAVALGTNYLLSGQTLNTDGHLKNGDFDLVMQNDCNL  56
Lectin   ---MAXILLFLLPATLGLLIPR---SAVALGTNYLLSGQTLNTDGHLKNGDFDLVMQNDCNL  56
12kD SP  RHIPHGQASPLPPPGHPREPRSWSAVALGTNYLLSGQTLETEGHLKNGDF

NATURAL PLANT PRODUCTS FOR CONTROL OF CANCER METASTASIS

CROSS REFERENCE TO RELATED APPLICATIONS

This application is the U.S. National Stage under 35 U.S.C. §371 of International Application No.: PCT/US2010/061073, filed Dec. 17, 2010, which claims the benefit of U.S. Appl. No. 61/314,210, filed Mar. 16, 2010. The content of the aforesaid application is relied upon and incorporated by reference in its entirety.

STATEMENT OF FEDERALLY SPONSORED RESEARCH AND DEVELOPMENT

This invention was made with government support under Grant Number CA120278 awarded by the National Institutes of Health. The government has certain rights in the invention.

INCORPORATION-BY-REFERENCE OF MATERIAL SUBMITTED ELECTRONICALLY

Incorporated by reference in its entirety herein is a computer-readable sequence listing submitted concurrently herewith and identified as follows: One 11,072 Byte ASCII (Text) file named "sequence_0listing.txt," created on Apr. 16, 2014.

FIELD OF THE INVENTION

The invention generally relates to cancer treatment. In particular, the invention relates to methods for preventing or treating metastatic disease including breast and prostate cancer, using a composition extracted from natural edible plant roots including *Colocasia esculenta* and *Xanthosoma sagittifolium*.

BACKGROUND OF THE INVENTION

Breast cancer is the second leading cancer death in women in the United States. Breast cancer mortality is primarily due to the occurrence of metastatic disease. Approximately 182,460 women in the United States are expected to be diagnosed with invasive breast cancer this year. Nearly 40,480 women died from breast cancer during the previous year. Presently there are about two and half million breast cancer survivors in the United States. The chance of a women having invasive breast cancer sometime during her life is about 1 in 8. The chance of dying from breast cancer is about 1 in 35. Breast cancer mortality is primarily due to the occurrence of metastatic disease. Because of high breast cancer mortality and toxicity of many current therapies, the identification of more effective therapies with fewer side effects and that specifically target metastasis are urgently needed. Research over the last three decades has provided convincing evidence supporting the premise that diets rich in fruits and vegetables may be protective against the risk of different types of cancer. Dietary agents can prevent carcinogenesis by different mechanisms including enhanced detoxification of the carcinogenic intermediates, inducing apoptosis in cancer but not normal cells, perturbing cell cycle progression and inhibiting angiogenesis and metastasis. Laboratory studies have shown strong chemopreventive and possibly cancer chemotherapeutic effects of whole foods and bioactive food components against cancers of skin, lung, breast, colon, liver, stomach, prostate and other sites (Kelloff, G. J. Perspective on cancer chemoprevention research and drug development. Adv. Cancer Res. 78: 199-334, 2000; Liu, R. H. Health benefits of fruit and vegetables and from additive and synergistic combinations of phytochemicals. Am. J. Clin. Nutr. 78: 517s-520s, 2003; Surh, Y. J. Cancer chemoprevention with dietary phytochemicals. Nat. Rev. Cancer 3:768-780, 2003; Milner, J. A. Molecular targets for bioactive food components. J. Nutr. 134: 2492s-2498s, 2004; Davis, C. D. and Milner, J. A. Diet and cancer prevention. In: Temple, N. J., Wilson, T. and Jacobs D. R. editors. Nutritional health: Strategies for disease prevention. Totowa N.J.: Humana Press. pp 151-171, 2006). *Allium* vegetable-derived diallyl sulfide (DAS), diallyl disulfide (DADS) and diallyl trisulfide (DATS) have strong anti-cancer properties. DAS has been shown to inhibit aberrant crypt foci (Wargovich, M. J. et al. Cancer Epidemiol. Biomarkers Prev. 5: 355-360, 1996), hepatic foci (Singh, A., Arora, A. and Shukla, Y. Modulation of altered hepatic foci induction by diallyl sulphide in Wistar rats. Eur. J. Cancer Prev. 13: 263-269, 2004) and N-nitrosomethylbenzylamine (NMBA)-induced esophageal tumors in rats (Wargovich, M. J., Woods, C., Eng, V. W., Stephens, L. C. and Gary, K. Chemoprevention of N-nitrosomethylbenzylamine-induced esophageal cancer in rats by the naturally occurring thioether, diallyl sulfide. Cancer Res. 48: 6872-6875, 1988) and polycyclic aromatic hydrocarbon-induced skin carcinogenesis in mice (Singh, A. and Shukla, Y. Antitumor activity of diallyl sulfide on polycyclic aromatic hydrocarbon-induced mouse skin carcinogenesis. Cancer Lett. 131: 209-214, 1998). Oral gavage with DATS in male athymic mice significantly inhibited growth of PC-3 human prostate cancer xenografts (Xiao, D., Lew, K. L., Kim, Y. A., Zeng, Y., Hahm, E. R., Dhir, R. and Singh, S. V. Diallyl trisulfide suppresses growth of PC-3 human prostate cancer xenograft in vivo in association with Bax and Bak induction. Clin. Cancer Res. 12: 6836-6843, 2006). Berries (blackberry, raspberry, strawberry, etc) contain multiple bioactive compounds including polyphenols (such as several anthocyanins, ellagic acid, gallic acid etc), phytosterols, beta-carotene and alpha-carotene (Stone, G. D., Chen, T., Kresty, L. A., Aziz, R. M., Reinemann, T. and Nines, R. Protection against esophageal cancer in rodents with lyophilized berries: Potential mechanism. Nutr. Cancer 54: 33-46, 2006; Bravo, L. Polyphenols: Chemistry, dietary sources, metabolism and nutritional significance. Nutr. Rev. 56: 317-333, 1998). Dietary freeze-dried berries were shown to inhibit chemically-induced cancer of the rodent esophagus (Stone, G. D., Chen, T., Kresty, L. A., Aziz, R. M., Reinemann, T. and Nines, R. Protection against esophageal cancer in rodents with lyophilized berries: Potential mechanism. Nutr. Cancer 54: 33-46, 2006). Ellagic acid, one of the active components in berries, inhibits chemical carcinogenesis in lung (Boukharta, M., Jalbert, G. and Castonguay, A. Biodistribution of ellagic acid and dose-related inhibition of lung tumorigenesis in A/J mice. Nut. Cancer 18: 181-189, 1992; Mukhtar, H., Das, M., Del Tito, B. J. Jr. and Bickers, D. R. Protection against 3-methylcholanthrene-induced skin tumorigenesis in Balb/c mice by ellagic acid. Biochem. Biophys. Res. Commun. 119:751-757, 1984; Mandal, S. and Stoner, G. D. Inhibition of N-nitrosobenzylmethylamine-induced esophageal tumorigenesis in rats by ellagic acid. Carcinogenesis 11: 55-61, 1990). Research into food-derived bioactive components for cancer prevention is growing due to the relatively low or no toxicity detected and easy availability. Previous research has shown that the cooked mashed corm of the taro plant, known as poi, has antiproliferative activity against the rat YYT colon cancer cell line in vitro (Brown, A. C., Reitzenstein, J. E., Liu, J. and Jadus, M. R. The anti cancer effects of poi (*Colocasia esculenta*) on Colonic adenocarcinoma cells In Vitro. Phytother. Res.19: 767-771, 2005).

We have identified a therapeutic agent derived from edible roots of the plant *Colocasia esculenta*, commonly known as Taro, and from *Xanthosoma sagittifolium*, commonly known as Malanga Blanca and Yautia. We have shown for the first time that a water soluble extract of the taro (and Malanga Blanca and Yautia) corm (TE) has potent anti-metastatic activity. Using two highly metastatic, estrogen receptor, progesterone receptor and Her-2/neu negative murine mammary tumor cells (line 66.1 and 410.4) transplanted to immune competent syngeneic mice, we have shown that TE can significantly inhibit the lung colonizing ability of both cell lines and spontaneous metastasis of 66.1 cells. We have also shown that addition of TE to 3 of 7 human or murine cancer cell lines profoundly affects cellular morphology and inhibited proliferation in 6 of 9 cancer cell lines in a dose-dependent manner. We also show that TE has anticyclooxygenase activity by inhibiting expression of COX-2, and therefore also has therapeutic potential, for example, in the treatment of inflammatory conditions or diseases.

SUMMARY OF THE INVENTION

It is an object of the invention to provide methods of treating cancer by inhibiting metastasis in a subject, comprising administering a composition comprising a therapeutically effective amount of an extract of *Colocasia*, such as Taro (*Colocasia esculenta*).

It is an object of the invention to provide methods of treating cancer by inhibiting metastasis in a subject, comprising administering a composition comprising a therapeutically effective amount of an extract of *Xanthosoma*, such as Malanga Blanca or Yautia (*Xanthosoma sagittifolium*).

It is an object of the invention to provide pharmaceutical compositions having antimetastatic activity comprising a therapeutic drug derived from *Colocasia*, such as Taro, or *Xanthosoma*, such as Malanga or Yautia.

It is also an object of the invention to provide pharmaceutical compositions having anticyclooxygenase activity comprising a therapeutic drug derived from an aqueous extract from *Colocasia*, such as Taro.

In another object of the invention, the therapeutic agent depends on an intact immune system indicating that the agent may act as an immune response modulator.

In another aspect, the invention relates to a method of treating cancer by inhibiting metastasis in a subject in need thereof, comprising administering to the subject a composition comprising a therapeutically effective amount of an isolated polypeptide from *Colocasia*, such as Taro (*Colocasia esculenta*), wherein the isolated polypeptide comprises an amino acid sequence selected from the group consisting of SEQ ID NO: 1, SEQ ID NO:2 and a combination thereof, wherein the isolated polypeptide has an approximate molecular weight of 30 KD based on size exclusion chromatography.

In another aspect, the present invention relates to a method of treating cancer by inhibiting metastasis in a subject in need thereof, comprising administering to the subject a composition comprising a therapeutically effective amount of an isolated polypeptide from *Xanthosoma*, such as Malanga Blanca or Yautia (*Xanthosoma sagittifolium*), wherein the isolated polypeptide comprises an amino acid sequence selected from the group consisting of SEQ ID NO:3, SEQ ID NO:4 and a combination thereof, wherein the isolated polypeptide has an approximate molecular weight of 30 KD based on size exclusion chromatography. In another aspect, the invention relates to an isolated polypeptide having antimetastatic activity from *Colocasia*, such as Taro (*Colocasia esculenta*), wherein the isolated polypeptide comprises an amino acid sequence selected from the group consisting of SEQ ID NO:1, SEQ ID NO:2 and a combination thereof, wherein the isolated polypeptide has an approximate molecular weight of 30 KD based on size exclusion chromatography.

In another aspect, the invention relates to an isolated polypeptide having antimetastatic activity from *Colocasia*, such as Taro (*Colocasia esculenta*), wherein the isolated polypeptide comprises an amino acid sequence selected from the group consisting of SEQ ID NO:1, SEQ ID NO:2 and a combination thereof, wherein the polypeptide is isolated by a process selected from the group consisting of size exclusion chromatography, ion exchange chromatography, reversed phase liquid chromatography, and combinations thereof.

In another aspect, the invention relates to an isolated polypeptide having antimetastatic activity from *Xanthosoma*, such as Malanga Blanca or Yautia (*Xanthosoma sagittifolium*), wherein the isolated polypeptide comprises an amino acid sequence selected from the group consisting of SEQ ID NO: 3, SEQ ID NO:4 and a combination thereof wherein the isolated polypeptide has an approximate molecular weight of 30 KD based on size exclusion chromatography.

In another aspect, the invention relates to an isolated polypeptide having antimetastatic activity from *Xanthosoma*, such as Malanga Blanca or Yautia (*Xanthosoma sagittifolium*), wherein the isolated polypeptide comprises an amino acid sequence selected from the group consisting of SEQ ID NO: 3, SEQ ID NO:4 and a combination thereof, wherein the polypeptide is isolated by a process selected from the group consisting of size exclusion chromatography, ion exchange chromatography, reversed phase liquid chromatography, and combinations thereof.

In another aspect, the invention relates to pharmaceutical compositions having antimetastatic activity, comprising an isolated polypeptide from *Colocasia,* such as Taro (*Colocasia esculenta*), wherein the polypeptide comprises an amino acid sequence selected from the group consisting of SEQ ID NO:1, SEQ ID NO:2 and a combination thereof, wherein the polypeptide has an approximate molecular weight of 30 KD based on size exclusion chromatography.

In another aspect, the invention provides pharmaceutical compositions having antimetastatic activity, comprising an isolated polypeptide from *Colocasia,* such as Taro (*Colocasia esculenta*), wherein the polypeptide comprises an amino acid sequence selected from the group consisting of SEQ ID NO:1, SEQ ID NO:2 and a combination thereof, wherein the polypeptide is isolated by a process selected from the group consisting of size exclusion chromatography, ion exchange chromatography, reversed phase liquid chromatography, and combinations thereof.

In another aspect, the invention provides pharmaceutical compositions having antimetastatic activity, comprising an isolated polypeptide from *Xanthosoma*, such as Malanga Blanca or Yautia (*Xanthosoma sagittifolium*), wherein the polypeptide comprises an amino acid sequence selected from the group consisting of SEQ ID NO:3, SEQ ID NO:4 and a combination thereof wherein the polypeptide has an approximate molecular weight of 30 KD based on size exclusion chromatography.

In another aspect, the invention provides pharmaceutical compositions having antimetastatic activity, comprising an isolated polypeptide from *Xanthosoma*, such as Malanga Blanca or Yautia (*Xanthosoma sagittifolium*), wherein the polypeptide comprises an amino acid sequence selected from the group consisting of SEQ ID NO:3, SEQ ID NO:4 and a combination thereof wherein the polypeptide is isolated by a process selected from the group consisting of size exclusion chromatography, ion exchange chromatography, reversed phase liquid chromatography, and combinations thereof.

In another aspect, the invention relates to methods of inhibiting cyclooxygenase (COX) activity in a subject in need thereof, comprising administering to the subject a therapeutically effective amount of a composition isolated from *Colocasia*, such as Taro. In some aspects, an inflammatory disease or condition is treated by inhibiting cyclooxygenase (COX) activity. In some aspects, the cyclooxygenase (COX) activity that is inhibited is COX-2 activity. In some aspects. COX-2 mRNA expression is inhibited. In some aspects, the composition comprises a water soluble extract from Taro (*Colocasia esculenta*).

Percent cytotoxicity was calculated using the following formula:

$$\frac{\text{Experimental} - \text{Effector Spontaneous} - \text{Target Spontaneous}}{\text{Target Maximum} - \text{Target Spontaneous}} \times 100$$

Figure 10:
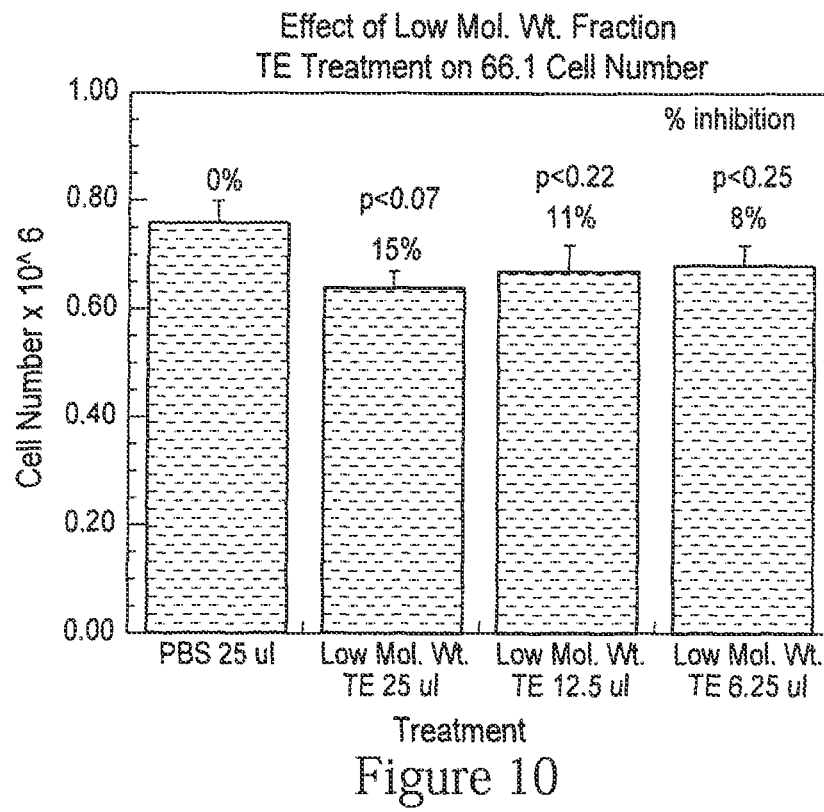

FIG. 10. 66.1 cells were seeded at $2.5\times10^5$ cells/well/1.0 ml media in 24 well plate. PBS or low molecular weight fraction of TE was added as indicated. 48 hours later, cell number was determined.

Figure 11:
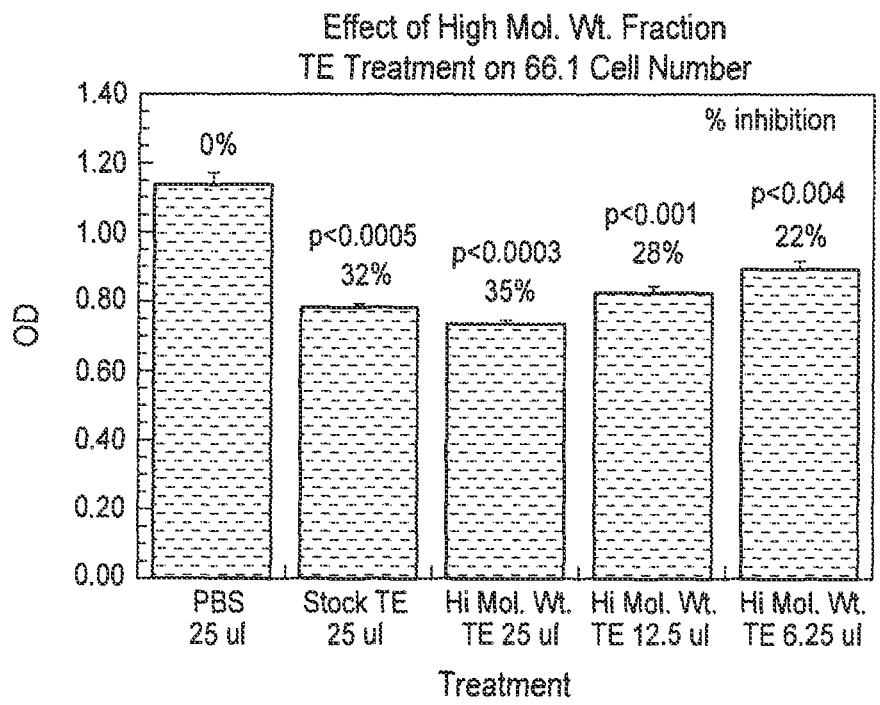

FIG. 11. 66.1 cells were seeded at $1.0\times10^5$ cells/well/1.0 ml media in 24 well plate. PBS or stock or high molecular weight fraction of TE was added as indicated. 48 hours later cell growth was assessed by MTT assay.

Figure 12:
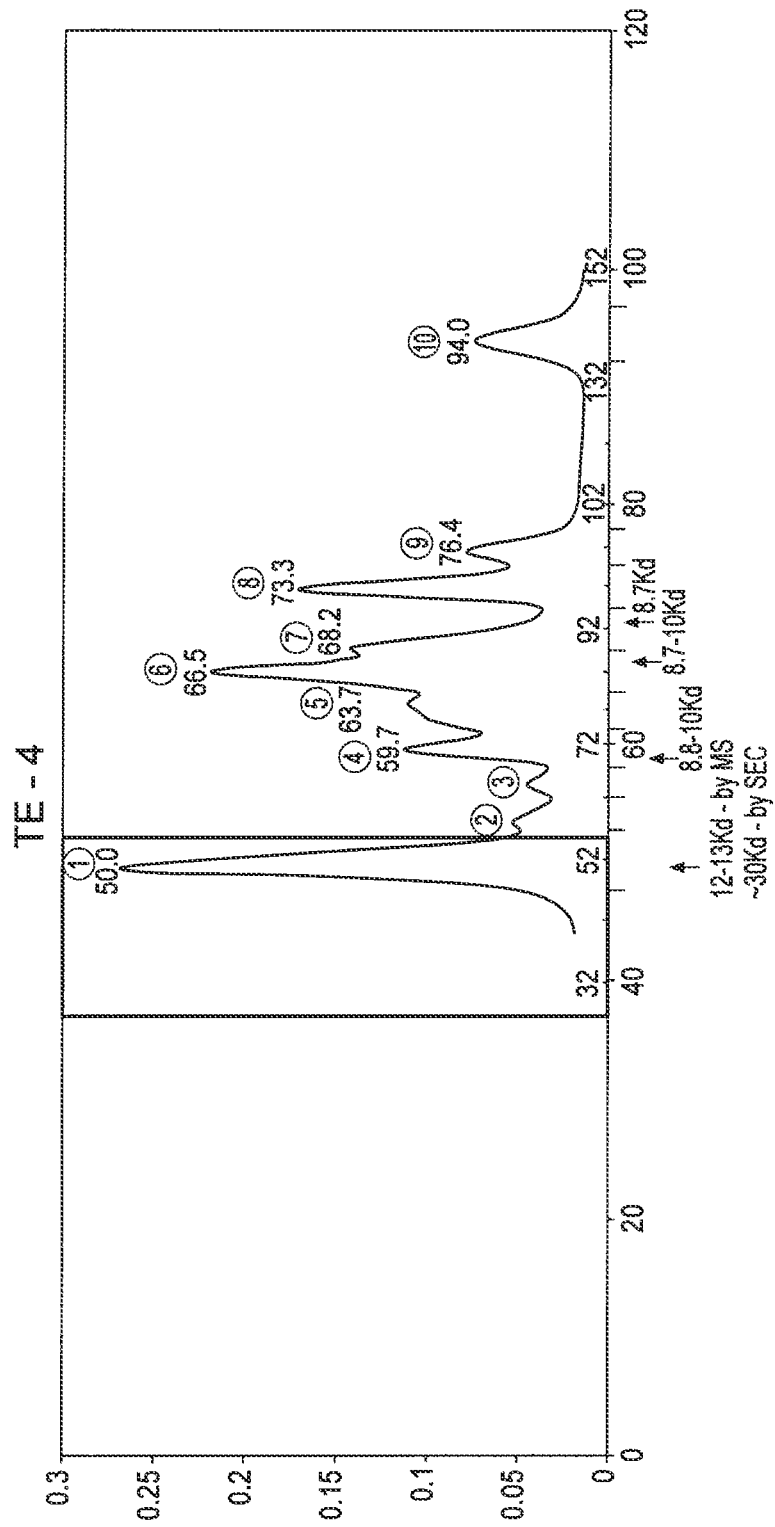

FIG. 12. Fractions Profile of TE from Size Exclusion Chromatography Column. Stock TE was purified using size exclusion chromatography (Bio Suite 250) column.

Figure 13:
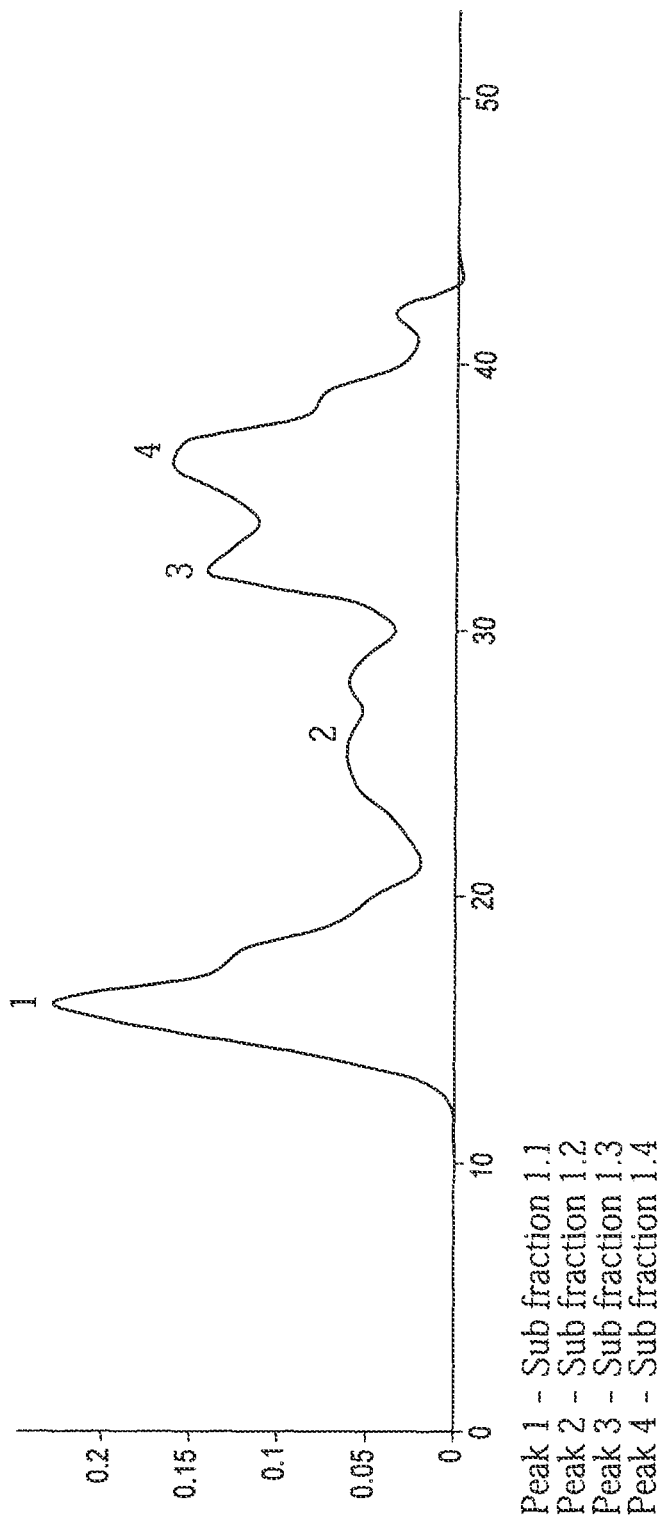

FIG. 13. Sub Fraction Profile of Fraction 1 from Ion-exchange Chromatography. Fraction 1 containing the antimetastatic activity was further purified by ionic exchange column (Poros HQ/20, anion exchange).

Figure 14:
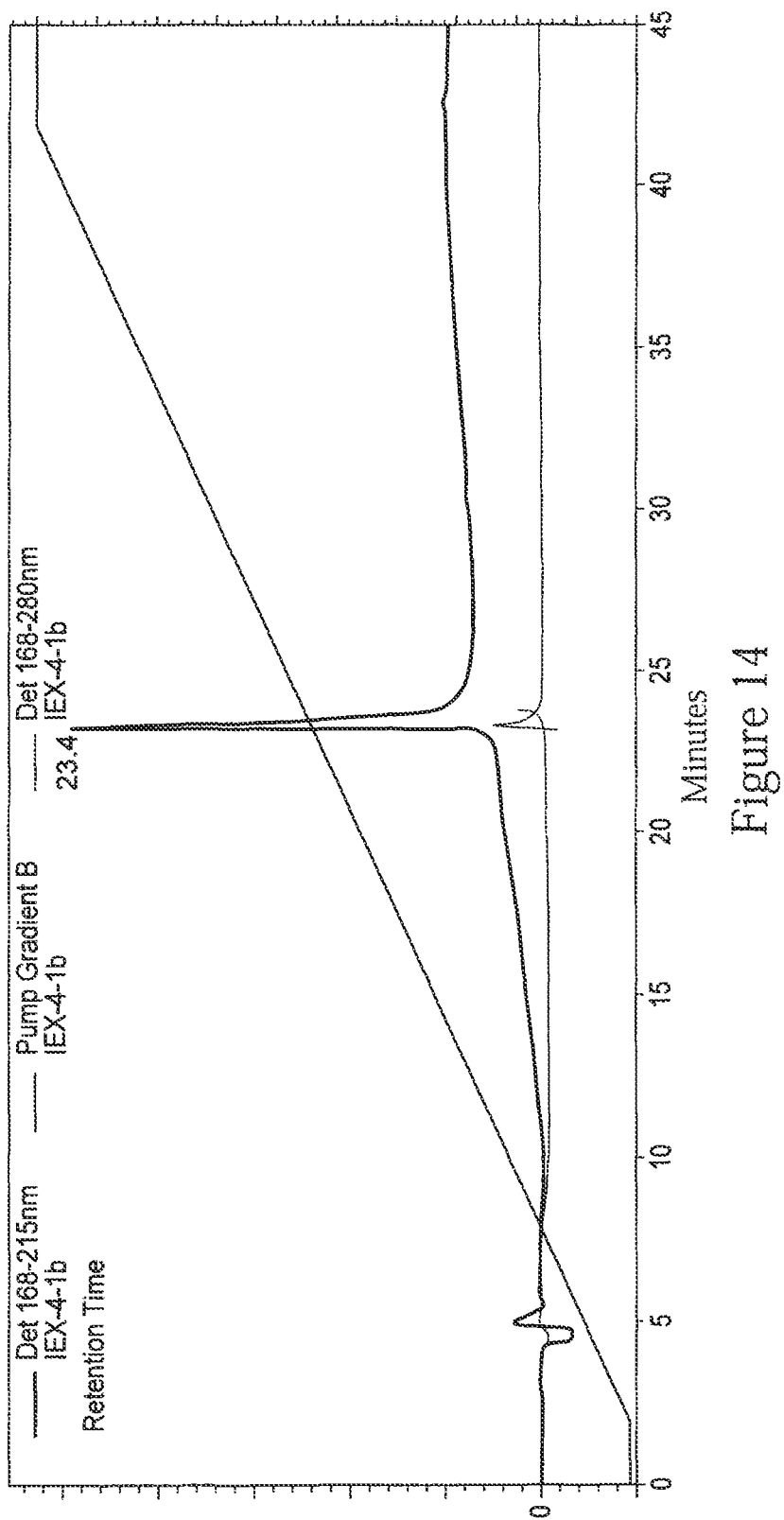

FIG. 14. Fraction Profile from RPLC (Sub fraction 1.1). Each sub fraction of the anion exchange column was analyzed by reversed phase chromatography (Jupiter C5, 300 A) on HPLC.

Figure 15:
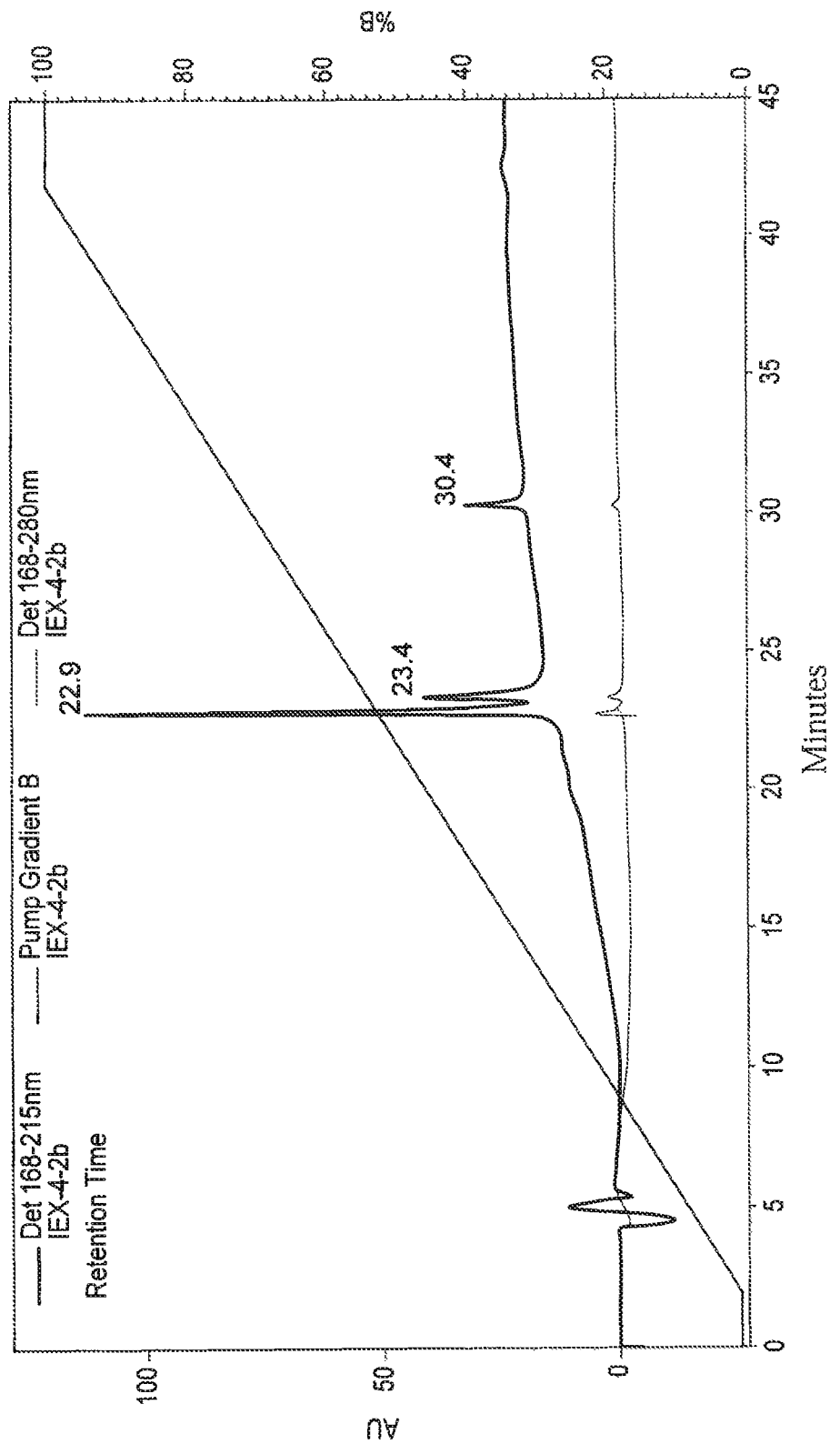

FIG. 15. Fraction Profile from RPLC (Sub fraction 1.2). Each sub fraction of the anion exchange column was analyzed by reversed phase chromatography (Jupiter C5, 300 A) on HPLC.

Figure 16:
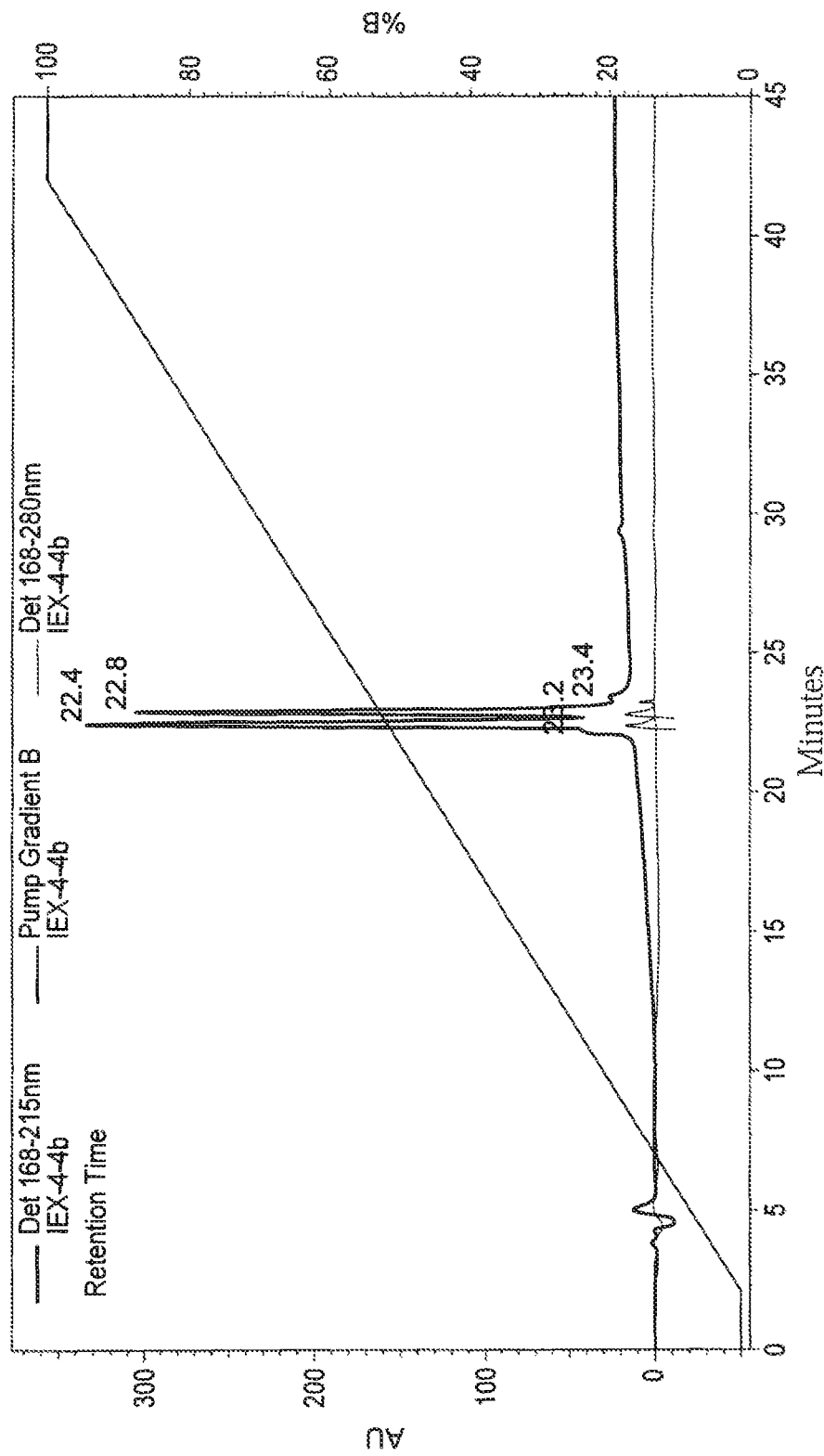

FIG. 16. Fraction Profile from RPLC (Sub fraction 1.3). Each sub fraction of the anion exchange column was analyzed by reversed phase chromatography (Jupiter C5, 300 A) on HPLC.

Figure 17:
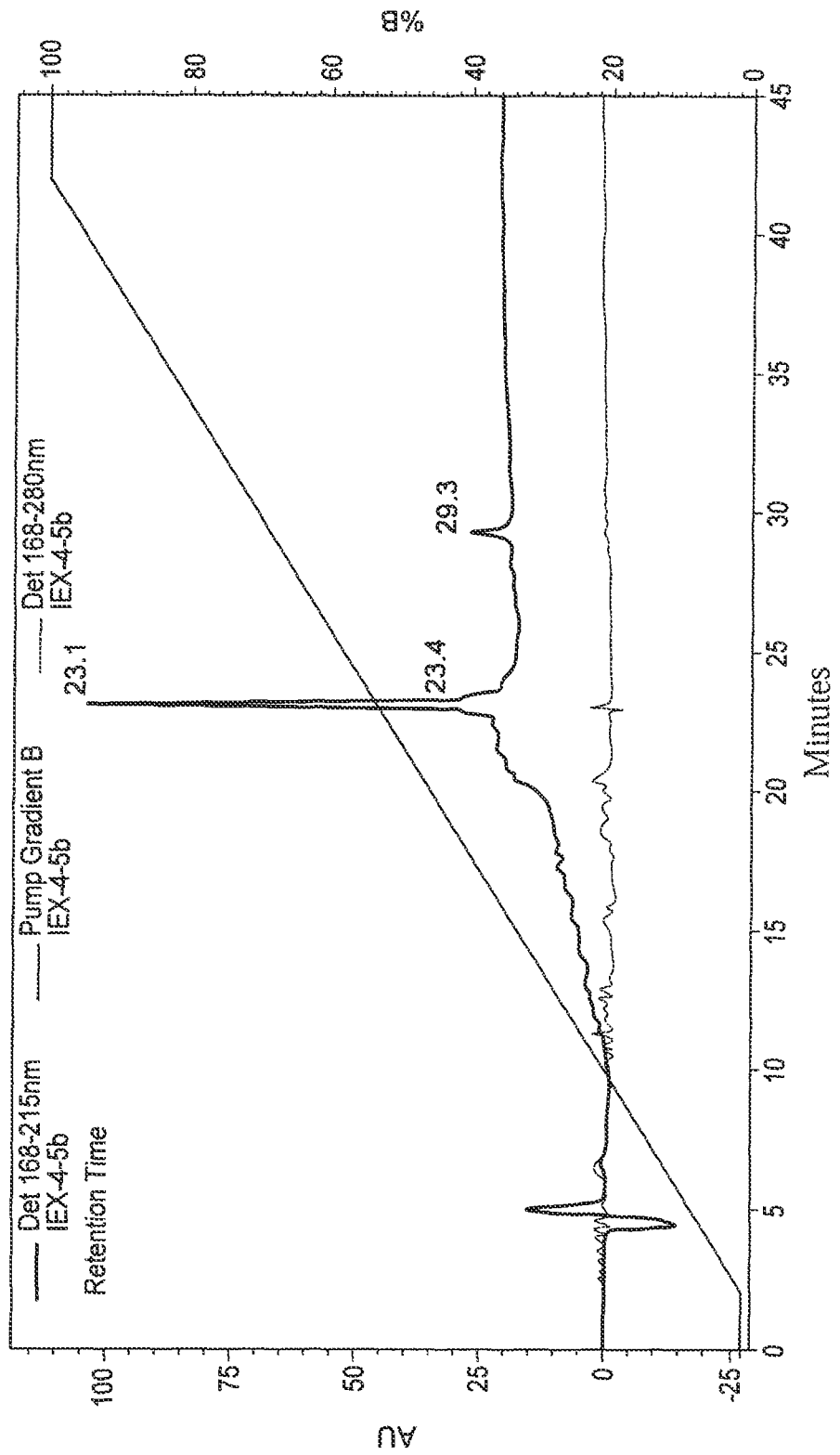

FIG. 17. Fraction Profile from RPLC (Sub fraction 1.4).

Figure 18:
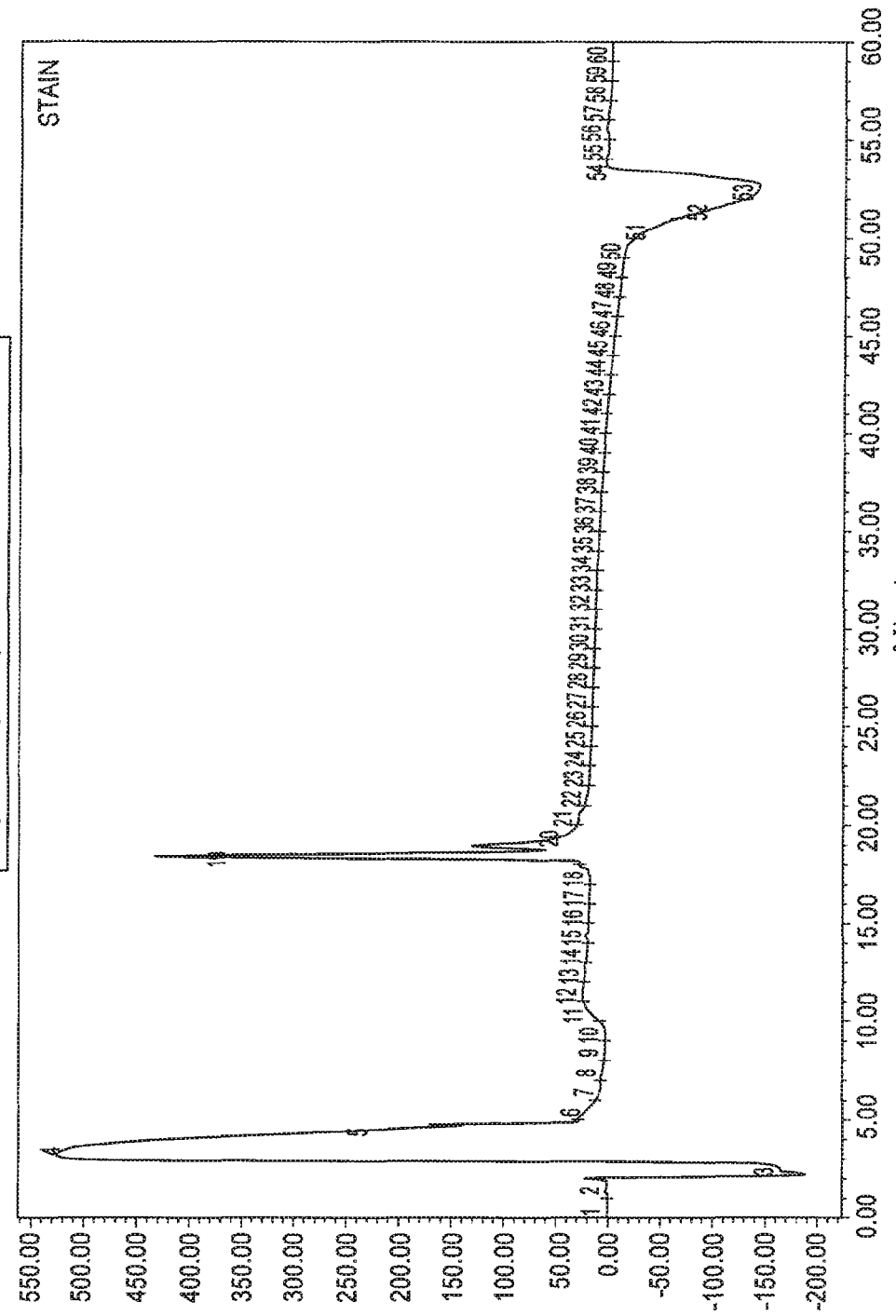

FIG. 18. Each sub fraction of the anion exchange column was analyzed by reversed phase chromatography (Jupiter CS, 300 A) on HPLC. Analysis of sub fraction 1.1.1-1.1.5 using Symmetry C4 column.

Figure 19:
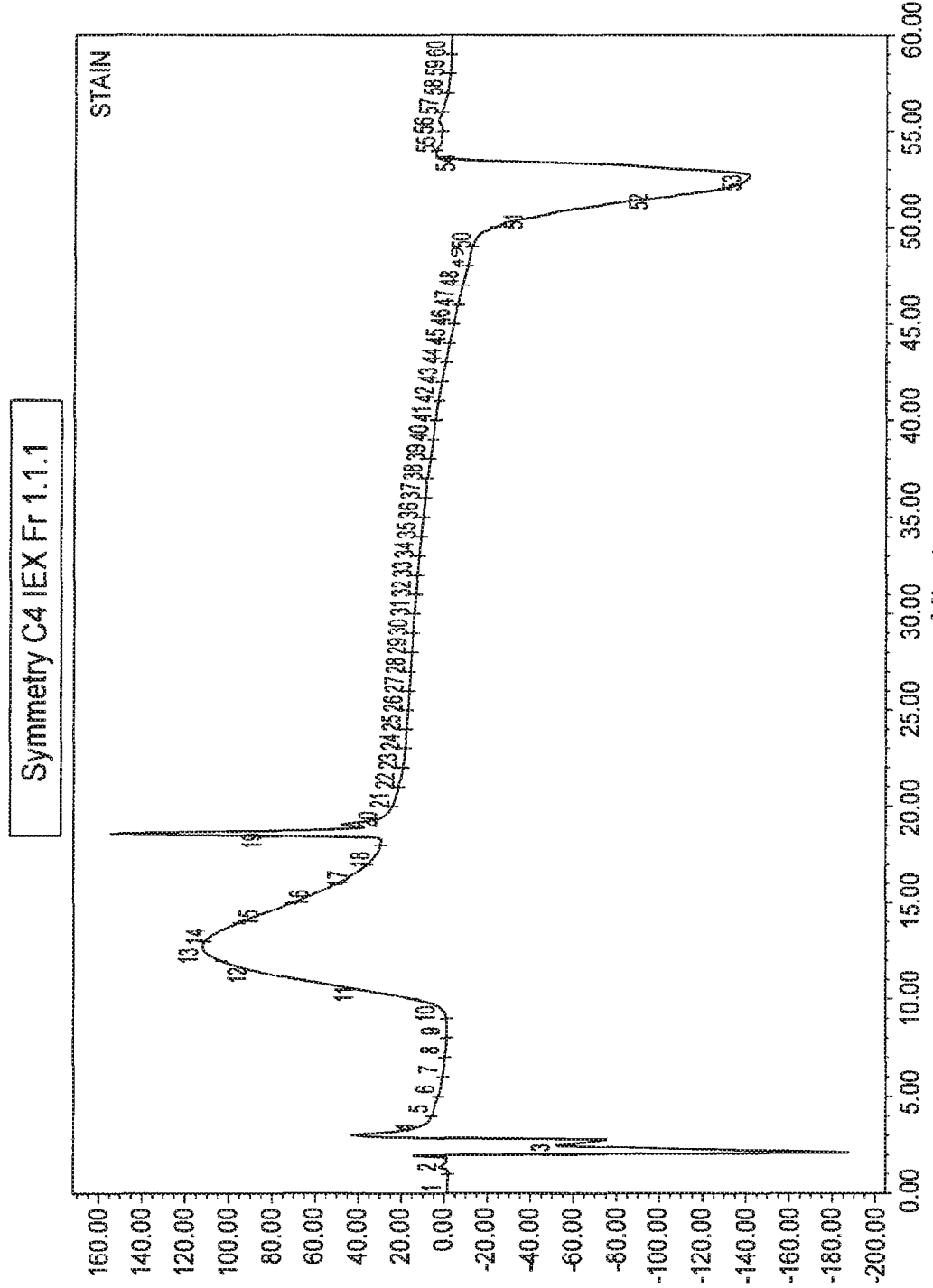

FIG. 19. Analysis of sub fraction 1.1.1 using Symmetry C4 column.

Figure 20:
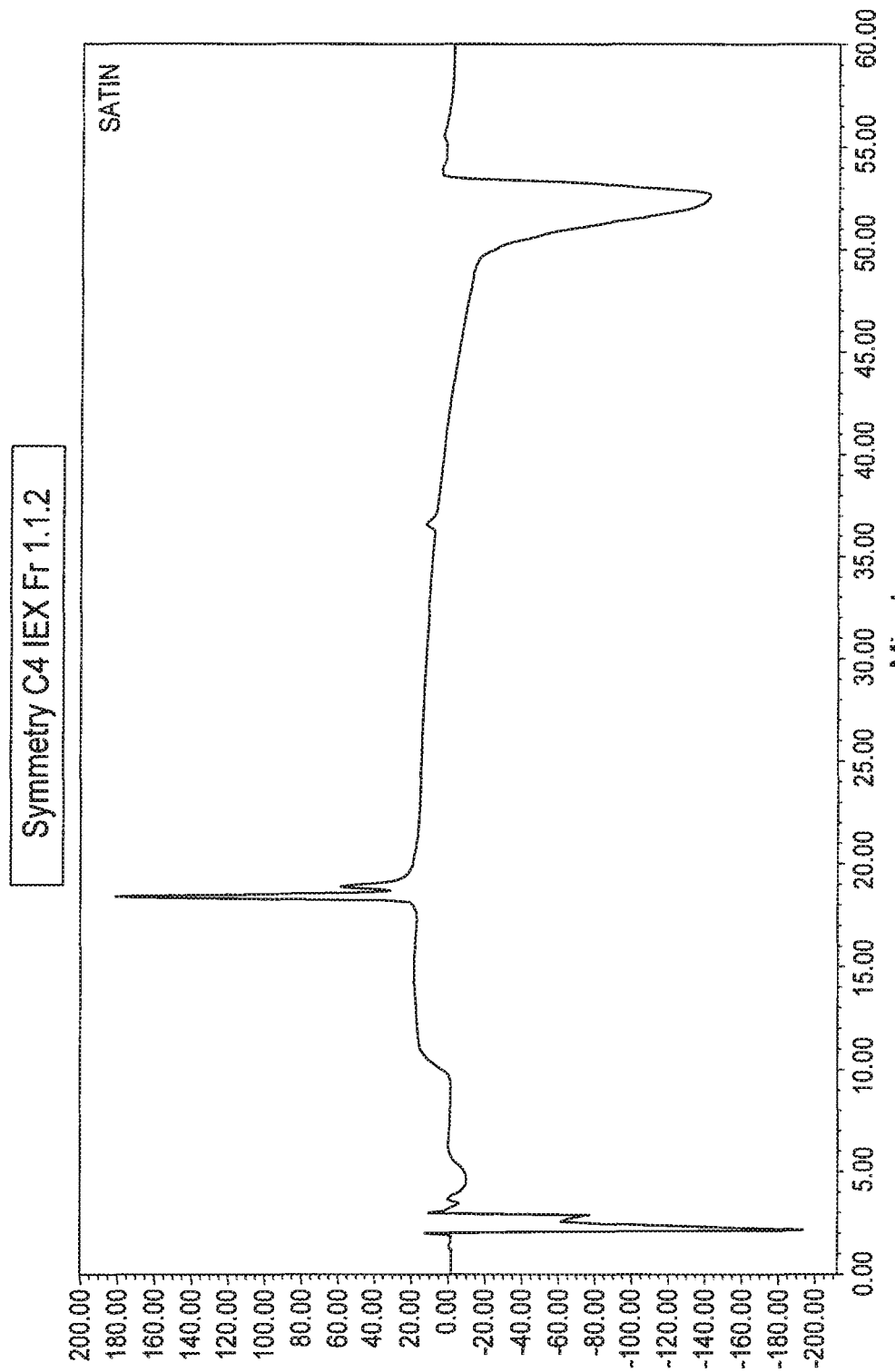

FIG. 20. Analysis of sub fraction 1.1.2 using Symmetry C4 column.

Figure 21:
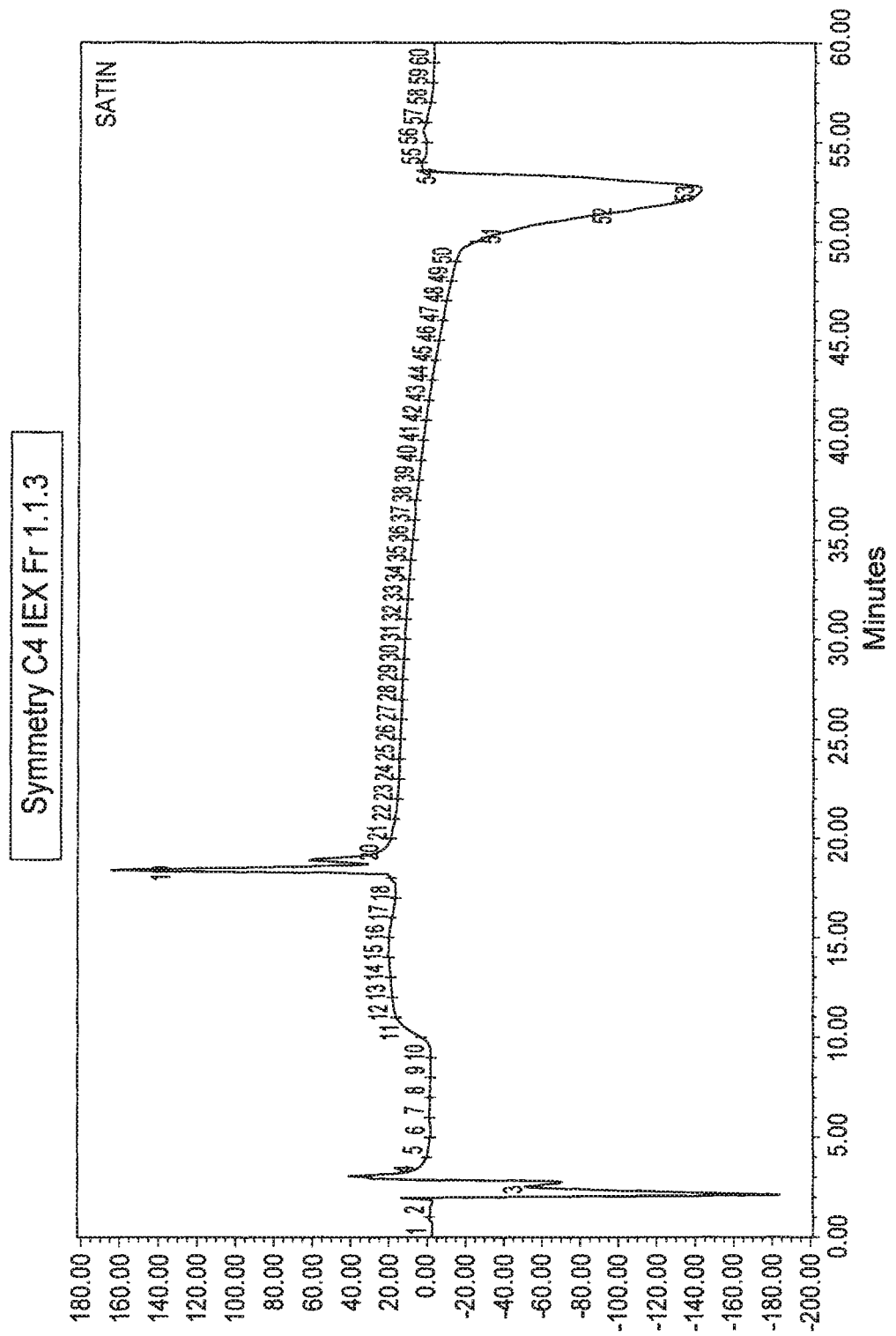

FIG. 21. Analysis of sub fraction 1.1.3 using Symmetry C4 column.

Figure 22:
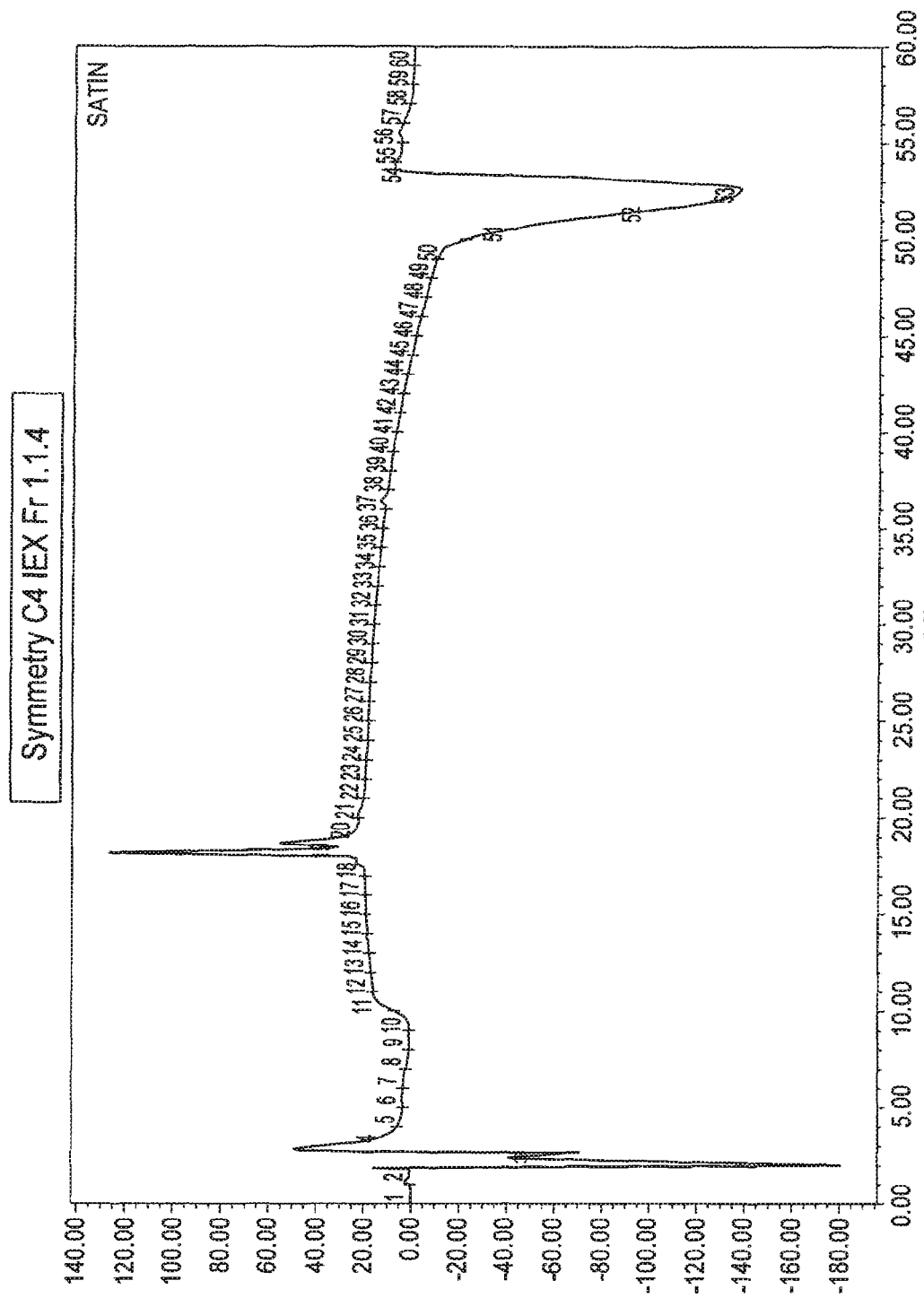

FIG. 22. Analysis of sub fraction 1.1.4 using Symmetry C4 column.

Figure 23:
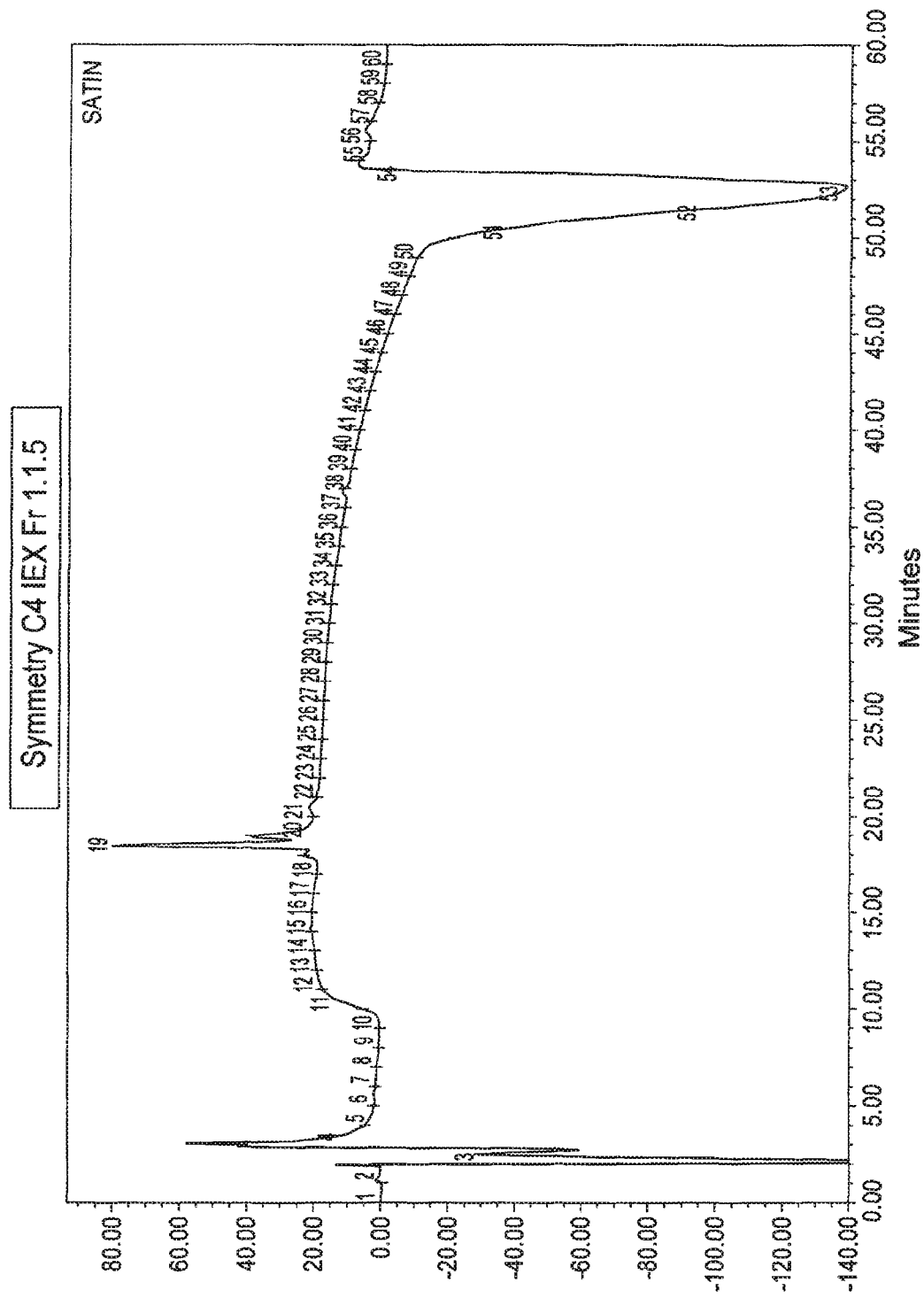

FIG. 23. Analysis of sub fraction 1.1.5 using Symmetry C4 column.

Figure 24:
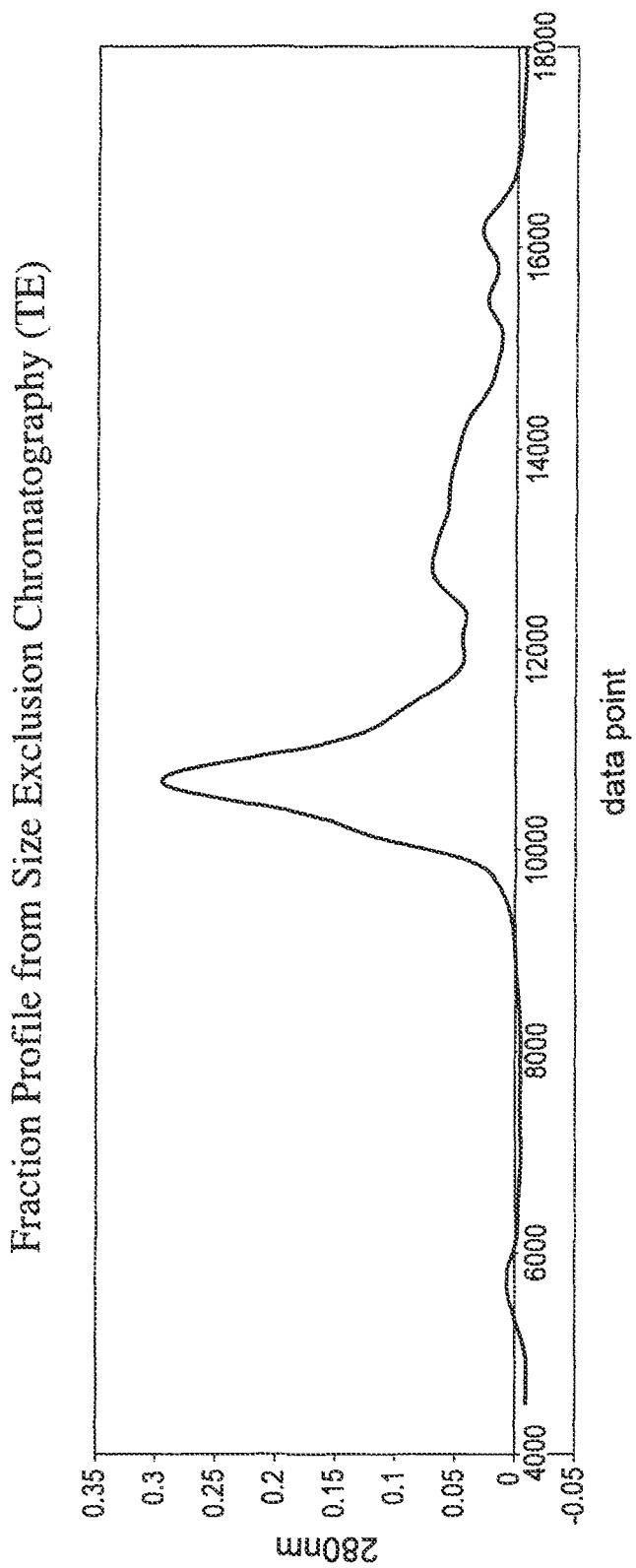

FIG. 24. The fraction profile of TE from Size Exclusion Chromatography.

Figure 25:
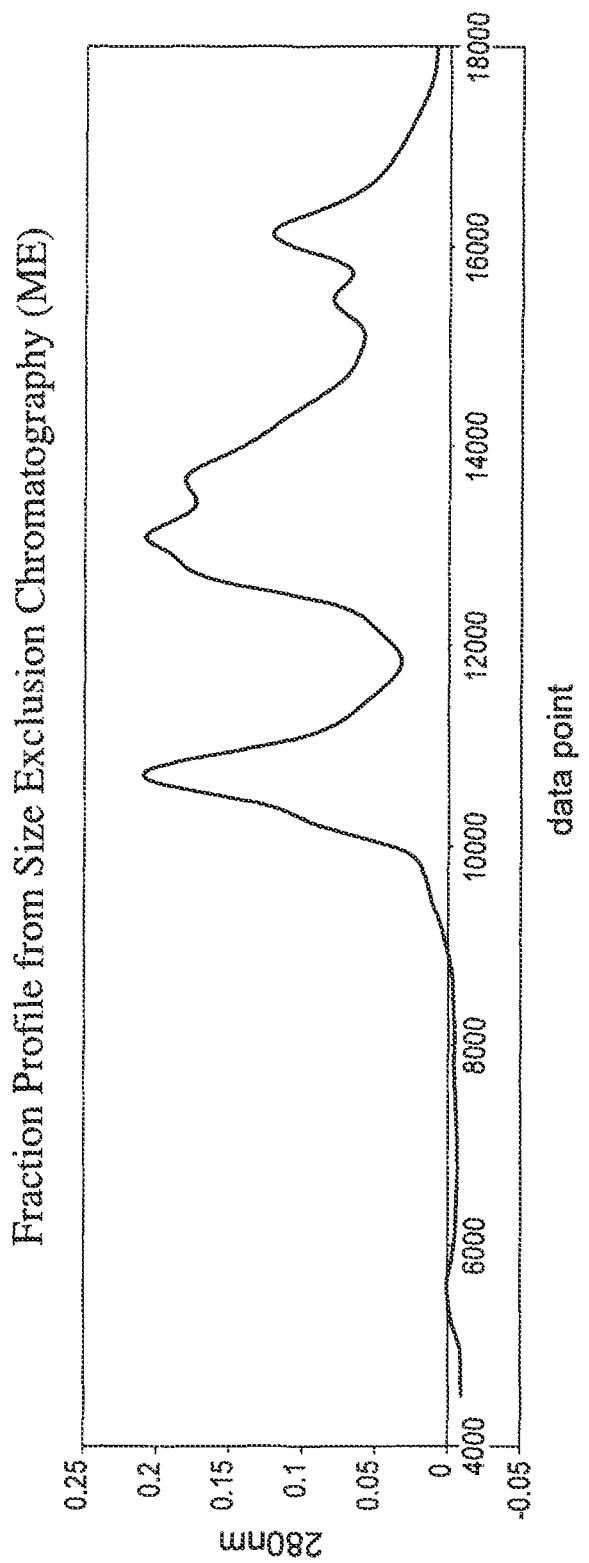

FIG. 25. The fraction profile of ME from Size Exclusion Chromatography.

Figure 26:
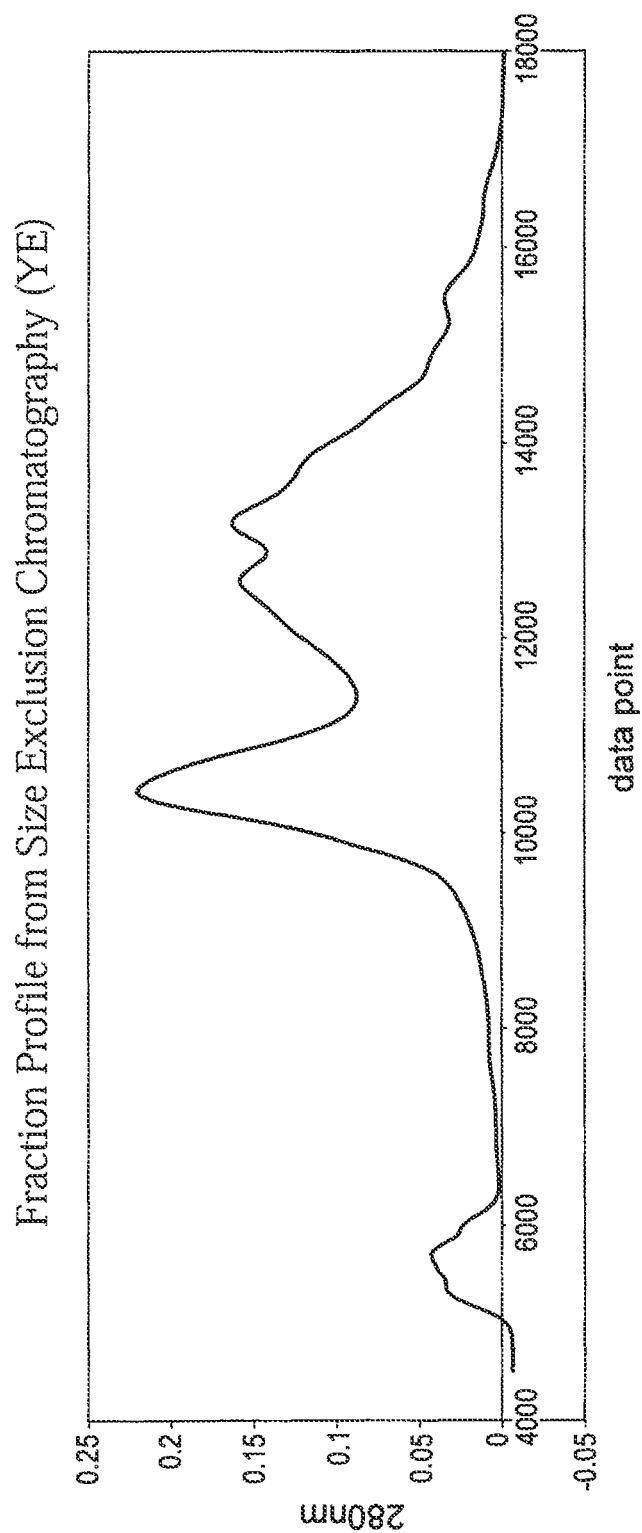

FIG. 26. The fraction profile of YE from Size Exclusion Chromatography.

Figure 27:
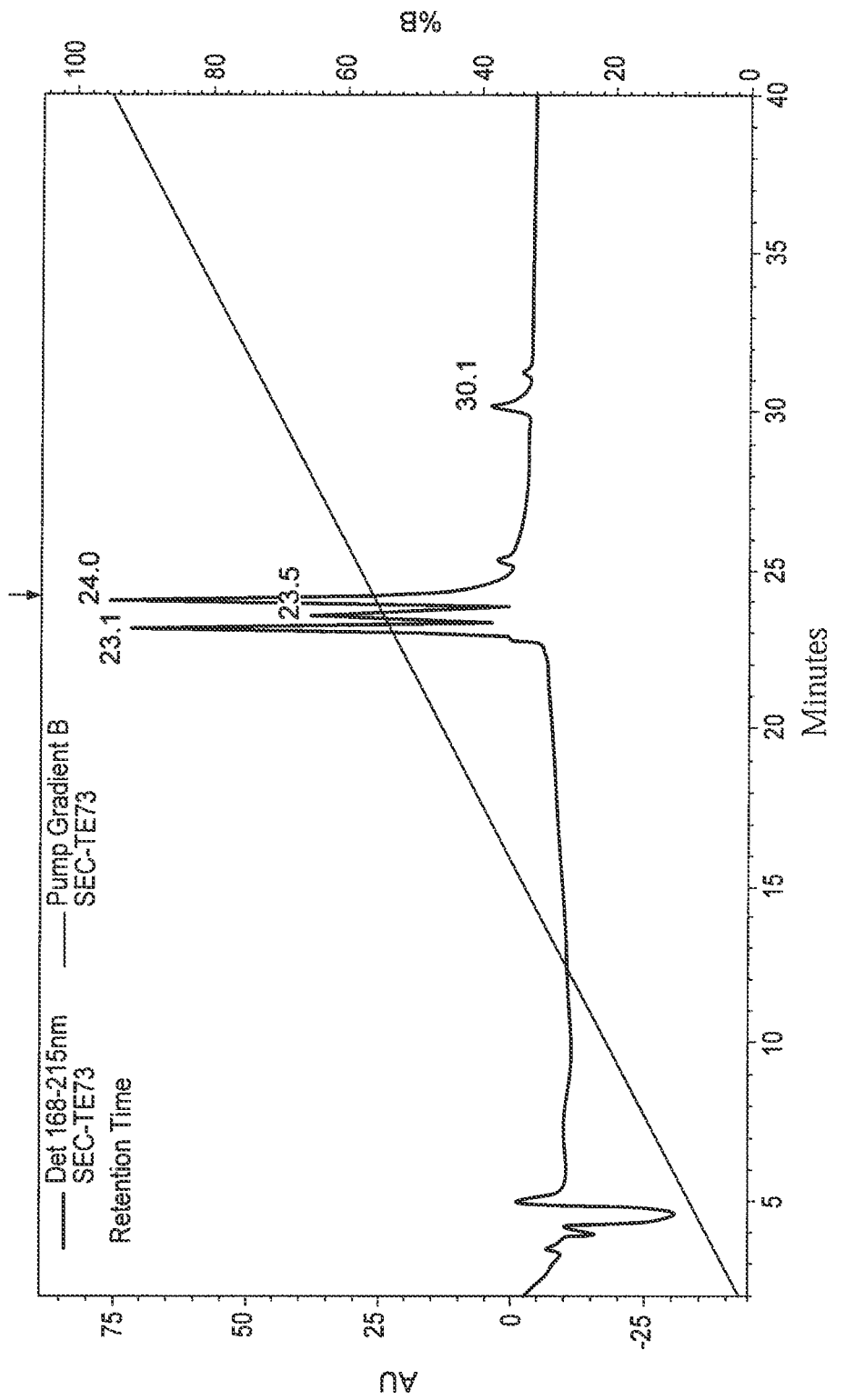

FIG. 27. The fraction profile of TE from Reversed Phase Liquid Chromatography.

Figure 28:
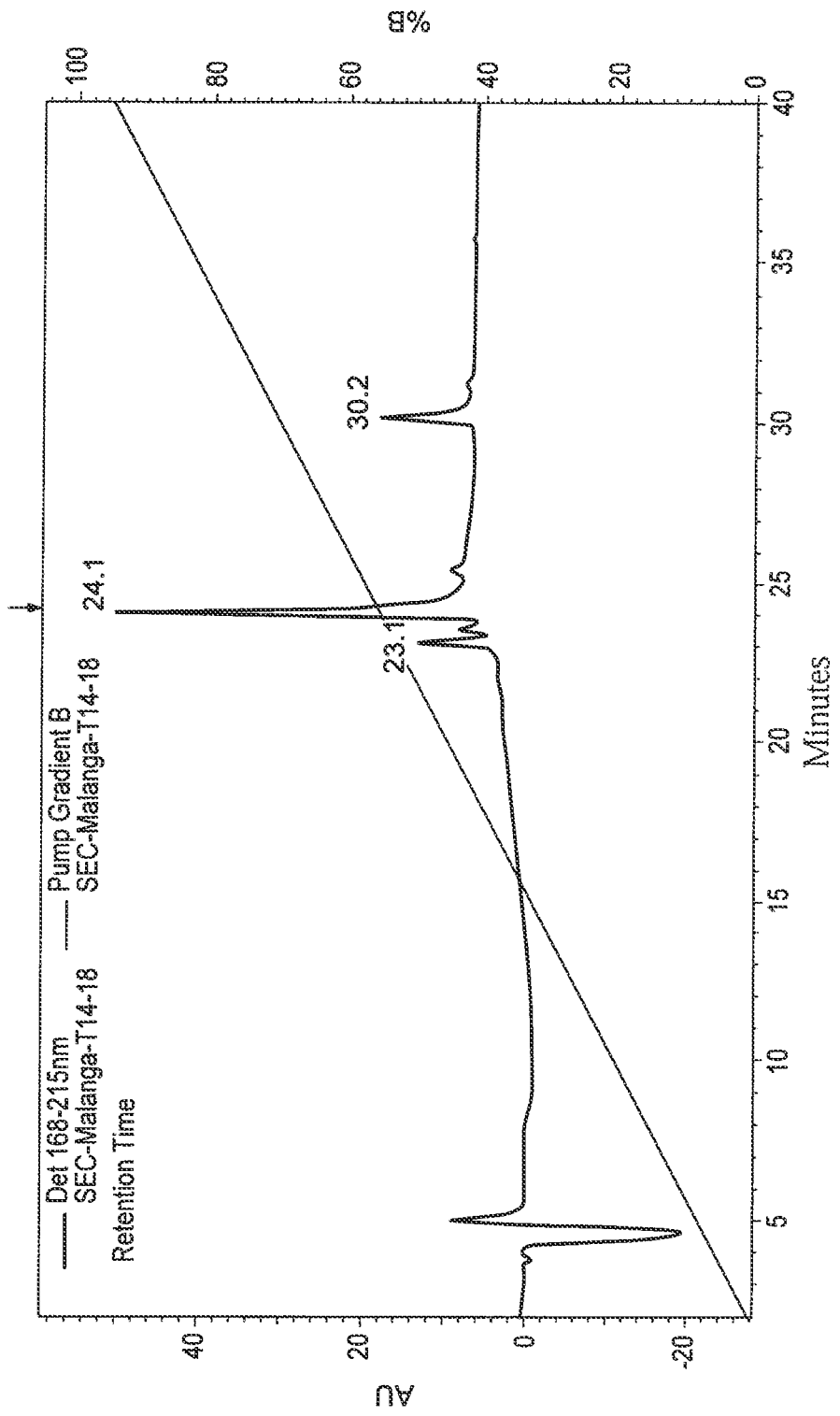

FIG. 28. The fraction profile of ME from Reversed Phase Liquid Chromatography.

Figure 29:
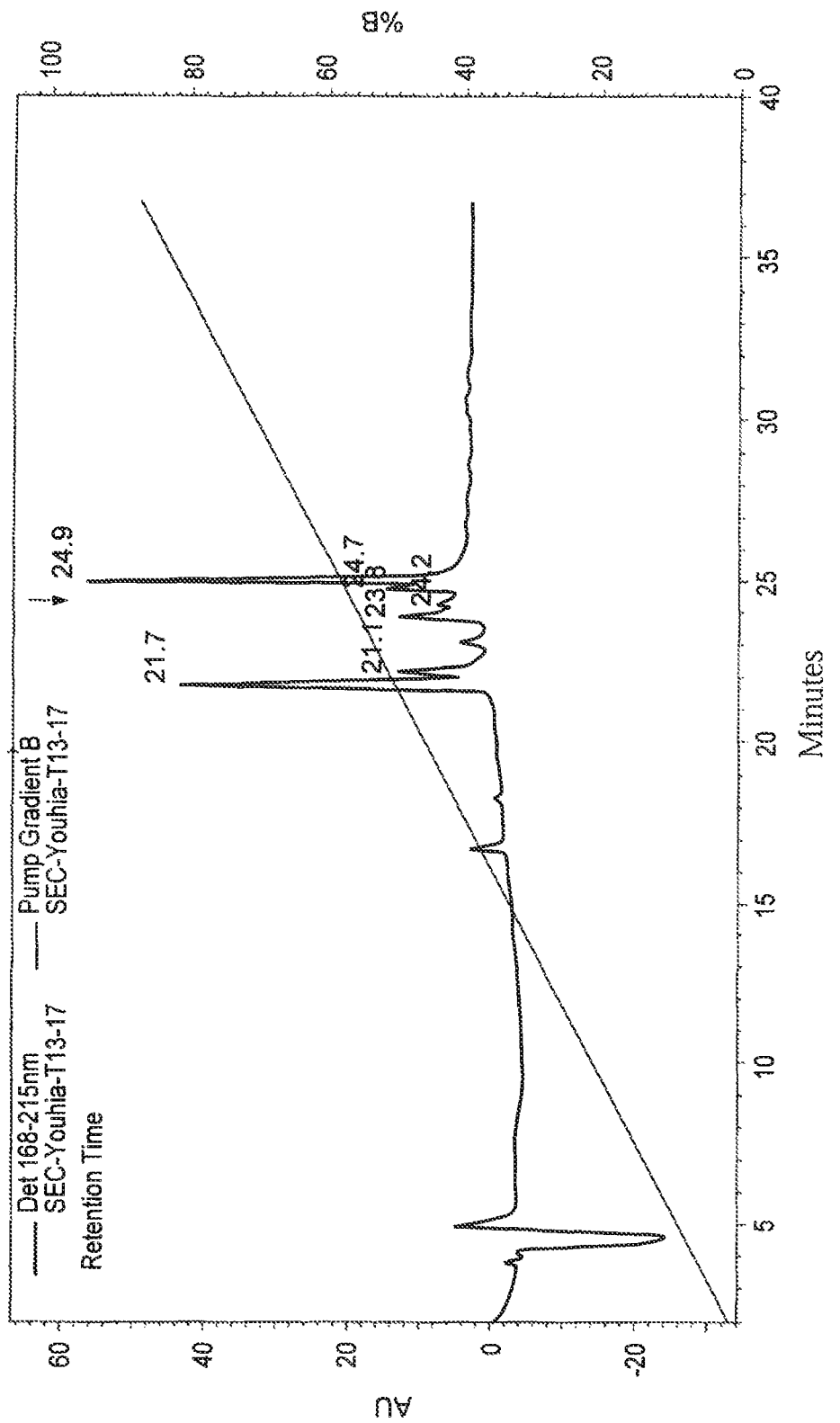

FIG. 29. The fraction profile of YE from Reversed Phase Liquid Chromatography.

FIG. 30. Multiple sequence alignment. Represents the amino acid sequences of the three taro proteins (tarin, lectin and 12 kD storage protein) and the comparison of amino acid sequence location of peak 1 and peak 2 with these three proteins.

Figure 31:
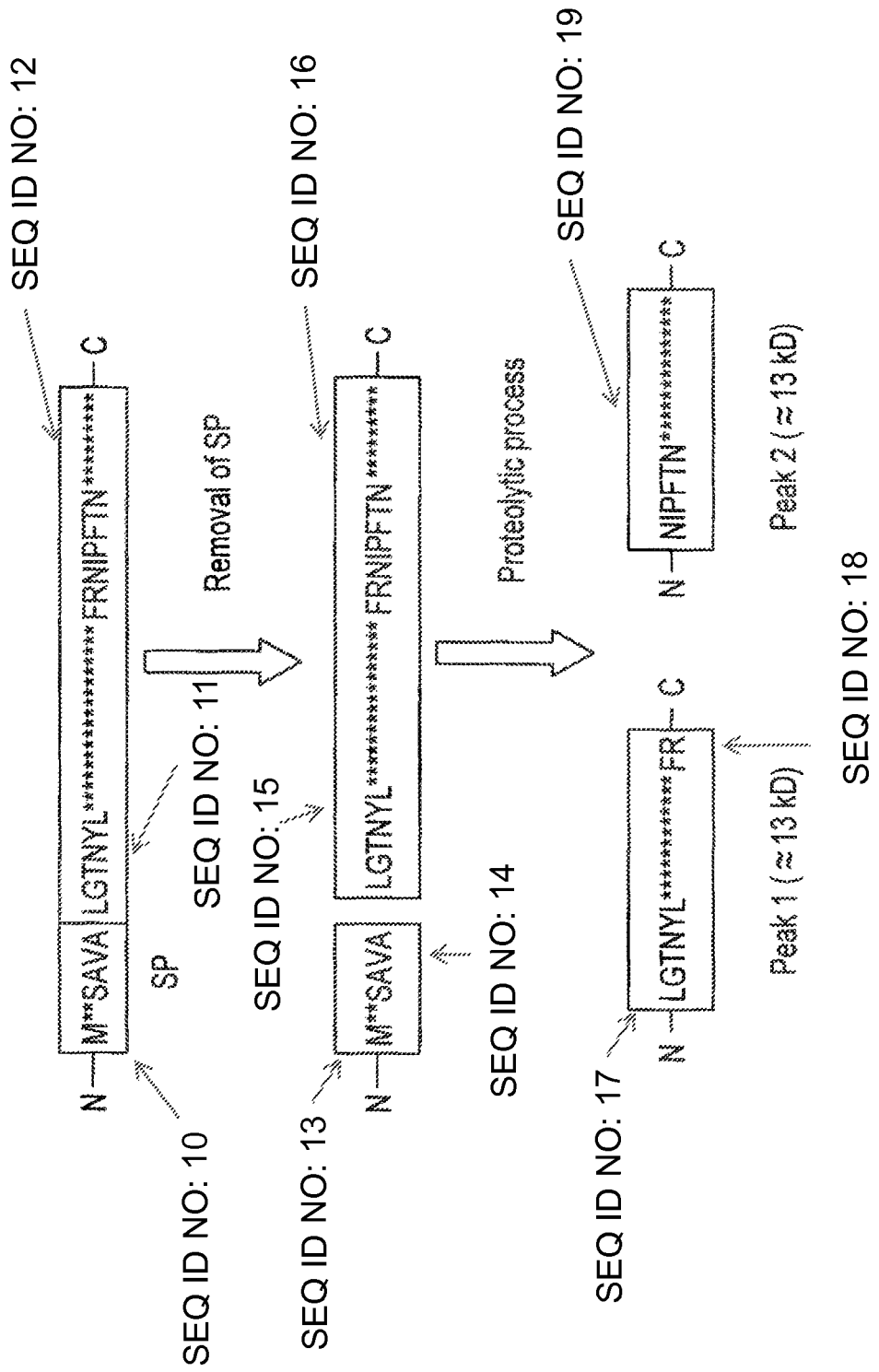

FIG. 31. Schematic representation of the post-translational processing of the active compound. The three taro proteins: 12 kD storage protein, tarin and lectin, appear to undergo an identical two-step maturation process to generate mature forms with two fragments. The signal peptides are removed by a cleavage at SAVA-LGTN followed by a second proteolytic cleavage at FR-NIP to generate two fragments.

DETAILED DESCRIPTION OF THE INVENTION

Reference will now be made in detail to the presently preferred embodiments of the invention which, together with the drawings and the following examples, serve to explain the principles of the invention. These embodiments describe in sufficient detail to enable those skilled in the art to practice the invention, and it is understood that other embodiments may be utilized, and that structural, biological, and chemical changes may be made without departing from the spirit and scope of the present invention. Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, the preferred methods, devices, and materials now described.

One skilled in the art may refer to general reference texts for detailed descriptions of known techniques discussed herein or equivalent techniques. These texts include Current Protocols in Molecular Biology (Ausubel et. al., eds. John Wiley & Sons, N.Y. and supplements thereto), Current Protocols in Immunology (Coligan et al., eds., John Wiley St Sons, N.Y. and supplements thereto), Current Protocols in Pharmacology (Enna et al., eds. John Wiley & Sons, N.Y. and supplements thereto) and Remington: The Science and Practice of Pharmacy (Lippincott Williams & Wilicins, 2Vt edition (2005)), for example.

Providing a therapy or "treating" cancer refers to indicia of success in the treatment, amelioration or prevention of cancer, including any objective or subjective parameter such as abatement, inhibiting metastasis, remission, diminishing of symptoms of making the disease, pathology or condition more tolerable to the patient, slowing the rate of degeneration or decline, making the final point of degeneration less debilitating, or improving a patient's physical or mental well-being. Those in need of treatment include those already with cancer as well as those prone to have cancer or in those in whom cancer is to be prevented.

Suitable cancers which can be treated using the compositions and methods of the present invention include cancers classified by site or by histological type. Cancers classified by site include cancer of the oral cavity and pharynx (lip, tongue, salivary gland, floor of mouth, gum and other mouth, nasopharynx, tonsil, oropharynx, hypopharynx, other oral/pharynx); cancers of the digestive system (esophagus; stomach; small intestine; colon and rectum; anus, anal canal, and anorectum; liver; intrahepatic bile duct; gallbladder; other biliary; pancreas; retroperitoneum; peritoneum, omentum, and mesentery; other digestive); cancers of the respiratory system (nasal cavity, middle ear, and sinuses; larynx; lung and bronchus; pleura; trachea, mediastinum, and other respiratory); cancers of the mesothelioma; bones and joints; and soft tissue, including heart; skin cancers, including melanomas and other non-epithelial skin cancers; Kaposi's sarcoma and breast cancer; cancer of the female genital system (cervix uteri; corpus uteri; uterus, nos; ovary; vagina; vulva; and other female genital); cancers of the male genital system (prostate gland; testis; penis; and other male genital); cancers of the urinary system (urinary bladder; kidney and renal pelvis; ureter; and other urinary); cancers of the eye and orbit; cancers of the brain and nervous system (brain; and other nervous system); cancers of the endocrine system (thyroid gland and other endocrine, including thymus); cancers of the lymphomas (hodgkin's disease and non-hodgkin's lymphoma), multiple myeloma, and leukemias (lymphocytic leukemia; myeloid leukemia; monocytic leukemia; and other leukemias).

Other cancers, classified by histological type, that may be treated include, but are not limited to, Neoplasm, malignant; Carcinoma, NOS; Carcinoma, undifferentiated, NOS; Giant and spindle cell carcinoma; Small cell carcinoma, NOS; Papillary carcinoma, NOS; Squamous cell carcinoma, NOS; Lymphoepithelial carcinoma; Basal cell carcinoma, NOS; Pilomatrix carcinoma; Transitional cell carcinoma, NOS; Papillary transitional cell carcinoma; Adenocarcinoma, NOS; Gastrinoma, malignant; Cholangiocarcinoma; Hepatocellular carcinoma, NOS; Combined hepatocellular carcinoma and cholangiocarcinoma; Trabecular adenocarcinoma; Adenoid cystic carcinoma; Adenocarcinoma in adenomatous polyp; Adenocarcinoma, familial polyposis coli; Solid carcinoma, NOS; Carcinoid tumor, malignant; Branchiolo-alveolar adenocarcinoma; Papillary adenocarcinoma, NOS; Chromophobe carcinoma; Acidophil carcinoma; Oxyphilic adenocarcinoma; Basophil carcinoma; Clear cell adenocarcinoma, NOS; Granular cell carcinoma; Follicular adenocarcinoma, NOS; Papillary and follicular adenocarcinoma; Non-encapsulating sclerosing carcinoma; Adrenal cortical carcinoma; Endometroid carcinoma; Skin appendage carcinoma; Apocrine adenocarcinoma; Sebaceous adenocarcinoma; Ceruminous adenocarcinoma; Mucoepidermoid carcinoma; Cystadenocarcinoma, NOS; Papillary cystadenocarcinoma, NOS; Papillary serous cystadenocarcinoma; Mucinous cystadenocarcinoma, NOS; Mucinous adenocarcinoma; Signet ring cell carcinoma; Infiltrating duct carcinoma; Medullary carcinoma, NOS; Lobular carcinoma; Inflammatory carcinoma; Paget's disease, mammary; Acinar cell carcinoma; Adenosquamous carcinoma; Adenocarcinoma w/squamous metaplasia; Thymoma, malignant; Ovarian stromal tumor, malignant; Thecoma, malignant; Granulosa cell tumor, malignant; Androblastoma, malignant; Sertoli cell carcinoma; Leydig cell tumor, malignant; Lipid cell tumor, malignant; Paraganglioma, malignant; Extra-mammary paraganglioma, malignant; Pheochromocytoma; Glomangiosarcoma; Malignant melanoma, NOS; Amelanotic melanoma; Superficial spreading melanoma; Malignant melanoma in giant pigmented nevus; Epithelioid cell melanoma; Blue nevus, malignant; Sarcoma, NOS; Fibrosarcoma, NOS; Fibrous histiocytoma, malignant; Myxosarcoma; Liposarcoma, NOS; Leiomyosarcoma, NOS; Rhabdomyosarcoma, NOS; Embryonal rhabdomyosarcoma; Alveolar rhabdomyosarcoma; Stromal sarcoma, NOS; Mixed tumor, malignant, NOS; Mullerian mixed tumor; Nephroblastoma; Hepatoblastoma; Carcinosarcoma, NOS; Mesenchymoma, malignant; Brenner tumor, malignant; Phyllodes tumor, malignant; Synovial sarcoma, NOS; Mesothelioma, malignant; Dysgerminoma; Embryonal carcinoma, NOS; Teratoma, malignant, NOS; Struma ovari, malignant; Choriocarcinoma; Mesonephroma, malignant; Hemangiosarcoma; Hemangioendothelioma, malignant; Kaposi's sarcoma; Hemangiopericytoma, malignant; Lymphangiosarcoma; Osteosarcoma, NOS; Juxtacortical osteosarcoma; Chondrosarcoma, NOS; Chondroblastoma, malignant; Mesenchymal chondrosarcoma; Giant cell tumor of bone; Ewing's sarcoma; Odontogenic tumor, malignant; Ameloblastic odontosarcoma; Ameloblastoma, malignant; Ameloblastic fibrosarcoma; Pinealoma, malignant; Chordoma; Glioma, malignant; Ependymoma, NOS; Astrocytoma, NOS; Protoplasmic astrocytoma; Fibrillary astrocytoma; Astroblastoma; Glioblastoma, NOS; Oligodendroglioma, NOS; Oligodendroblastoma; Primitive neuroectodermal; Cerebellar sarcoma, NOS; Ganglioneuroblastoma; Neuroblastoma, NOS; Retinoblastoma, NOS; Olfactory neurogenic tumor; Meningioma, malignant; Neurofibrosarcoma; Neurilemmoma, malignant; Granular cell tumor, malignant; Malignant lymphoma, NOS; Hodgkin's disease, NOS; Hodgkin's; paragranuloma, NOS; Malignant lymphoma, small lymphocytic; Malignant lymphoma, large cell, diffuse; Malignant lymphoma, follicular, NOS; Mycosis fungoides; Other specified non-Hodgkin's lymphomas; Malignant histiocytosis; Multiple myeloma; Mast cell sarcoma; Immunoproliferative small intestinal disease; Leukemia, NOS; Lymphoid leukemia, NOS; Plasma cell leukemia; Erythroleukemia; Lymphosarcoma cell leukemia; Myeloid leukemia, NOS; Basophilic leukemia; Eosinophilic leukemia; Monocytic leukemia, NOS; Mast cell leukemia; Megakaryoblastic leukemia; Myeloid sarcoma; and Hairy cell leukemia.

The compositions of the invention can be administered in combination with existing cancer therapies, including cancer drugs, radiation, and chemotherapy.

Preferred subjects for treatment include animals, most preferably mammalian species, such as humans, mice, rats, and domestic animals such as dogs, cats, and the like, subject to disease and other pathological conditions. A "patient" refers to a subject, preferably a mammalian subject (including human).

Certain embodiments of the present invention relate to pharmaceutical compositions comprising one or more therapeutic agents, which are capable of prophylactic and/or therapeutic treatment of cancer and related conditions.

In some embodiments, the invention provides compositions having antimetastatic activity, comprising an isolated polypeptide comprising an amino acid sequence selected from the group consisting of SEQ ID NO:3, SEQ ID NO:4 and a combination thereof wherein the polypeptide has an approximate molecular weight of 30 KD based on size exclusion chromatography.

In some embodiments, the invention provides compositions having antimetastatic activity comprising an isolated polypeptide comprising an amino acid sequence selected from the group consisting of SEQ ID NO: 1, SEQ ID NO:2 and a combination thereof, wherein the isolated polypeptide has an approximate molecular weight of 30 KD based on size exclusion chromatography.

In some embodiments, the invention provides antimetastatic compositions comprising a water soluble extract or isolated polypeptide from a plant of a genus selected from the group consisting of *Colocasia* and *Xanthosoma*. In some embodiments, the plant is Taro (*Colocasia esculenta*), Malanga Blanca (*Xanthosoma sagittifolium*), Yautia (*Xanthosoma sagittifolium*) and combinations thereof, wherein the extract or isolated polypeptide is therapeutically effective in the treatment of cancer by inhibiting metastasis.

In some embodiments, the invention provides compositions from *Colocasia*, such as Taro, that have anticyclooxygenase activity, such as anti-COX-2 activity, and are therapeutically effective in the treatment of inflammatory diseases or conditions.

Non-limiting members of the genus *Colocasia*, which may provide a source for the antimetastatic or anticyclooxygenase compositions, include plants commonly referred to as Taro, Eddoe and Dasheen and include species, such as, for example, *Colocasia affinis, Colocasia bicolor, Colocasia esculenta, Colocasia fallax, Colocasia fontanesii, Colocasia formosan, Colocasia gaoligongensis, Colocasia gigantean, Colocasia gongii, Colocasia gracilis, Colocasia heterochroma, Colocasia humilis, Colocasia konishii, Colocasia latifolia, Colocasia lihengiae, Colocasia macrorrhiza, Colocasia mannii, Colocasia marchalii, Colocasia menglaensis, Colocasia neocaledonica, Colocasia obtusiloba, Colocasia oresbia, Colocasia rapiformis, Colocasia tibetensis* and *Colocasia yunnanensis*.

Non-limiting members of the genus *Xanthosoma*, which may provide a source for the antimetastatic compositions include plants commonly referred to as Yautia, Malanga Blanca, Tannia, Cocoyam, Eddo, Coco, Sato-imo, Japanese Potato, Macabo, Taioba, Dasheen, Quequisque, Ape and Tannier and include species, such as, for example, *Xanthosoma sagittifolium, Xanthosoma atrovirens, Xanthosoma violaceum, Xanthosoma maffaffa, Xanthosoma weeksii, Xanthosoma roseum, Xanthosoma daguense, Xanthosoma poeppigii, Xanthosoma hastifolia, Xanthosoma robusturn, Xanthosoma caracu, Xanthosoma wendlandii, Xanthosoma pichinchense, Xanthosoma hannoniae, Xanthosoma nigrum, Xanthosoma lindenii, Xanthosoma narinoense, Xanthosoma eggersii* and *Xanthosoma yucatanensis*.

In some embodiments, the extract or isolated polypeptide is made by a process comprising obtaining the uncooked root, such as Taro, Malanga or Yautia, peeling the corm, combining it with an aqueous solution (such as PBS); blending the corm to liquefy it, centrifuging (e.g., at 1200 rpm for 15 min at 4° C.) the liquid to obtain a supernatant, centrifuging at high speed (e.g., at 15,000 rpm for 20 min at 4° C.) the supernatant and filter sterilizing to obtain a stock water soluble extract. In some embodiments, the stock water soluble extract has a protein concentration of about 1-5 mg/ml.

In some embodiments, the stock water soluble extract can be further purified by various techniques that are known in the art, including centrifugation, size exclusion chromatography, ion exchange chromatography, reversed phase liquid chromatography, reversed phase high performance liquid chromatography, and a combination of these approaches, to yield a more purified or substantially pure active agent.

In some embodiments, the stock extract can be centrifuged through molecular weight limit devices (such as, for example, Amicon Ultra 10 K (10,000) Nominal Molecular Weight Limit (NMWL) devices (Millipore Corporation) at 4000 g for 45 min at 25° C). The upper fraction which contains the antimetastatic activity can (high molecular weight fraction) be filter sterilized (e.g., using a 0.2 μm filter).

In some embodiments, the stock extract can be further purified using size exclusion chromatography (SEC). For example, preparative SEC can be performed on a Biosuite 250, 13μ, 21.5×300 mm column (Waters Corp., Milford. Mass.) using Dulbecco's phosphate buffered saline with calcium and magnesium, at a flow rate of 2 ml/min. 0.5 min. fractions can be collected and tubes can be pooled based on UV absorbance at 220 nm. The antimetastatic activity resides in an approximately 30 kD fraction (calibrated using BSA and carbonic anhydrase globular protein).

In some embodiments, the 30 KD fraction from size exclusion chromatography can be further purified by ion exchange chromatography. Preparative anion exchange chromatography can be carried out using standard techniques (e.g., on an HQ/20, 10×100 mm column (Applied Biosystems, Foster City, Calif.), using a 30 minute gradient of 0-30% B at a flow rate of 5 ml/min.: Buffer A=50 mM Tris, pH 8.0, Buffer B=50 mM Tris pH 8+1.0 M NaCl. 0.5 min. fractions were collected and tubes were pooled based on UV absorbance at 220 nm). Pooled samples can be concentrated (e.g., using Centricon Plus 70 10 K Nominal Molecular Weight Limit (NMWL) devices (Millipore) and buffer exchange can be done using Zeba Desalt Spin Columns, Pirece Protein Research Product (Thermo Scientific)).

In some embodiments, the active fraction obtained from ion exchange chromatography can be further purified using reversed phase chromatography (RPLC). Analytical RPLC can be done using standard techniques and equipment (e.g., using a Jupiter C5 300 Å column (Phenomenex, Torrance, Calif.), employing a 40 minute gradient of 1-100% B at 1 ml/min. Buffer A=0.1% trifluoroacetic acid (TFA) in water, Buffer B=0.1% TFA in water: acetonitrile (20:80), with UV detection at 215 nm using a Beckman Coulter HPLC systems with System Gold V8 or 32 Karat software packages).

In some embodiments, additional purification of isolated proteins can be accomplished using reversed phase high performance liquid chromatography using standard techniques and equipment (e.g., on a Waters 2695 HPLC system; absorbance can be monitored with an Applied Biosystems 785 UV detector at 214 nm; proteins can be separated, e.g., on a Waters Symmetry 300 3µ C4 1 mm×150 mm column with a gradient of 0.1% trifluoroacetic acid (TFA) in water (solvent A) and 0.09% TFA in acetonitrile (solvent B)).

In some embodiments, the isolated polypeptide having antimetastatic activity can be produced recombinantly using standard techniques well known in the art.

In some embodiments, the invention provides pharmaceutical compositions having antimetastatic activity, comprising a soluble extract or one or more isolated polypeptides from a plant of a genus selected from the group consisting of *Colocasia* and *Xanthosoma*. In some embodiments, the plant is Taro (*Colocasia esculenta*), Malanga Blanca (*Xanthosoma sagittifolium*), Yautia (*Xanthosoma sagittifolium*), and combinations thereof.

In some embodiments, the invention provides pharmaceutical compositions having antimetastatic activity, comprising a polypeptide from *Colocasia*, such as Taro (*Colocasia esculenta*), wherein the polypeptide comprises an amino acid sequence selected from the group consisting of SEQ ID NO:1, SEQ ID NO:2 and a combination thereof, wherein the polypeptide has an approximate molecular weight of 30 KD based on size exclusion chromatography.

In some embodiments, the invention provides pharmaceutical compositions having antimetastatic activity, comprising a polypeptide from *Xanthosoma*, such as Malanga Blanca or Yautia (*Xanthosoma sagittifolium*), wherein the polypeptide comprises an amino acid sequence selected from the group consisting of SEQ ID NO:3, SEQ ID NO:4 and a combination thereof wherein the polypeptide has an approximate molecular weight of 30 KD based on size exclusion chromatography.

By the term "therapeutically effective amount" is meant an amount that produces the desired effect for which it is administered. The exact amount will depend on the purpose of the treatment, the subject to be treated, and will be ascertainable by a person skilled in the art using known methods and techniques for determining effective doses. In some embodiments, the amount of a stock water soluble extract that can be administered includes between about 0.1 mg/kg/day to about 200 mg/kg/day. In some embodiments, the amount of purified polypeptide that can be administered includes between about 1.0 µg/kg/day to about 50 mg/kg/day.

A therapeutically effective amount of the polypeptide(s) can be combined with any pharmaceutically and/or physiologically acceptable carrier, such as aqueous solutions, salts, buffers, stabilizers, solubilizers, fillers, diluents, and other known substances, depending on the route of administration. The compositions may be prepared in any of a variety of forms suitable for the desired mode of administration. For example, pharmaceutical compositions may be prepared in the form of tablets, powders, lozenges, elixirs, suspensions, emulsions, solutions, syrups, aerosols (as solids or in liquid media), soft-gel and hard-gel capsules, suppositories, sterile injectable solutions, sterile packaged powders, and the like. Similarly, the carrier or diluent may include time-delay or time-release material known in the art. Proper formulation is dependent upon the route of administration chosen. For injection, the agents of the invention can be formulated into aqueous solutions, preferably in physiologically compatible buffers such as Hank's solution, Ringer's solution, or physiological saline buffer. For transmucosal administration, penetrants appropriate to the barrier to be permeated are used in the formulation. The peptides can be formulated for parenteral administration by injection, e.g., by bolus injection or continuous infusion. Formulations for injection can be presented in unit-dosage form, e.g., in ampoules or in multi-dose containers, and can include an added preservative. The compositions can take such forms as suspensions, solutions or emulsions in oily or aqueous vehicles, and can contain formulatory agents such as suspending, stabilizing and/or dispersing agents. See Remington's Pharmaceutical Sciences, 18$^{th}$ Edition, Mack Publishing Co. (1990), which is incorporated in its entirety herein by reference, for a list of formulations.

The pharmaceutical composition can be adapted for administration by any appropriate route, for example by the oral, rectal, nasal, topical, vaginal or parenteral routes. Other routes, e.g., intra-articular, can also be used. Such compositions can be prepared by any known method, for example by admixing the active ingredient with the carrier(s) or excipient(s) under sterile conditions.

Pharmaceutical compositions adapted for parenteral administration can include aqueous and non-aqueous sterile injection solutions which can contain anti-oxidants, buffers, bacteriostats, and solutes which can render the formulation substantially isotonic with the blood of the intended recipient; and aqueous and non-aqueous sterile suspensions which can include suspending agents and thickening agents. Excipients which can be used for injectable solutions include water, alcohols, polyols, glycerine and vegetable oils, for example. The compositions can be presented in unit-dose or multi-dose containers, for example sealed ampoules and vials, and may be stored in freeze-dried conditions requiring only the addition of a sterile liquid immediately prior to use. Extemporaneous injection solutions and suspensions can be prepared from sterile powders, granules, and tablets. The pharmaceutical compositions can contain preserving agents, solubilizing agents, stabilizing agents, wetting agents, emulsifiers, sweeteners, colorants, salts, buffers, antioxidants, etc.

The antimetastatic polypeptides of the invention can be isolated from *Colocasia*, such as Taro (*Colocasia esculenta*), or *Xanthosoma*, such as Malanga Blanca or Yautia (*Xanthosoma sagittifolium*) using biochemical techniques that are well known in the art, such as size exclusion chromatography, ion exchange chromatography and reversed phase liquid chromatography, high performance liquid chromatography or a combination of these approaches. In some embodiments, the polypeptides can be produced using recombinant methods.

In another aspect, the invention relates to an isolated polypeptide from *Colocasia*, such as Taro (*Colocasia esculenta*), having antimetastatic activity when administered, wherein the isolated polypeptide comprises an amino acid sequence selected from the group consisting of SEQ ID NO:1, SEQ NO:2 and a combination thereof, wherein the isolated polypeptide has an approximate molecular weight of 30 KD based on size exclusion chromatography.

In another aspect, the invention relates to an isolated polypeptide from *Colocasia*, such as Taro (*Colocasia esculenta*), having antimetastatic activity when administered, wherein the isolated polypeptide comprises an amino acid sequence selected from the group consisting of SEQ ID NO: 1, SEQ ID NO:2 and a combination thereof, wherein the polypeptide is isolated by a process selected from the group consisting of size exclusion chromatography, ion exchange chromatography, reversed phase liquid chromatography and combinations thereof.

In another aspect, the invention relates to an isolated polypeptide from *Xanthosoma*, such as Malanga Blanca or Yautia (*Xanthosoma sagittifolium*), having antimetastatic activity when administered, wherein the isolated polypeptide comprises an amino acid sequence selected from the group consisting of SEQ ID NO:3, SEQ ID NO:4 and a combination thereof wherein the isolated polypeptide has an approximate molecular weight of 30 KD based on size exclusion chromatography.

The invention is also directed to compositions comprising a combination of antimetastatic polypeptides from *Colocasia*, such as Taro (*Colocasia esculenta*), or *Xanthosoma*, such as Malanga Blanca or Yautia (*Xanthosoma sagittifolium*) as described herein.

The invention also provides methods of treating cancer by inhibiting metastasis in a subject in need thereof; comprising administering a therapeutically effective amount of a water soluble extract or isolated polypeptide to the subject, wherein the extract or polypeptide is from a plant genus selected from the group consisting of *Colocasia*, such as Taro (*Colocasia esculenta*), *Xanthosoma*, such as Malanga Blanca or Yautia (*Xanthosoma sagittifolium*), and combinations thereof. In some embodiments, the plant is Taro (*Colocasia esculenta*), Malanga Blanca (*Xanthosoma sagittifolium*) or Yautia (*Xanthosoma sagittifolium*).

The invention further provides methods of treating cancer by inhibiting metastasis in a subject in need thereof, comprising administering to the subject a composition comprising a therapeutically effective amount of an isolated polypeptide from *Colocasia*, such as Taro (*Colocasia esculenta*), wherein the isolated polypeptide comprises an amino acid sequence selected from the group consisting of SEQ ID NO: 1, SEQ ID NO:2 and a combination thereof, wherein the isolated polypeptide sequence has an approximate molecular weight of 30 KD based on size exclusion chromatography.

The invention further provides methods of treating cancer in a subject in need thereof, comprising administering to the subject a composition comprising a therapeutically effective amount of an isolated polypeptide from *Xanthosoma*, such as Malanga Blanca or Yautia (*Xanthosoma sagittifolium*), wherein the isolated polypeptide comprises an amino acid sequence selected from the group consisting of SEQ ID NO: 3, SEQ ID NO:4 and a combination thereof, wherein the isolated polypeptide sequence has an approximate molecular weight of 30 KD based on size exclusion chromatography.

The invention further provides compositions to inhibit cyclooxygenase (COX) activity, for example, for use in treating inflammatory diseases or conditions. Exemplary inflammatory diseases or conditions include, for example, arthritis, osteoarthritis, rheumatoid arthritis, autoimmune diseases or inflammatory diseases. Other exemplary inflammatory conditions or diseases include, for example, tendonitis, ligamentitis and traumatic joint injury, inflammatory immune disorders, including but not limited to rheumatic diseases, allergic disorders, asthma, allergic rhinitis, skin disorders, gastrointestinal disorders such as Crohn's disease and ulcerative colitis, transplant rejection, poststreptococcal and autiommune renal failure, septic shock, systemic inflammatory response syndrome (SIRS), adult respiratory distress syndrome (ARDS) and envenomation.

In some embodiments, the invention provides methods of inhibiting cyclooxygenase (COX) activity in a subject in need thereof, comprising administering to the subject a composition comprising a therapeutically effective amount of an active agent isolated from *Colocasia*. In some aspects, an inflammatory disease or condition is treated by inhibiting cyclooxygenase (COX) activity. In some embodiments, the cyclooxygenase (COX) activity that is inhibited is selected from the group consisting of COX-1, COX-2 and COX-3 activity. In some embodiments, COX-2 mRNA expression is inhibited. In some embodiments, the composition comprises a water soluble extract from Taro (*Colocasia esculenta*).

EXAMPLES

Example 1

Taro Extract (TE) Preparation

Commercially obtained Taro corm was peeled, combined with PBS in a weight:volume ratio of 1:3, blended at low speed, followed by high speed to liquefy. After centrifugation at 1200 r.p.m. for 15 min at 4° C., the supernatant was subjected to high speed centrifugation (15,000 r.p.m. for 20 min at 4° C.) and filter sterilized. The protein concentration of the stock taro extract (TE) was determined from multiple preparations of the extract using Coomassie Plus Protein Assay Reagent (Pierce) and ranged from 1.69 mg/ml to 3.43 mg/ml. For the following experiments, stock TE of 2 µg/µl protein was used, unless otherwise indicated.

Example 2

Effect of TE on Cell Morphology and Cell Proliferation

We examined the effect of TE on the morphology and proliferation of a panel of murine (66.1, 410.4) and human (MCF-7, MDA-MB-231, MDA-MB-435 and T47D) breast cancer cell lines, human prostate cancer cell lines (DU145, LNCaP, PC3) and immortalized murine mammary (EpH4) and human mammary (MCF10A) epithelial cell lines.

Effect of TE on Cell Morphology

Procedure: $1 \times 10^6$ cells of each line was seeded in 4.0 ml media. Either 25, 50 or 100 µl of extract or PBS was added to cells and morphology was examined at 48 hours (FIG. 2a-2d) and summarized in Table 1.

TABLE 1

| Effect of TE on cellular morphology | | |
|---|---|---|
| Cell Line | Cell Type | Morphology Change |
| EpH4 | Murine mammary epithelial cell line | No |
| 66.1 | Murine breast cancer cell line | Yes |
| 410.4 | Murine breast cancer cell line | No |
| MCF10A | Human breast epithelial cell line | No |
| MCF-7 | Human breast cancer cell line | Yes |

TABLE 1-continued

Effect of TE on cellular morphology

| Cell Line | Cell Type | Morphology Change |
|---|---|---|
| MDA-MB-231 | Human breast cancer cell line | No |
| DU145 | Human prostate cancer cell line | No |
| LNCAP | Human prostate cancer cell line | Yes |
| PC-3 | Human prostate cancer cell line | No |

Figure 1:
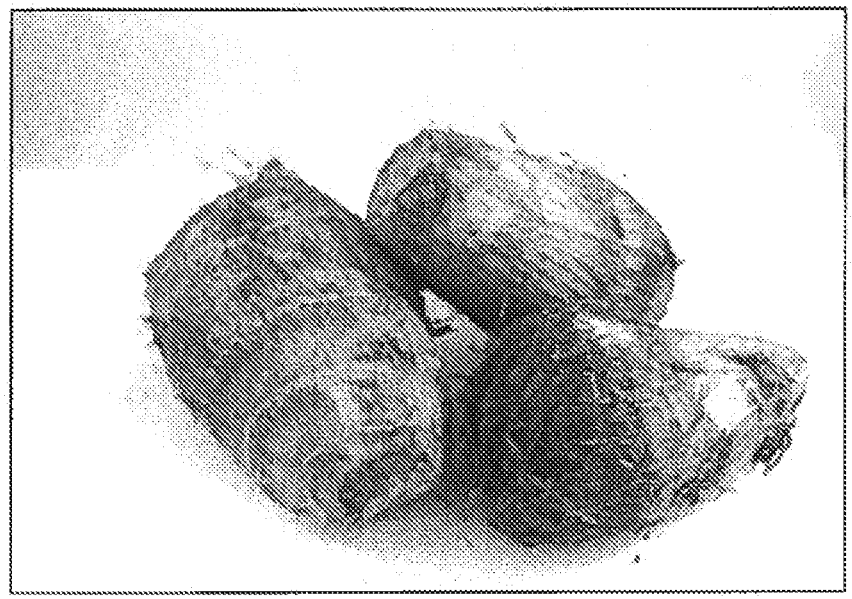
FIG. 1. Photo of Taro corm (Alternate names of Taro: Arvi, Eddo, Dasheen, Kalo, Cheppan Kizhange, Chama dumpa).
Figure 2A:
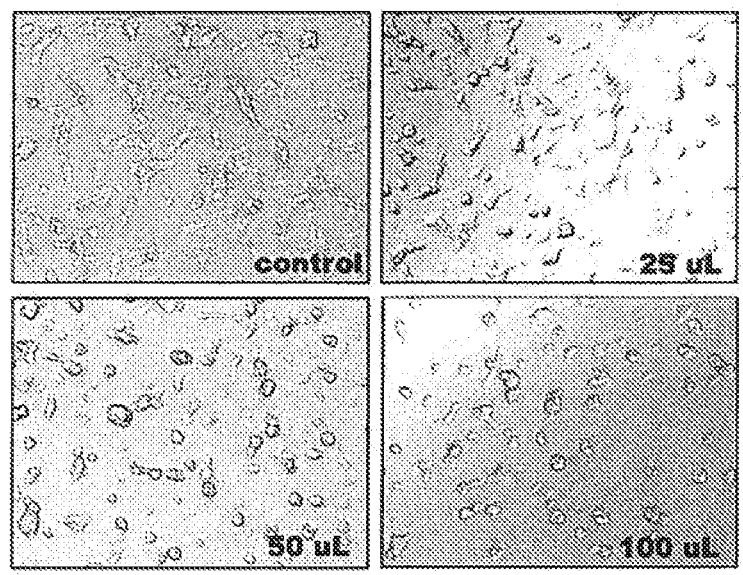
FIG. 2. (A-D). The effect of Taro extract (TE) on morphologic appearance of four cell lines. $1\times10^6$ of each line was seeded in 4.0 ml media. Either 25, 50 or 100 μl of extract or PBS was added to cells and morphology was examined at 48 hours.
Figure 2B:
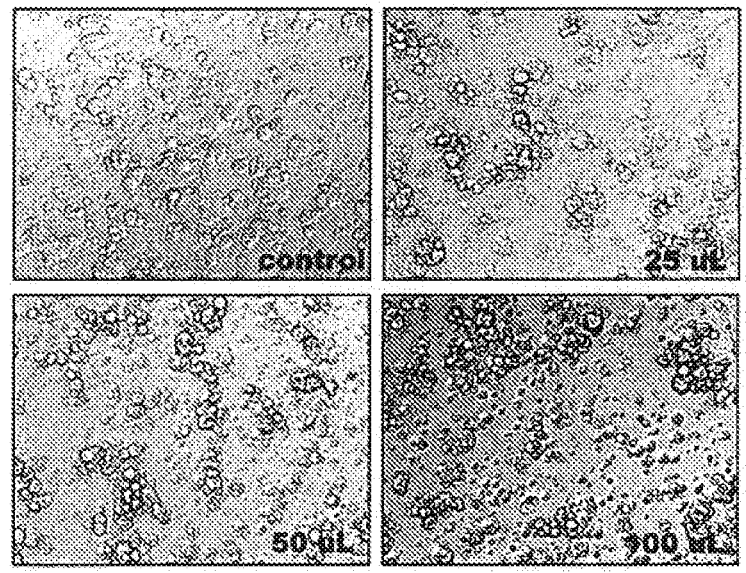
Figure 2C:
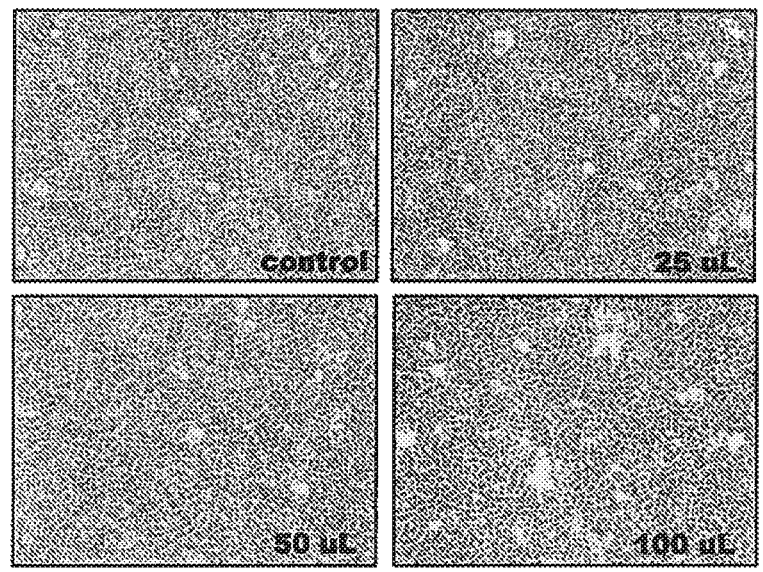
Figure 2D:
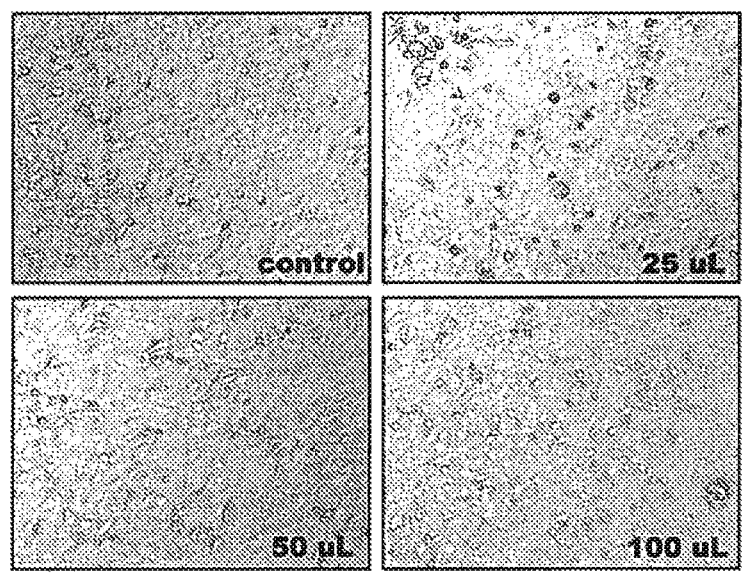

Results: TE profoundly affected the morphology of some (66.1, MCF-7, LNCAP) but not all tumor cells resulting in the retraction of cellular foot processes and cell rounding (Table 1). FIGS. 2a and 2b show that the morphology of malignant breast cell lines 66.1. (murine) and MCF-7 (human) were profoundly affected by the addition of TE in a dose-dependent manner, whereas the appearance of immortalized normal mammary epithelial cell lines MCF10A (Human) and EpH4 (murine) remained unchanged even at the highest concentration of TE (FIG. 2c, 2d).

TE Inhibits Cell Proliferation

Procedure: Line EpH4, 66.1 or MCF-7 (FIG. 3a) cells were seeded at $2.5 \times 10^5$ cells/well/1.0 ml media in 24 well plates and PBS or TE (6.25, 12.5, 25 µl) was added. 48 hrs later, cell number was determined (Kundu, N., Zhang, S. and Fulton, A. M. Sublethal oxidative stress inhibits tumor cell adhesion and enhances experimental metastasis of murine mammary carcinoma. Clin. Exp. Metastasis. 13:16-22, 1995).

Figure 3A:
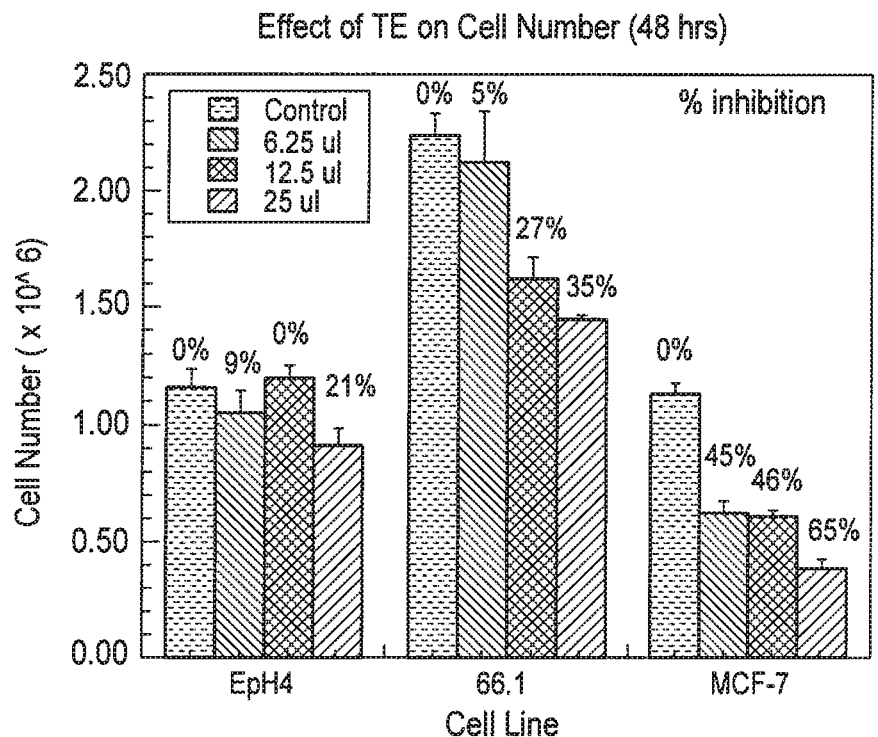
FIG. 3. (A-B). Line EpH4, 66.1 or MCF-7 cells (FIG. 3a) were seeded at $2.5\times10^5$ cells/well/1.0 ml media in 24 well plates and PBS or TE (6.25, 12.5, 25 μl) was added. 48 hrs later, cell number was determined by trypan blue staining. Line 410.4, MCF 10A or MDA-MB-231 cells (FIG. 3b) were seeded at $1.0\times10^5$ cells/well/1.0 ml media in 24 well plates and PBS or TE (6.25, 12.5, 25 μl) was added. 48 hrs later, cell growth was assessed by MTT assay.
Figure 3B:
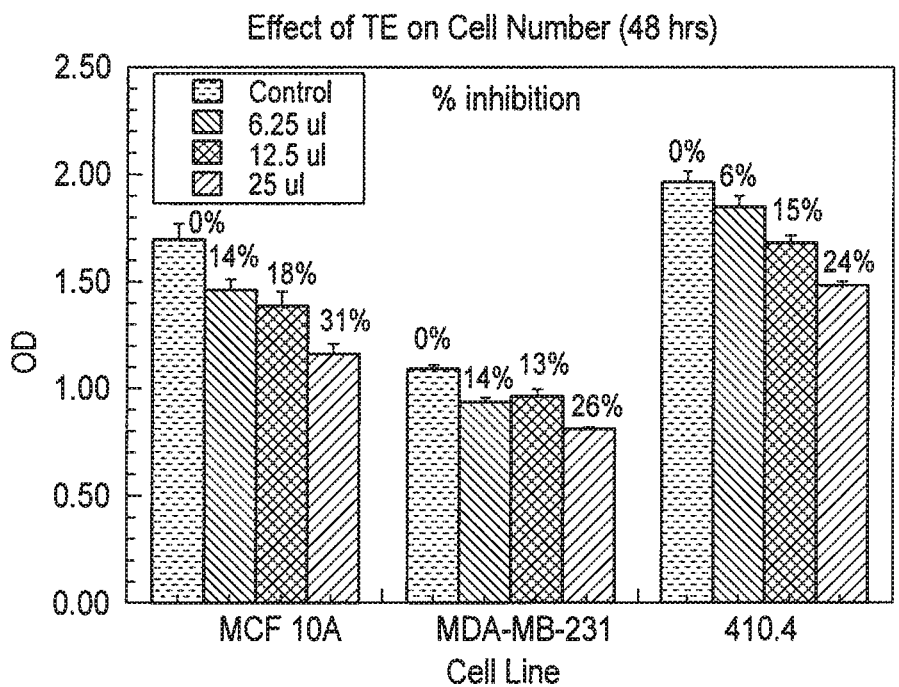

Line 410.4, MCF 10A or MDA-MB-231 cells (FIG. 3b) were seeded at $1.0 \times 10^5$ cells/well/1.0 ml media in 24 well plates and PBS or TE (6.25, 12.5, 25 µl) was added. 48 hrs later, cell growth was assessed by MTT assay (Kundu, N., Smyth, M. J., Samsel, L. and Fulton, A. M. Cyclooxygenase inhibitors block cell growth, increase ceramide and inhibit cell cycle. Breast Cancer Research and Treatment 76:57-64, 2002), Results: TE inhibited cell number of murine mammary tumor cell line 66.1 (FIG. 3a) and 410.4 (FIG. 3b) in a dose dependent manner. At the highest TE concentration, an inhibitory effect on immortalized murine mammary epithelial cell line EpH4 was also observed (FIG. 3a).

In case of human cell lines, TE inhibited cell number of human breast cancer cell lines MCF-7 (FIG. 3a) and also reduced the growth of both MDA-MB-231 (FIG. 3b) as well as breast epithelial cell line MCF10A (FIG. 3b) in a dose dependent manner.

The observation that some, but not all, cells were adversely affected by TE, suggests that the antiproliferative effects of TE are not likely to be due to nonspecific toxicity.

The Effect of TE on Cell Proliferation is Reversible

Figure 4:
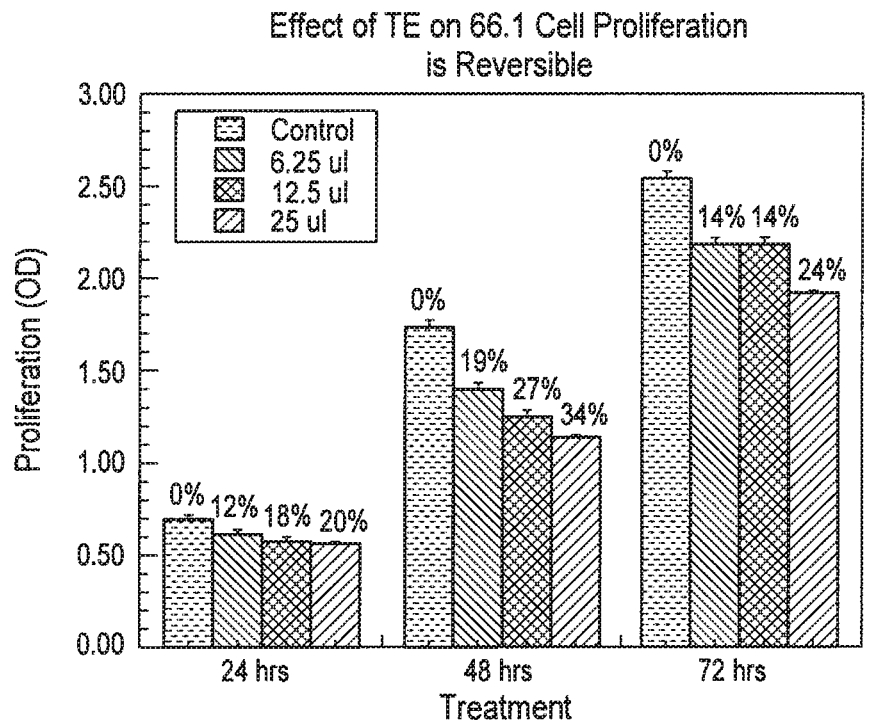
FIG. 4. Line 66.1 cells were seeded $1.0\times10^5$ cells/well/1.0 ml media in 24 well plates. PBS or TE was added as indicated, 24, 48 and 72 hrs later cell growth was assessed by MTT assay.

Procedure: To determine if TE induces an irreversible effect on breast cancer cells, cell growth was assessed at several time points following the addition of TE. Line 66.1 cells were seeded $1.0 \times 10^5$ cells/well/1.0 ml media in 24 well plates. PBS or TE was added as indicated, 24, 48 and 72 hrs later cell growth was assessed by MTT assay (FIG. 4) (Kundu, N., Smyth, M. S., Samsel, L. and Fulton, A. M. Cyclooxygenase inhibitors block cell growth, increase ceramide and inhibit cell cycle. Breast Cancer Research and Treatment 76:57-64, 2002).

Results: TE had an inhibitory effect on 66.1 cell proliferation which was most pronounced after 48 hrs of treatment. At 72 hrs post treatment, proliferation of 66.1 cells was returning to that of cells treated with vehicle indicating that the effect of TE is reversible.

Example 3

Preliminary Characterization of TE

TE Activity is Not Due to Endotoxin

Polymyxin B treatment of the TE did not reduce the antiproliferative activity indicating that this activity is not due to endotoxin contamination.

TE Activity is Heat Sensitive and Precipitates with Trichoroacetic Acid

When TE stock was placed in a boiling water bath for 10 minutes, the ability to affect cell morphology and proliferation was lost. Likewise, TE activity was completely lost when taro extract was prepared from cooked taro following the same protocol as described in Example 1. Antiproliferative activity was largely lost from the soluble supernatant fluid after TE was treated with TCA.

Example 4

Effect of TE on Cell Cycle Progression

Purpose: Since TE affected cell proliferation and cell morphology, we wanted to find out if TE affects cell cycle progression.

Procedure: To determine if TE affects cell cycle progression, $3 \times 10^6$ line 66.1 or MCF7 cells were seeded in 4.0 ml media. PBS or TE was added to achieve final concentration as indicated. 24 hours later cells were permeabilized, treated with RNaseA and reacted with propidium iodide. DNA content was determined by FACScan analysis (Table 2) (Kundu, N., Smyth, M. J., Samsel, L. and Fulton, A. M. Cyclooxygenase inhibitors block cell growth, increase ceramide and inhibit cell cycle, Breast Cancer Research and Treatment 76:57-64, 2002).

TABLE 2

Effect of TE on cell cycle progression Treatment (24 hrs)

| Treatment | G0/G1(%)l | S(%) | G2-M |
|---|---|---|---|
| 66.1 cells | | | |
| PBS | 48.6 | 43.9 | 7.5 |
| TE - 12.5 µl/ml | 54.2 | 39.5 | 6.3 |
| TE - 25 µl/ml | 56.5 | 38.0 | 5.5 |
| MCF7 cells | | | |
| PBS | 28.6 | 65.5 | 5.9 |
| TE - 12.5 µl/ml | 35.4 | 60.7 | 3.9 |
| TE - 25 µl/ml | 35.3 | 60.5 | 4.2 |

Results: TE caused cell cycle arrest of both 66.1 and MCF7 cells at both concentrations of TE. A greater proportion of TE-treated 66.1 cells were in G0/G1 phase of the cell cycle and fewer were in the S-phase fraction in comparison to PBS-treated cells. Likewise, TE treatment inhibited cell-cycle progression in MCF7 cells (more cells in G0/G1 and fewer in S phase).

Example 5

Effect of TE on Prostaglandin $E_2$ ($PGE_2$) Production

Purpose: Increased prostaglandin production is a very common feature in human malignancies. It has been shown that $PGE_2$ levels are positively correlated with increased tumorigenic and metastatic potential. We asked if TE has any effect on $PGE_2$ production.

Figure 5:
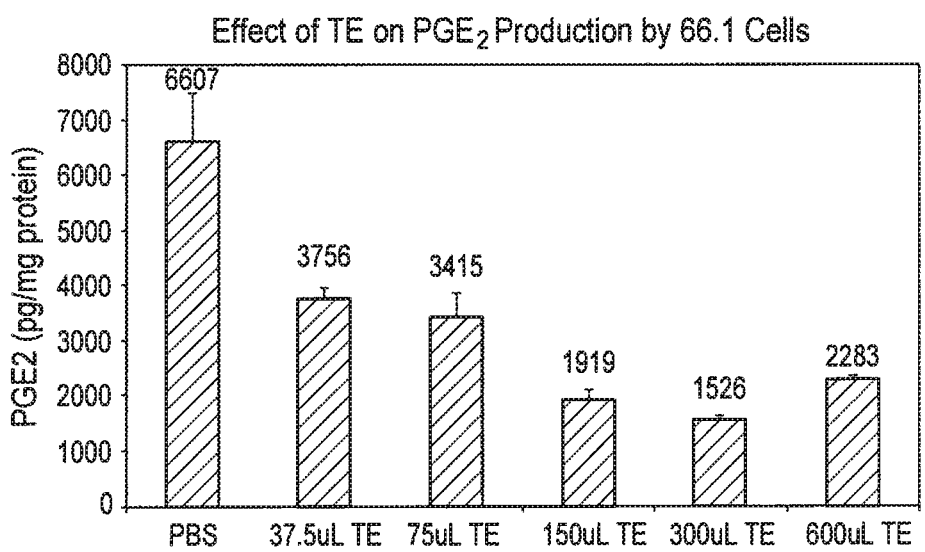
FIG. 5. The effect of TE on $PGE_2$ production by the line 66.1. $6\times10^6$ line 66.1 cells were seeded in 12 ml media. PBS or TE was added in the indicated amount. 24 hours later media was collected and PGE2 level was determined by Enzyme Immuno Assay.
Figure 6:
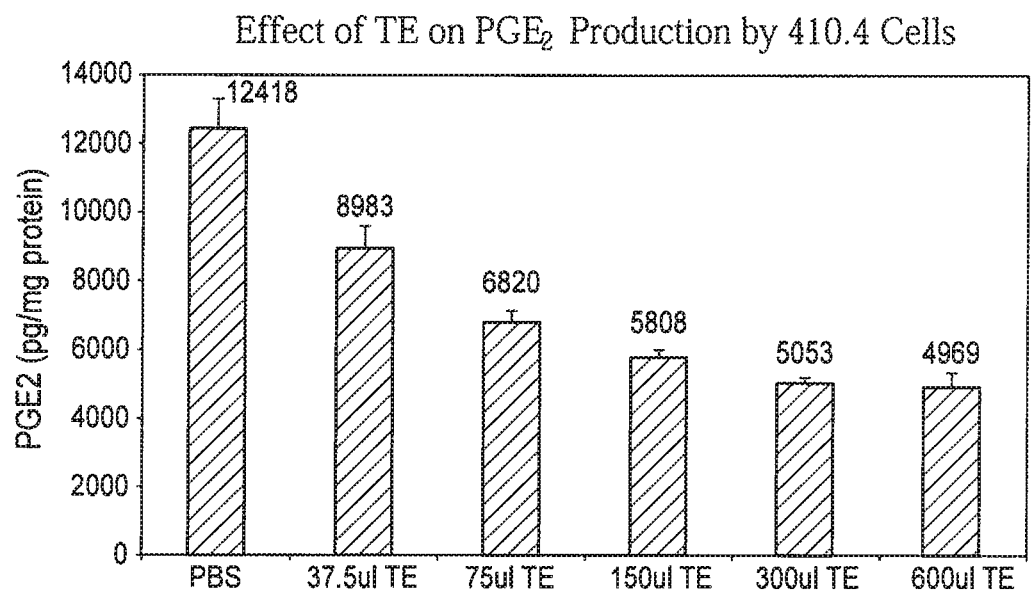
FIG. 6. The effect of TE on $PGE_2$ production by the line 410.4. $6\times10^6$ of line 410.4 cells were seeded in 12 ml media. PBS or TE was added in the indicated amount. 24 hours later media was collected and PGE2 level was determined by Enzyme Immuno Assay.

Procedure: To determine if TE affects $PGE_2$ production, $6\times10^6$ line 66.1 or 410.4 cells were seeded in 12 ml media. PBS or TE was added as indicated amount. 24 hours later media was collected and $PGE_2$ level was determined by Enzyme Immuno Assay (FIGS. 5 and 6).

Results: TE inhibits $PGE_2$ production significantly in both cell lines in a dose dependent manner.

Example 6

Effect of TE on COX-2 mRNA Expression

Purpose: $PGE_2$ production is mediated by two different cyclooxygenase (COX) enzymes, COX-1 and COX-2. In several models, inhibition of COX-2 enzyme activity results in less tumor growth and metastasis.

Figure 7:
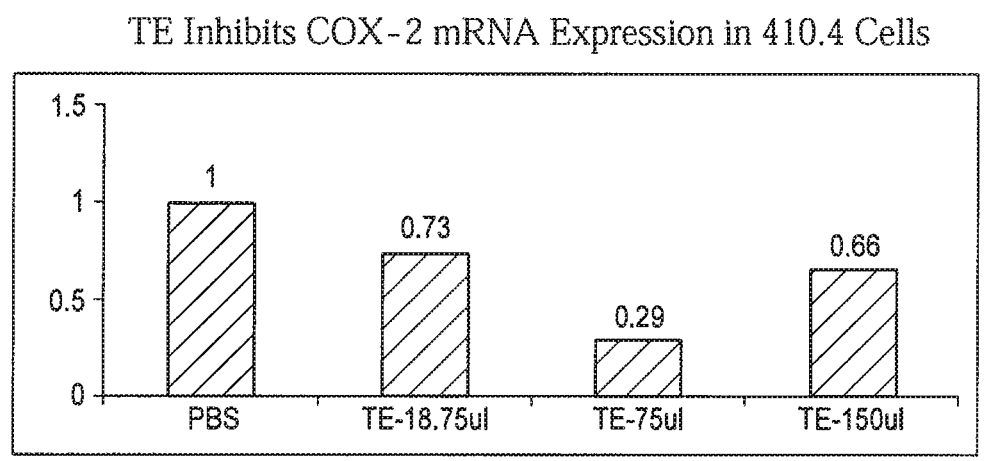
FIG. 7. $6\times10^6$ line 410.4 cells were seeded in 12 ml media. 24 hrs later PBS or TE was added at the indicated amount. Six hours later COX-2 mRNA expression levels were determined by quantitative RT-PCR.

Procedure: To find out if TE affects COX-2 mRNA expression, $6\times10^6$ line 410.4 cells were seeded in 12 ml media. 24 hrs later PBS or TE was added at the indicated amount. Six hours later COX-2 mRNA expression levels were determined by quantitative RT-PCR (FIG. 7).

Results: TE treatment inhibits COX-2 mRNA expression in 410.4 cell line.

Example 7

Effect of TE on Lung Colonization

Purpose: The effect of TE on cell proliferation and morphology led us to determine if TE could affect breast cancer metastasis. We prepared an aqueous extract of the homogenized raw taro corm, a high-speed supernatant was filter sterilized and protein concentration was adjusted to 2 µg/µl. We first examined the effect of TE on lung colonizing ability of highly metastatic breast cancer cell lines 66.1 and 410.4; the latter forms colonies in both the lung and the heart after i.v. administration. PBS or TE was injected i.p. into Balb/cByJ female mice on days 1-10. On day 4, either 66.1 or 410.4 tumor cells were injected into the lateral tail vein. Between days 16-21 post tumor cell injection, when control animals became moribund, mice were euthanized and surface lung tumor colonies were counted under a dissecting microscope. In all experiments, TE profoundly inhibited the ability of tumor cells to colonize the lungs. TE treatment resulted in a 98-99% reduction in lung tumor colony formation by either tumor cell line. In the case of 410.4, TE also significantly inhibited tumor colonies in the heart. In two experiments, tumor colonies were detected in the hearts of 4/5 and 5/9 control mice, whereas none (0/5) and only 1/10 TE-treated mice showed heart involvement.

Procedure: 150 µl PBS or TE (Table 3a) and 200 µl PBS or TE (Table 3b) was injected i.p. on days 1-4 into syngeneic Balb/cByJ female mice. On day 4, $1\times10^5$ line 66.1 or 410.4 tumor cells were injected into the lateral tail vein. Treatment with PBS or TE continued (200 µl) for an additional 6 days. On day 21 post tumor cell injection, mice were euthanized and surface lung tumor colonies were counted (Kundu, N., Beaty, T. L., Jackson, M. J. and Fulton, A. M. Antimetastatic and antitumor activities of Interleukin 10 in a murine model of breast cancer. J. Natl. Cancer Inst. 88: 536-541. 1996; Ma, X., Kundu, N., Rifat, S., Walser T. and Fulton, A. M. Prostaglandin E receptor EP4 antagonism inhibits breast cancer metastasis. Cancer Res. 66:2923-2927, 2006).

TABLE 3a

Inhibitory effect of TE on lung colonization (66.1 cell line)

| | Experiment 1 | | Experiment 2 | |
|---|---|---|---|---|
| | Control | TE-treated | Control | TE-treated |
| No. of animals | 3 | 5 | 9 | 10 |
| Average Lung tumor colonies (Mean ± SE) | 46.0 ± 16.5 | 0.8 ± 0.6 p = 0.04 | 73.4 ± 13.6 | 0.5 ± 0.3 p = 0.004 |
| Median no. and range of tumor colonies | 49 (16-49) | 0 (0-3) | 86 (0-102) | 0 (0-3) |

TABLE 3b

Inhibitory effect of TE on lung colonization (410.4 cell line)

| | Experiment 1 | | Experiment 2 | |
|---|---|---|---|---|
| | Control | TE-treated | Control | TE-treated |
| No. of animals | 6 | 5 | 10 | 10 |
| Average Lung tumor colonies (Mean ± SE) | 13.3 ± 5.7 | 0.2 ± 0.2 p = 0.015 | 25.4 ± 13.6 | 1.0 ± 0.6 p < 0001 |
| Median no. and range of tumor colonies | 6.5 (2-35) | 0 (0-1) | 23 (15-46) | 0 (0-6) |
| Mice with heart metastasis | 4/6 | 0/5 | 5/10 | 1/10 |

Results: Tables 3a and 3b summarize the effect of TE on lung colonization by 66.1 and 410.4 cell lines, respectively. Each table summarizes the results of two independent experiments, carried out with two independently prepared extracts. Both experiments demonstrate that TE profoundly inhibits the ability of tumor cells to colonize the lungs. TE treatment resulted in a 98-99% reduction in lung tumor colony formation.

Example 8

Effects of TE on Spontaneous Metastasis

Purpose: Knowing that TE inhibits lung colonization resulting from i.v. injections of tumor cells significantly, we wanted to find out if TE has any effect on spontaneous metastasis to the lung from mammary gland implanted tumor cells or on the growth characteristics of the primary tumor.

Procedure: To determine if TE could inhibit spontaneous metastasis or affect tumor expansion, 150 µl PBS or TE was injected daily i.p. for 4 days into syngeneic immune competent Balb/cByJ female mice. On day 4, $5\times10^5$ line 66.1 tumor cells were injected subcutaneously proximal to the mammary gland, 200 µl of either PBS (o - - - o) or TE (o—o) was injected i.p. daily for an additional 6 days. Tumor size was determined by caliper twice per week. Each animal was euthanized when the tumor achieved an average diameter of 18 mm, or earlier if the mouse appeared moribund. Soft tissues were examined for surface tumor colonies (Kundu, N. and Fulton, A. M. Interleukin- 10 inhibits tumor metastasis, down regulates MHC class I and enhances NK lysis. Cellular Immunology 180:55-61, 1997; Walser, T. C., Rifat, S., Ma, X., Kundu, N., Ward, C., Goloubeva, O., Johnson, M. G., Medina, J. C., Collins, T. L. and Fulton, A. M. Antagonism of CXCR3 inhibits lung metastasis in a murine model of metastatic breast cancer. Cancer Res. 66:(15),7701-7707, 2006; Kundu, N. and Fulton, A. M. Selective COX-1 or COX-2 inhibitors control metastatic disease in a murine model of breast cancer. Cancer Res. 62:2343-2346, 2002; Dorsey, R., Kundu, N., Yang, Q., Tannebaum, C. S., Sun, H., Hamilton, T. A. and Fulton, A. M. Immunotherapy with interleukin-10 depends on the CXC chemokines inducible Protein-10 and monokine induced by IFN-g. Cancer Res. 62: 2606-2610, 2002).

Figure 8:
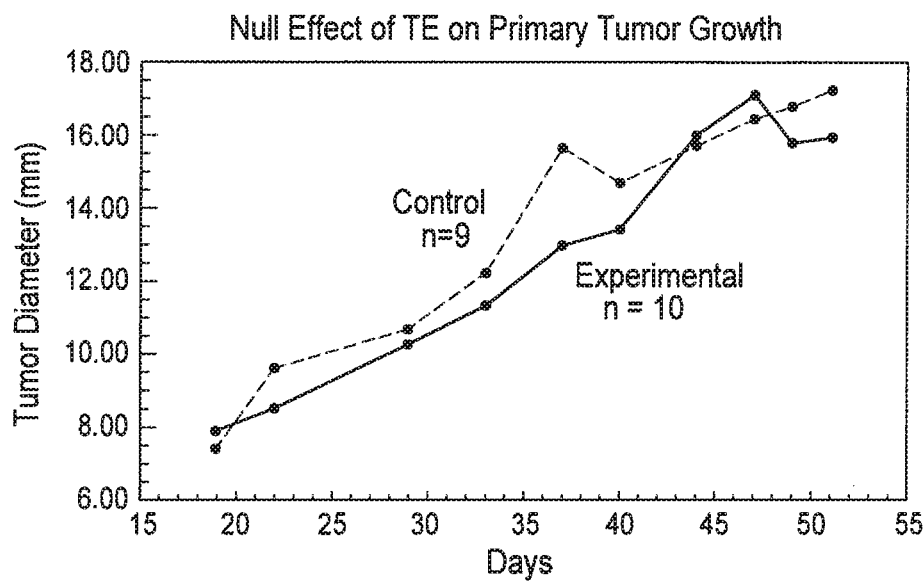
FIG. 8. 150 μl PBS or TE was injected daily i.p. for 4 days into syngeneic immune competent Balb/cByJ female mice. On day 4, $5\times10^5$ line 66.1 tumor cells were injected subcutaneously proximal to the mammary gland. 200 μl of either PBS (o - - - o) or TE (o—o) was injected i.p. daily for an additional 6 days. Tumor size was determined by caliper twice per week. Each animal was euthanized when the tumor achieved an average diameter of 18 mm, or earlier if the mouse appeared moribund. Soft tissues were examined for surface tumor colonies.

Results: Treatment with TE under this protocol did not affect the size of the locally-growing tumor (FIG. 8). In spite of this, spontaneous metastases were reduced in the TE treated mice in comparison to PBS-treated mice. The TE treated group had 6.8±1.7 lung metastases versus 10.5±2.1 in the vehicle-treated group. While this difference was not statistically significant, a trend for decreased spontaneous metastasis was consistent with the significant reduction in lung colonization observed in Tables 3a and 3b. When other metastatic sites are considered, we observed that one of ten TE-treated mice displayed metastases outside the lung, whereas four of ten control mice had extra pulmonary metastases.

Example 9

Effect of TE on Established Tumors

Purpose: We determined the effect of TE on established tumors, a more clinically relevant model.

Procedure: To determine the effect of TE on established tumors, $5 \times 10^5$ line 66.1 tumor cells were injected subcutaneously proximal to the mammary gland of syngeneic immune competent Balb/cByJ female mice. 200 μl of either PBS or TE was injected i.p. daily for 13 days, starting on day 10 when tumors became palpable.

A second experiment was done by injecting $5 \times 10^5$ line 410.4 tumor cells subcutaneously proximal to the mammary gland of syngeneic immune competent Balb/cByJ female mice. 200 μl of either PBS or TE was injected i.p. daily for 18 days, starting on day 5 when tumors became visible. Tumor growth was monitored and the effect of TE on tumor size and spontaneous metastasis was determined in both experiments. When tumors achieved an average diameter of 18 mm, or earlier if animals appeared moribund, mice were euthanized individually and soft tissues examined for spontaneous metastasis. Delaying initiation of TE therapy until tumors are well established still resulted in a significantly reduced number (85% inhibition) of spontaneous lung metastases but had no effect on the size of the locally growing tumors.

Results: Delaying initiation of TE therapy until tumors are well established still resulted in a reduced number of spontaneous lung metastases in both experiments (Table 4). In the first experiment (66.1 cell line) the reduction in number of lung metastases is not statistically significant but in the second experiment using a different cell line (410.4) TE therapy resulted in a significantly reduced number of spontaneous lung metastases but TE had no impact on the size of the primary tumor.

Example 10

Effect of TE Treatment on NK-mediated Tumor Cell Lysis

Purpose: It is well known that natural killer (NK) cells play a major role in controlling metastasis. We wanted to find out if TE has any effect on the degree of NK-mediated lysis of tumor cells.

Procedure: To determine if the ability of NK cells to lyse tumor cells is affected by TE, 200 μl either PBS or TE was injected per mouse per day i.p. 4 days. On day 5 mice were euthanized and spleen cells were isolated. Enriched splenic NK cells were harvested and cytotoxicity was determined using the CytoTox96® Non-Radioactive Cytotoxicity Assay per the manufacturer's protocol (Promega, WI). Target cells (66.1 mammary tumor cells) were added to the experimental wells and enriched splenic NK cells (effector cells) were added to the target cells at 2:1, 5:1 and 10:1 (effector:target) ratio and 18 hours later, degree of tumor cell lysis was determined.

Percent cytotoxicity was calculated using the following formula:

$$\frac{\text{Experimental} - \text{Effector Spontaneous} - \text{Target Spontaneous}}{\text{Target Maximum} - \text{Target Spontaneous}} \times 100$$

Figure 9:
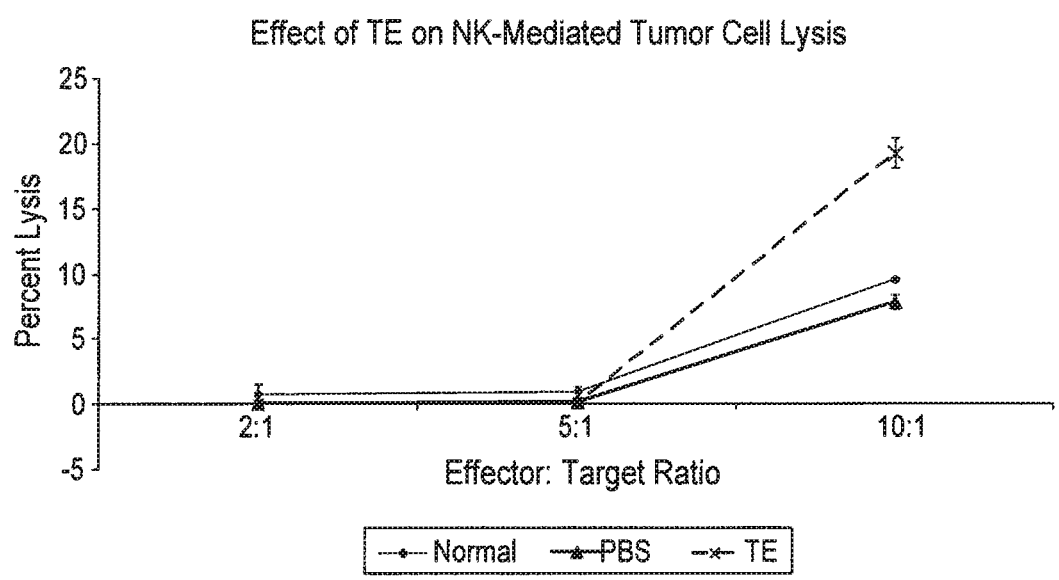
FIG. 9. Enriched splenic NK cells were harvested from TE or PBS treated mice and cytotoxicity was determined using the CytoTox9® Non-Radioactive Cytotoxicity Assay (Promega, WI) per manufacturer's protocol. Target cells (66.1 mammary tumor cells) were added to the experimental wells and enriched splenic NK cells (effector cells) were added to the target cells at 2:1, 5:1 and 10:1 (effector:target) ratio and co-incubated for 18 hours and tumor cell lysis was determined.

Results: For technical reasons, the degree of NK-mediated tumor cell lysis was low in this experiment, however, it can be seen that NK effector cells isolated from TE-treated mice express more lytic activity than NK cells from control mice at the 10:1 effector:target ratio (FIG. 9).

Example 11

Effect of TE Treatment on Body Weight and Organ Weight (4 or 21 Days Treatment)

4 Days Treatment

Purpose: To begin to assess potential toxicity and to understand the mechanism of action, we determined the effect of TE on body and organ weight (Table 5).

Procedure: Normal syngeneic Balb/cByJ female mice were treated i.p. with 200 μl PBS or TE for 4 days. On day 5, mice were euthanized and organ wet weight was determined. Body weight was assessed on day 1 and day 5 and the difference recorded as body weight gain (Table 5).

TABLE 4

Effect of TE on Established Tumors

| | No. of lung metastasis (66.1 cell line) | | No. of lung metastasis (410.4 cell line) |
|---|---|---|---|
| Control (n = 9) Mean ± S.E. | 24.1 ± 4.0 | Control (n = 14) Mean ± S.E. | 31.4 ± 5.5 |
| TE-treated (n = 4) Mean ± S.E. | 15.8 ± 5.5 p = n.s. | TE-treated (n = 10) Mean ± S.E. | 4.7 ± 1.7 p = 0.0012 |

TABLE 5

Effect of TE treatment (4 days) on body and different organs weight

|  | Body wt. gain (gm) Mean ± S.D. | Kidney (mg) Mean ± S.D | Spleen (mg) Mean ± S.D | Liver (mg) Mean ± S.D | Heart (mg) Mean ± S.D | Lung (mg) Mean ± S.D |
|---|---|---|---|---|---|---|
| Control (n = 3) | 0.07 ± 0.44 | 284 ± 21 | 82 ± 10 | 968 ± 165 | 137 ± 26 | 153 ± 27 |
| TE-200 ul (n = 4) | 0.40 ± 0.77 p = n.s. | 305 ± 30 p = n.s. | 186 ± 38 p < 0.007 | 1185 ± 174 p = n.s. | 130 ± 30 p = n.s. | 179 ± 20 p = n.s. |

Results: The gross appearance of whole animal or individual organs was not different in control versus TE-treated mice. Body weight gain was also not significantly different in TE-treated versus control mice (p=0.54). Spleens were significantly heavier in TE-treated mice. P values by unpaired Student T test. In contrast, mice given very high dose TE (686 µg/day) for 2 days exhibited gross signs of toxicity (scruffy fur, redness of the abdomen, data not shown) which was reversed after treatment cessation.

21 Days Treatment

Procedure: In our previous metastasis experiments we have treated the animals with TE for 4 days. To determine if extended treatment with TE would have similar effects on organ or body weights, Balb/cByJ female mice were treated i.p. with 200 µl of PBS or TE for 21 days. Body weight was taken on day 1 and day 22 and the difference recorded as body weight gain (Table 6).

On day 22 mice were euthanized and tissue from liver, kidney, heart, lung and spleen was fixed and examined histologically by a Clinical Pathologist. Although whole body weight gain and organ weights (kidney, spleen, liver) significantly increased in the TE-treated group, no histological abnormality was seen in any major organ with the exception of the spleen where the B cell follicles were enlarged in TE-treated mice.

TABLE 6

Effect of TE treatment (21 days) on body and organ weight

|  | Body wt. gain (gm) | Kidney mg | Spleen mg | Liver mg | Heart mg | Lung mg |
|---|---|---|---|---|---|---|
| Control(n = 3) Mean ± S.D. | 0.9 ± 0.3 | 122 ± 9 | 80 ± 11 | 1263 ± 156 | 113 ± 22 | 239 ± 25 |
| TE-200 ul(n = 3) Mean ± S.D. | 3.1 ± 1.0 p < 0.02 | 145 ± 4 p < 0.02 | 227 ± 26 p < 0.0007 | 1606 ± 119 p < 0.04 | 105 ± 6 p = n.s. | 136 ± 5 p < 0.002 |

Results: The results show that 21 days TE treatment caused increased weight gain of each animal in comparison to PBS treated mice. Control mice gained an average of 0.9 gm whereas TE-treated mice gained an average of 3.1 gms (p<0.02). The gross appearance and behavior of TE-treated mice were not different from PBS-treated mice.

21 days TE treatment of normal Balb/cByJ mice caused the following effects on different organs. TE treatment markedly increased spleen weight. The average weight of liver and kidney were also significantly increased in TE verses PBS-treated mice, whereas lungs weighed significantly less in TE-treated mice. P values by unpaired student T test.

Example 12

Effect of TE Treatment (4 days) on Spleen Cell Phenotypes (% Total)

Purpose: Previous experiments showed that 4 days TE treatment causes splenomegaly. This experiment was done to find out if any cellular components are responsible for splenomegaly.

Procedure: Syngeneic Balb/cByJ female mice were treated i.p. with 200 µl either PBS or TE for 4 or 21 days. On day 5 or 22, mice were euthanized and spleens were harvested for the experiment. Spleen cells from PBS (3 mice) and TE treated (4 mice) were isolated. Whole spleen suspension was treated with RBC lysis buffer and washed twice with PBS. $1 \times 10^6$ cell suspension was taken per tube and fluorescence conjugated antibodies or appropriate isotype control antibody to CD3+ (CD3), CD4+ (CD4), CD8+ (CD8), macrophage (MAC-1), NK (DX5) and myeloid-derive suppressor cells, MDSC (CD11b+GR1) was added. Tubes were incubated for 30 min at 4° C. followed by washing with PBS. Cells were fixed using 500 µl of cold 1% paraformaldehyde and analyzed by FACScan analysis. Results are expressed as the percent of the total spleen cells positive for the individual marker (Table 7a,b) (Walser, T. C., Ma, X., Kundu, N., Dorsey, R., Goloubeva, O. and Fulton, A. M. Immune-mediated Modulation of breast cancer growth and metastasis by the chemokine Mig (CXCL9) in a murine model. J. Immunotherapy 30, 490498, 2007).

TABLE 7a

Effect of TE treatment (4 days) on spleen cell phenotypes (% total)

| | CD3 Mean ± S.D. | CD4 Mean ± S.D. | CD8 Mean ± S.D. | CD19 Mean ± S.D. | DX5 Mean ± S.D. | MAC-1 Mean ± S.D. | MDSC Mean ± S.D. |
|---|---|---|---|---|---|---|---|
| Control (n = 3) | 58.93 ± 5.0 | 39.38 ± 1.0 | 24.08 ± 0.8 | 21.33 ± 0.6 | 3.96 ± 1.3 | 12.76 ± 1.0 | 1.98 ± 0.5 |
| TE-treated (n = 4) | 32.66 ± 6.9 $p < 0.002$ | 20.40 ± 4.5 $p < 0.001$ | 17.30 ± 2.3 $p < 0.005$ | 21.06 ± 0.9 No change | 1.52 ± 0.3 $p < 0.01$ | 13.45 ± 1.8 No change | 4.25 ± 1.2 $p < 0.03$ |

TABLE 7b

Effect of TE treatment (21 days) on spleen cell phenotypes (% total)

| | CD3 Mean | CD4 Mean | CD8 Mean | DX5 Mean. | MAC-1 Mean | MDSC Mean |
|---|---|---|---|---|---|---|
| Control (n = 2) | 55.02 | 31.15 | 21.67 | 1.65 | 9.55 | 2.33 |
| TE-treated (n = 2) | 26.77 | 12.51 | 9.14 | 0.28 | 14.17 | 8.11 |

Results: TE treatment for 4 days shows a lower % of CD3+, CD4+, CD8+ and NK (DX5) cells and higher % of myeloid-derived suppressor cells (MDSC) when compared to PBS-treated mice. The percentage of macrophage and B cells were not different in control vs. TE-treated group (Table 7a). P values by unpaired student T test. Extended treatment with TE for (21 days) also revealed a similar pattern with lower % of CD3+, CD4+, CD8+ and NK (DX5) cells and higher % of myeloid-derived suppressor cells (MDSC). In contrast to the 4 day treatment which did not affect the % of macrophages detected, 21 day treatment resulted in an increase % of macrophages vs. PBS treated mice (Table 7b). Since the spleen increases in size in response to TE, the total number of each cell type was calculated based on the % of each phenotype converted for total spleen cellularity considered based on the spleen weights (Table 8).

19+ cells are modestly increased by TE but none of these changes are statistically significant. Total numbers of B220 and DX5 cells are however, significantly increased in TE treated mice.

Example 13

TE Induces Splenomegaly in Normal Mice and This Effect is Reversible

Purpose: TE treatment causes splenomegaly and we determined if this effect is reversible.

Procedure: Normal mice were injected with TE or PBS (200 μl) daily for 4 days. On day 5 or day 36 three mice from each group were euthanized and spleens were weighed. On day 5, spleens from control mice weighed 85±5 mg versus 181±13 mg in TE-treated mice. On day 32 post TE treatment, spleens from control mice weighed 124±2 mg versus 127±1 mg in TE-treated mice. Total no of each spleen cell population was also determined to find out if there is any

TABLE 8

Effect of TE treatment (4 days) on CD3+, CD4+, CD8+, B and NK cell population in the spleen of normal mice

| | CD3+ Mean ± S.D. | CD4+ Mean ± S.D. | CD8+ Mean ± S.D. | B220 Mean ± S.D. | CD19 Mean ± S.D. | DX5 Mean ± S.D. |
|---|---|---|---|---|---|---|
| Control (n = 3) | 43.2 ± 5.2 | 26.0 ± 2.7 | 16.0 ± 2.0 | 27.8 ± 2.5 | 17.4 ± 1.5 | 3.3 ± 0.2 |
| TE-treated (n = 4) | 50.1 ± 5.8 p = n.s. | 24.5 ± 2.4 p = n.s. | 22.2 ± 2.8 p = n.s. | 42.7 ± 4.5 *p = 0.045 | 22.3 ± 2.3 p = n.s. | 8.8 ± 0.6 *p = 0.0007 |

Total number of each population type = (Mean ± S.D.) × $10^6$
* = <0.05

Results: When absolute number of each population are considered, the total number of CD3+, CD4+, CD8+ and CD difference between control versus TE-treated group on day 32 post TE treatment (Table 9).

TABLE 9

Spleen cell phenotype on day 32 post-TE treatment

| | CD3+ Mean ± S.D. | CD4+ Mean ± S.D. | CD8+ Mean ± S.D. | B220 Mean ± S.D. | CD19 Mean ± S.D. | DX5 Mean ± S.D. |
|---|---|---|---|---|---|---|
| Control (n = 3) | 51 ± 5.1 | 30 ± 3.2 | 19 ± 2.6 | 41 ± 1.5 | 29 ± 2.7 | 5.0 ± 0.3 |

TABLE 9-continued

| | Spleen cell phenotype on day 32 post-TE treatment | | | | | |
|---|---|---|---|---|---|---|
| | CD3+ Mean ± S.D. | CD4+ Mean ± S.D. | CD8+ Mean ± S.D. | B220 Mean ± S.D. | CD19 Mean ± S.D. | DX5 Mean ± S.D. |
| TE-treated (n = 3) | 57 ± 3.4 p = n.s. | 36 ± 1.5 p = n.s. | 20 ± 1.2 p = n.s. | 47 ± 3.0 p = n.s. | 38 ± 2.0 p = n.s. | 6.0 ± 0.3 p = n.s. |

Total number of each population type = (Mean ± S.D.) × $10^6$

Results: These results show that TE per spleen causes splenomegaly during the treatment and the splenomegaly is reversible when the treatment is stopped and spleens return to normal size.

Example 14

TE-Mediated Inhibition of Metastasis Partly Dependent on NK Cells

Purpose: TE-treated spleen showed increased NK cell numbers as well as increased NK-mediated tumor cell lysis in vitro. It is also well known that NK cells play a major role in controlling metastasis. We wanted to determine if NK cells contribute to the ability of TE to inhibit metastasis in vivo.

Procedure: We compared therapeutic activity of TE in normal versus NK-depleted syngeneic Balb/cByJ female mice. 200 μl PBS or TE was injected per mouse per day i.p. for 4 days. On day 4, 1×$10^5$ line 66.1 tumor cells were injected into the lateral tail vein of syngeneic Balb/cByJ female mice. 200 μl of either PBS or TE was injected i.p. daily for an additional 6 days. To deplete NK cells, some animals were treated with asialo GM1 antibody 1 day prior to and 3 days after tumor introduction. On day 21 post tumor cell injection, mice were euthanized and surface lung tumor colonies were counted (Table 10) (Walser, T. C., Rifat, S., Ma, X., Kundu, N., Ward, C., Goloubeva, O., Johnson, M. G., Medina, J. C., Collins, T. L. and Fulton, A. M. Antagonism of CXCR3 inhibits lung metastasis in a murine model of metastatic breast cancer. Cancer Res. 66:(15),7701-7707, 2006; Kundu, N., Walser, T. C., Ma, X. and Fulton, A. M. Cyclooxygenase inhibitors modulate NK activities that control metastatic disease. Cancer Immunol Immunother. 54:981-987, 2005).

TABLE 10

| | Effect of TE on lung colonization in control vs. NK depleted mice | | | |
|---|---|---|---|---|
| | NK-normal Lung metastasis | | NK-depleted Lung metastasis | |
| Animal no. | Control | TE-treated | Control | TE-treated |
| No. of animals | 8 | 10 | 6 | 12 |
| Average lung tumor colonies (Mean ± SE) | 20.3 ± 4.6 | 2.7 ± 1.4 p = 0.003 | 225.0 ± 7.8 | 19.0 ± 3.3 p = 0.004 |
| Median no. and range of tumor colonie | 15 (11-50) | 2(0-10) | 228 (197-245) | 19.5 (2-36) |

Results: Table 10 shows that TE profoundly inhibits lung colonization in mice with normal NK function, reducing the number of tumor colonies by 87% (2.7 versus 20 lung mets), confirming our earlier results. Depletion of NK cells markedly increases the number of lung metastases in PBS-treated mice (225 versus 20) indicating that endogenous NK cells function to control tumor dissemination. TE treatment in NK-depleted animals is still highly effective at reducing lung colonies in comparison to PBS-treated, NK-depleted mice (19 versus 225) indicating that the major mechanism by which TE controls metastasis is likely to be independent of NK cells. It is also possible that the residual NK cells in asialo-GM1 antibody-treated mice contribute to the therapeutic mechanism. Since lung metastases are still higher in TE-treated, NK-depleted mice versus TE-treated, NK-normal mice (p=0.002), a minor role for NK cells may be indicated. Further studies will be necessary to clarify the role of NK cells in TE-mediated inhibition of lung metastasis.

Example 15

TE-Mediated Inhibition of Metastasis is Dependent on T and or B Cells

Purpose: Since B cells were increased in TE-treated spleen, we hypothesized that an immunologic mechanism might contribute to the antimetastatic activity of TE. We wanted to find out if T and or B cells contribute to TE-mediated inhibition of metastasis.

Procedure: We assessed TE efficacy in SCID mice lacking mature T and B cells to examine a role for T or B cells in TE-mediated antimetastatic activity.

TABLE 11

| | TE-mediated inhibition of metastasis is dependent on T and or B cells | | | |
|---|---|---|---|---|
| | Balb/cByJ mice Lung metastasis | | SCID mice Lung metastasis | |
| | Control | TE- treated | Control | TE-treated |
| No. of animals | 9 | 10 | 18 | 15 |
| Average lung tumor colonies (Mean ± SE) | 37.7 ± 9.5 | 0.3 ± 0.2 | 16.9 ± 4.0 | 55.0 ± 5.6 |
| Median no. and range of tumor colonies | 30(0-100) | 0(0-2) | 12(0-70) | 50(25-105) |

The tests were done at the 0.05 level of significance.

Lung metastasis in TE-treated mice<PBS-treated mice (Balb/cByJ), P=0.0003.

Lung metastasis in TE-treated mice>PBS-treated mice (SCID), P=0.0005.

Lung metastasis in TE-treated Balb/cByJ<TE-treated SCID, P=0.0003

Lung metastasis in PBS-treated Balb/cByJ<TE-treated SCID, P=0.10.

Results: The results show no splenomegaly and significant loss of TE-efficacy in SCID mice (Table 11). TE was not able to reduce the numbers of lung colonies in SCID mice.

These findings support an immune-mediated therapeutic mechanism involving T and or B cells in TE-mediated antimetastatic activity.

Example 16

TE-Mediated Inhibition of Metastasis is not Compromised by B-Cell Depletion

Purpose: Since antimetastatic activity of TE is completely lost in SCID mice, we wanted to find out which cell population (T and or B) might be responsible for TE efficacy.

Procedure: We have used a B cell antibody (anti mouse CD20) to deplete mature B cell population in vivo. A lung colonization experiment was performed in B cell depleted as well as B cell intact mice using appropriate isotype control.

TABLE 12

TE-mediated inhibition of metastasis is not Compromised by B-cell Depletion

|  | Balb/cByJ Lung metastasis | | Balb/cByJ Isotype treated Lung metastasis | | Balb/cByJ B cell antibody treated Lung metastasis | |
|---|---|---|---|---|---|---|
|  | Control | TE-treated | Control | TE-treated | Control | TE-treated |
| No. of animals | 9 | 5 | 10 | 12 | 10 | 12 |
| Average lung tumor colonies (Mean ± SE) | 90.7 ± 17.1 | 1.0 ± 0.6<br>p = 0.01 | 57.2 ± 10.8 | 1.25 ± 0.4<br>p = 0.0007 | 64.4 ± 10.5 | 0.3 ± 0.1<br>p = 0.0006 |
| Median no. and range of tumor colonies | 85(20-174) | 1(0-3) | 48(24-133) | 1(0-4) | 64(15-120) | 0(0-1) |

Results: Our studies show no loss of FI efficacy in B cell depleted mice (Table 12). These observations suggest that TE efficacy is not dependent on B cells and coupled with the SCID data, implicate a T lymphocyte in the therapeutic mechanism.

Example 17

The Effect of High and Low Molecular Weight Fraction of TE on Cell Proliferation and Lung Colonization To begin to identify the active compound of TE, we compared the antiproliferative activity of high and low m.w. subfractions of TE.

Isolation of high and low molecular weight fraction of Taro extract and effect on cell proliferation: Stock TE was centrifuged through Amicon Ultra 10 K (10,000) Nominal Molecular Weight Limit (NMWL) devices, at 4000 g for 45 min at 25° C. The lower fraction (low molecular weight fraction) was used for the in vitro and in vivo studies without further treatment. The upper fraction (high molecular weight fraction) was filler sterilized using a 0.2 μm filter and was used for the in vitro and in vivo studies.

In Vitro Studies

Procedure: 66.1 cells were seeded at $2.5 \times 10^5$ cells/well/1.0 ml media in 24 well plate. PBS or low molecular weight fraction of TE was added as indicated. 48 hours later, cell number was determined (FIG. 10) (Kundu, N., Zhang, S. and Fulton, A. M. Sublethal oxidative stress inhibits tumor cell adhesion and enhances experimental metastasis of murine mammary carcinoma. Clin. Exp. Metastasis. 13:16-22, 1995).

Results: The results show little inhibition (not significant) of cell number in presence of the low m.w. fraction of TE.

P values are: Control vs. low mol wt. (25 ul<0.07; 12.5 ul<0.22; 6.25<0.25).

Procedure: 66.1 cells were seeded at $1.0 \times 10^5$ cells/well/1.0 ml media in 24 well plate. PBS or stock or high molecular weight fraction of TE was added as indicated. 48 hours later cell growth was assessed by MTT assay (FIG. 11) (Kundu, N., Smyth, M. J., Samsel, L. and Fulton, A. M. Cyclooxygenase inhibitors block cell growth, increase ceramide and inhibit cell cycle. Breast Cancer Research and Treatment 76:57-64, 2002).

Results: The results show significant inhibition of cell number in the presence of TE Stock or high m.w. fraction of TE at all concentrations compared to PBS. P values are: Control vs. stock (25 ul<0.0005), Control vs. high mol wt. (25 ul<0.0003; 12.5 ul<0.001; 6.25<0.004), The low m.w. fraction had no effect on cell number. The inhibitory effect of TE on cell growth resides chiefly in the high m.w. fraction derived from TE.

In Vivo Studies

Purpose: The high m.w. fraction of TE showed anti-proliferative activity. To determine if anti-metastatic activity of TE is also in the same fraction, we compared the effect of stock TE, high m.w. fraction of TE and low m.w. fraction of TE on lung colonization.

Procedure: Since high molecular weight compounds were concentrated in the upper fraction (protein concentration is twice the stock), 100 μl high molecular weight fraction or 200 μl of PBS (control) or 200 μl TE stock or 200 μl low molecular weight fraction of TE was injected per syngeneic Balb/cByJ female mouse per day i.p. for 4 days. On day 4, $2 \times 10^5$ line 66.1 tumor cells were injected into the lateral tail vein. The PBS or TE treatments were continued i.p daily for an additional 6 days. On day 19 post tumor cell injection, mice were euthanized and surface lung tumor colonies were counted and the presence of heart metastases were noted (Table 13) (Kundu, N., Beaty, T. L., Jackson, M. J. and Fulton, A. M. Antimetastatic and antitumor activities of Interleukin 10 in a murine model of breast cancer. J. Natl. Cancer Inst. 88: 536-541, 1996; Ma, X., Kundu, N., Rifat, S., Walser T. and Fulton, A. M. Prostaglandin E receptor EP4 antagonism inhibits breast cancer metastasis. Cancer Res. 66:2923-2927, 2006).

TABLE 13

Effect of high and low molecular weight TE fractions on lung colonization

|  | Control | Stock TE | TE-high m.w. fraction | TE-low m.w. fraction |
|---|---|---|---|---|
| No. of animals | 7 | 10 | 10 | 8 |
| Average lung tumor colonies(Mean ± SE) | 63 ± 16.53 | 1.0 ± 0.39 p = 0.004 | 5.4 ± 1.11 p = 0.004 | 113.88 ± 27.54 p = 0.40 |
| Median no. and range of tumor colonies | 55.5 (20-131) | 0.5 (0-3) | 4.5 (2-14) | 95(35-212) |
| No. of animals with heart metastasis | 3/7 | 2/10 | 0/10 | 4/8 |

Results: The results confirm our previous observation that stock TE significantly inhibits the ability of tumor cells to colonize the lungs compared to the control. Similarly, significant inhibitory effect of high m.w. fraction of TE on lung metastasis was also seen. This anti-metastatic effect of TE is completely absent in low molecular weight fraction. With regard to tumor colonies in the heart, 3/7 control animals developed heart metastases, 2/10 and 0/10 mice treated with stock or high molecular weight fraction, respectively developed heart metastases and 4/8 mice treated with low molecular weight fraction developed heart metastases.

Example 18

Fractions Profile From Size Exclusion Chromatography Column (SEC)

Purpose: TE efficacy is in the high m.w. fraction and likely from the protein components. We established a protein purification scheme by which the antimetastatic activity can be purified to near homogeneity.

Procedure: Preparative size exclusion chromatography (SEC) was performed on a Biosuite 250, 13μ, 21.5×300 mm column (Waters Corp., Milford. Mass.) using Dulbecco's phosphate buffered saline with calcium and magnesium, at a flow rate of 2 ml/min. 0.5 min. fractions were collected and tubes were pooled based on UV absorbance at 220 nm.

Results: We obtained 10 fractions from Stock TE (FIG. 12). All 10 fractions were tested for antiproliferative activity n vitro using 66.1 tumor cell line.

Only fraction 1, approximately 30 kD from SEC (calibrated using globular proteins), showed modest antiproliferative activity.

Example 19

Effect of Fraction 1 on Lung Colonization

Purpose: Since fraction 1 showed some antiproliferative activity, we examined the effect of fraction 1 on lung colonizing ability of 66.1 tumor cell line in comparison to unfractionated TE or PBS (Table 14).

TABLE 14

Effect of Fraction 1 on Lung colonization

|  | Balb/cByJ mice Lung metastasis | | |
|---|---|---|---|
|  | Control | TE-treated | Fraction 1-treated |
| No. of animals | 9 | 5 | 5 |
| Average lung tumor Colonies (Mean ± SE) | 90.7 ± 17.1 | 1.0 ± 0.6 p = 0.01 | 3.8 ± 1.9 p = 0.01 |
| Median no. and range of tumor colonies | 85(20-174) | 1(0-3) | 3(0-10) |

Protein concentration for this experiment:
TE stock: 400 μg/day/mouse
Fraction 1: 20 μg/day/mouse Results: In spite of the modest effects on proliferation, fraction 1 contains potent antimetastatic activity comparable to stock TE (Table 14). From the elution profile, the antimetastatic activity appears to be separated from most other proteins and likely with excellent recovery of the activity Example 20

Sub Fraction Profile From Ion-Exchange Chromatography

Purpose and procedure: Fraction 1 containing the antimetastatic activity was further purified by ionic exchange column (Poros HQ/20, anion exchange).

Preparative Anion Exchange Chromatography was carried out on an HQ/20, 10×100 mm column (Applied Biosystems, Inc., Foster City, Calif.), using a 30 minute gradient of 0-30% B at a flow rate of 5 ml/min.: Buffer A×50 mM Tris, pH 8.0, Buffer B=50 mM Tris pH 8+1.0 M NaCl. 0.5 min. fractions were collected and tubes were pooled based on UV absorbance at 220 nm. The pooled samples were concentrated using Centricon Plus 70 10 K Nominal Molecular Weight Limit (NMWL) devices (Millipore) and buffer exchange was done using Zeba Desalt Spin Columns, Pierce Protein Research Product (Thermo Scientific).

Four sub fractions obtained from this step (FIG. 13) were assessed in the lung colonization assay using 66.1 cell line and compared with the antimetastatic activity of stock TE (Table 15).

TABLE 15

Effects of sub fractions 1.1, 1.2, 1.3 and 1.4 on lung colonization

|  | Control | Stock TE | Sub fraction 1.1 | Sub fraction 1.2 | Sub fraction 1.3 | Sub fraction 1.4 |
|---|---|---|---|---|---|---|
| No of animals | 8 | 5 | 4 | 4 | 5 | 4 |
| Average lung Tumor colonies (Mean ± SE) | 46.0 ± 29.2 | 0 ± 0 p < 0.0001 | 0.3 ± 0.4 p < 0.0001 | 0.8 ± 0.4 p < 0.0001 | 16.8 ± 5.8 p = 0.06 | 42.5 ± 13.9 p = 0.85 |
| Median no. and range of tumor colonies | 51(0-90) | 0(0-0) | 0(0-1) | 1(0-1) | 16(9-27) | 44.5(21-60) |

Results: The majority of the antimetastatic activity was recovered from the first and the second sub fraction peaks. Activity gradually decreases in the third peak and is almost lost in the fourth peak.

Example 21

Subfraction 1.1 Shows Significant Antimetastatic Activity But no Effect on Any Organ Purpose: Once it was determined that subfraction 1.1 has antimetastatic activity, we wanted to find out if subfraction 1.1 has potential toxicity and we compared the effect of PBS, stock TE and sub fraction 1.1 on body and organ weight.

Procedure: Normal syngeneic Balb/cByJ female mice were treated i.p. with PBS, 400 µg TE or 20 µg sub fraction 1.1 for 4 days. On day 5, mice were euthanized and organ wet weight was determined. Body weight was assessed on day 1 and day 5 and the difference recorded as body weight gain.

TABLE 16

Effects of stock and purified TE treatment on body and organ weight

|  | Body weight gain (mg) | Spleen (mg) | Liver (mg) | Kidney (mg) | Heart (mg) | Lung (mg) |
|---|---|---|---|---|---|---|
| PBS (n = 3) | 73 ± 10 | 94 ± 6 | 1000 ± 45 | 293 ± 7 | 137 ± 9 | 158 ± 4 |
| Sub fraction 1.1 (n = 3) | 89 ± 17 | 121 ± 9 | 1159 ± 67 | 293 ± 10 | 134 ± 5 | 163 ± 12 |
| Stock TE (n = 3) | 78 ± 17 | 183 ± 12 p = 0.006 | 1553 ± 116 p = 0.03 | 345 ± 22 | 144 ± 10 | 206 ± 16 |

Values are: Mean ± SE

Results: The gross appearance of whole animal or individual organs was not different in control versus TE-treated mice except for the spleen and liver weights. Spleen and liver weight were significantly increased in stock TE treated but not in sub fraction 1.1 treated group. Body weight gain was also not significantly different in either TE-treated versus control mice. The reported P values are from the Student's t-test.

Example 22

Fraction Profile From Reversed Phase Liquid Chromatography (RPLC)

Purpose: We wanted to find out the purity of the antimetastatic activity in each sub fraction.

Procedure: Each sub fraction of the anion exchange column was analyzed by reversed phase chromatography (Jupiter C5, 300 A) on HPLC (FIGS. 14-17).

Analytical RPLC was done using a Jupiter C5 300 Å column (Phenomenex, Torrance, Calif.), employing a 40 minute gradient of 1-100% B at 1 ml/min. Buffer A=0.1% trifluoroacetic acid (TFA) in water, Buffer B=0.1% TFA, in water:acetonitrile (20:80), with UV detection at 215 nm. All chromatography was done on Beckman Coulter HPLC systems with System Gold V8 or 32 Karat software packages.

Results: Only one protein peak (at 23.4 minute) was eluted from sub fraction 1.1 (FIG. 14), suggesting that the fraction containing antimetastatic activity is in almost pure form. When other sub fractions were analysed on RPLC multiple peaks including sub fraction 1.1 (at 23.4 minute), as a contamination in decreasing order were eluted (FIGS. 15-17). This probably explains why sub fraction 1.2 also shows significant antimetastatic activity but not sub fraction 1.4. In sub fraction 1.2, there is significant amount of contamination with sub fraction 1.1 but in sub fraction 1.4 much less contamination with sub fraction 1.1 is seen. Taken together, we have established a simple two-step purification scheme by which the taro-derived antimetastatic activity can be easily purified with high yield. We estimate that we could obtain about 10 mg active protein from 100 g taro.

Example 23

Protein Sequencing from Sub Fraction 1.1

Purpose: Knowing the results that sub fraction 1.1 contains the major antimetastatic activity, we wanted to find out the sequence of the protein/proteins in the sub fraction 1.1 and also if the sequence matches to any know protein, Procedure: Sub fraction 1.1 was collected in five tubes (sub fraction 1.1.1, 1.1.2, 1.1.3, 1.1.4, 1.1.5). Aliquot from each tube was pooled and N-terminal sequencing was performed.

Results: The results indicate 2 N-termini, either from different proteins, or from the same protein where a partial proteolytic cleavage has occurred.

From N-terminus→C-terminus, each cycle has 2 amino acid signals.

N/L-G/I-T/P-N/F-T/Y-N/L-S/L-G/L-Q/F-S/T-G/L-N/Q-T/V-D/L-D/Y-G/X-H/D-K/X-R/X

To find out if these two proteins elute in different time points or at the same time, sample from each tube was analysed using Symmetry C4 column and they all looked similar. There is a major peak and a smaller unresolved peak eluting just after the main peak (FIG. 18-23).

The major peak was sequenced and the results representing the data from 16 cycles.

```
                                        (SEQ ID NO: 5)
    IEX pool of 1.1.1-1.1.5-C4 Frac-19->
    L-G-T-N-Y-L-L-S-G-Q-T-L-N-T-D-G
```

After subtracting this sequence from the first sequence we obtained the sequence for the smaller peak and that is:

```
                                        (SEQ ID NO: 6)
    From N-terminus-> C-terminus:
    N-I-P-F-T-N-N-L L-F-S-G-Q-V-L
```

Example 24

Identification of the Protein Fragments

The active component(s) consists of two protein fragments of 12 and 13 kD —When the active component(s) was analyzed from subfraction 1.1 by SDS-PAGE, two protein bands were seen with sizes of approximately 12 and 13 kD. Since the native size of the active component(s) determined by the sizing column is around 30 kD, the active component(s) likely consist of the two fragments seen in SDS-PAGE at a 1:1 ratio. This hypothesis is further supported by the analyses of the N-terminal sequences of the active components. When the pooled active components were subjected to automated Edman degradation, two major phenylthiohydantoin (PTH)-amino acid signals in each cycle were observed at nearly an equimolar ratio. Taken together, the active component(s) appears to be a 25 kD protein that contains two subunits with sizes of 12 and 13 kD.

In order to obtain the N-terminal sequences of the two fragments, the active component(s) pooled from Poros HQ/20 column were purified further by rpHPLC. Two partially resolved peaks were obtained. The amino acid sequence for Peak-I was determined to be LGTNYLLS-GQTLNTDGHLKNGDFD (SEQ ID NO:1) and the sequence of the second peak in the fractions was deduced to be NIPFINNLLFSGQVLYGDGRLTAKNH (SEQ ID NO:2) by subtracting the sequence obtained for Peak-I from the data obtained previously with both sequences. A BLAST similarity search of the sequence data against the nr database reveals that the active component(s) is highly related to three taro proteins, including the taro 12 kD storage protein (accession number BAA03722), tarin (accession number CAA53717), and the taro lectin (accession number ABQ32294). The 24 N-terminal amino acid sequence of the protein in Peak-I is identical to both taro lectin and tarin which appear to be distinct gene products with identical N-terminal amino acid sequences that significantly diverge after amino acid 142 (FIG. 30). The N-terminal sequence of the Peak-I protein is also nearly identical to a third taro protein, namely 12 kD storage protein with differences in only two amino acid residues (FIG. 30). Interestingly, the 26 amino acid sequence identified in the Peak-II protein is identical to that of the 12 kD storage protein. The N-terminal sequence of the Peak-II protein is also highly related to tarin with 72% identity (18 out of 25 amino acid residues) and taro lectin with 96% identity (24 out 25 amino acid residues). Examination of the original sequence data from the ion-exchange fractions showed that the yield of PTH-glutamic acid in cycles thirteen and fifteen was near background level indicating that the N-terminal polypeptide chain (residues 28-143) of 12 kD storage protein was not present or was below the level of detection. The three taro proteins appear to undergo an identical two-step maturation process to generate mature forms with two fragments: the signal peptides are removed by a cleavage at SAVA-LGTN followed by a second proteolytic cleavage at FR-NIP to generate two fragments (FIG. 31). Since the active component(s) contains two fragments with their N-terminal sequences matching to the two cleavage sites, respectively, the active component(s) resembles the taro proteins in terms of the maturation process as summarized (FIG. 31). All three proteins (12 kD storage protein, tarin and taro lectin) contain a carbohydrate binding domain. Therefore, our proposed active compound may also contain this domain

Example 25

Major vs. Minor Protein Ratio Measurement

Purpose: Since under these conditions two proteins were co-purified, we wanted to measure the ratio of these two proteins.

The proportion of each protein to one another was estimated from data obtained by automated Edman degradation (Table 17) and comparing the initial yields of each protein's unique N-terminal amino acid. In the taro sample the yield of Asn was 54.3 pm from protein 1 and of Leu was 66.3 pm from protein 2 respectively. These data indicate that the two proteins are present at 0.8:1 ratio in the final purification step.

TABLE 17

PTH-Amino Acid Yields from IEX Fractions

| Cycle | Called Residues | Yield (pmoles) |
|---|---|---|
| 1 | N | 54.3 |
|   | L | 66.3 |
| 2 | G | 53.1 |
|   | I | 58.7 |
| 3 | T | 54.9 |
|   | P | 50.6 |
| 4 | N | 41.5 |
|   | F | 49.3 |

Example 26

Antimetastatic Activity in Malanga and Yautia

We wanted to find out if this antimetastatic activity could be the unique property of Taro only or if it is present in other plants of similar kind. We tested antimetastatic potential from two different plants Malanga Blanca (*Xanthosoma sagittifolium*) and Yautia (*Xanthosoma sagittifolium*) which are closely related to Taro but different species.

We prepared stock extracts from Malanga Blanca (ME) and Yautia (YE) following the same protocol as Taro extract (TE). Antimetastatic activity was determined from both extracts following the previous protocol.

Example 27

Effects of TE, ME and YE on Lung Colonization

Procedure: We examined the effect of TE, ME and YE on lung colonizing ability of highly metastatic lines 66.1. PBS or TE (400 µg), ME (200 µg) or YE (200 µg) was injected i.p. on days 1-4 into syngeneic Balb/cByJ female mice. On day 4, $1 \times 10^5$ line 66.1 tumor cells were injected into the lateral tail vein. Treatment with PBS, TE, ME or YE continued for an additional 6 days. On day 18 post tumor cell injection, mice were euthanized and surface lung tumor colonies were counted (Table 18).

TABLE 18

Effects of TE, ME and YE on Lung Colonization

|  | Control | Stock TE | Stock ME | Stock YE |
|---|---|---|---|---|
| No of animals | 8 | 5 | 5 | 5 |
| Average lung tumor | 46.0 ± 29.21 | 0 ± 0 | 1.2 ± 1.6 | 9.8 ± 5.3 |

TABLE 18-continued

Effects of TE, ME and YE on Lung Colonization

|  | Control | Stock TE | Stock ME | Stock YE |
|---|---|---|---|---|
| colonies (Mean ± SE) |  | $p < 0.0001$ | $p < 0.0001$ | $p = 0.02$ |
| Median no of metastasis | 51(0-90) | 0(0-0) | 0(0-4) | 12(1-16) |

Results: Table 18 summarize the effect of TE, ME and YE on lung colonization by 66.1 cell lines, respectively. The results show each stock profoundly inhibits the ability of tumor cells to colonize the lungs. These results also indicate that the antimetastatic activity is not only present in Taro but also present (variable potency) in other closely related plants of different species.

Example 28

Fractions Profile From Size Exclusion Chromatography Column

Purpose: Since all three extracts show similar antimetastatic activity, we wanted to find out if this could be due to similar compound present in the extracts derived from each plant.
Procedure: We purified antimetastatic activity from ME and YE using size exclusion chromatography as we have done from TE. This time results are presented in data point format (FIGS. 24-26).
Results: The results show the presence of a similar (fraction 1) peak in ME and YE as is seen in TE and which showed the antimetastatic activity in TE. It may be that ME and YE contain the same protein/proteins as in TE and are responsible for the antimetastatic activity of these plants.

Example 29

Fraction Profile From Reversed Phase Liquid Chromatography

Purpose: Since stock TE, ME and YE showed similar fraction 1 in size exclusion chromatography, we wanted to reconfirm the presence of similar compound in these extracts.
Procedure: We have analyzed the stocks using reversed phase chromatography (Jupiter C5, 300 A) on HPLC (FIGS. 27-29).
Results: These results again confirm the presence of similar compound/compounds in each stock which elutes in 24-24.2 minutes. It also shows that the amount is more in TE and ME compared to YE. This may explain why YE is slightly less potent compared to TE and ME.

Example 30

Protein Sequencing of ME from Sub Fraction 1.1

Purpose: When size exclusion and reversed phase chromatography showed similar protein/proteins in the fraction 1 of ME as seen in TE, we wanted to find out the amino acid sequence of the protein/proteins.
Procedure: Fraction 1 of ME from size exclusion chromatography was analyzed using anion exchange chromatography. The sub fraction 1.1 of ME (similar to the sub fraction 1.1 of TE) from anion exchange chromatography was sequenced.
Results: The results showed identical sequence to the previous sample (TE) and the two proteins in roughly equal proportions based on the yield of the two amino acids in cycle one.
From N-terminus→C-terminus, each cycle has 2 amino acid signals and these signals are very similar to the signals which were seen in TE-sub fraction 1.1.

```
Malanga IEX T9-> L/N-G/I-T/P-N/F
```

So, the two sequences are:

```
                                              (SEQ ID NO: 3)
            L-G-T-N
            and (SEQ ID NO: 4)
            N-I-P-F
```

Conclusion: The plants which contain this compound may show antimetastatic property.
Statistical Analysis
Data were summarized using the following descriptive statistics, means and standard errors, medians and ranges. Depending on the data distribution, the student's t-test, or its non parametric alternative, the Wilcoxon test, were used to compare distribution of metastases between treatment groups. All tests were exact, and done at the two-sided 0.05 level of significance.

SEQUENCE LISTING

```
<160> NUMBER OF SEQ ID NOS: 19

<210> SEQ ID NO 1
<211> LENGTH: 24
<212> TYPE: PRT
<213> ORGANISM: Colocasia esculenta

<400> SEQUENCE: 1

Leu Gly Thr Asn Tyr Leu Leu Ser Gly Gln Thr Leu Asn Thr Asp Gly
1               5                   10                  15

His Leu Lys Asn Gly Asp Phe Asp
            20

<210> SEQ ID NO 2
<211> LENGTH: 26
<212> TYPE: PRT
```

-continued

```
<213> ORGANISM: Colocasia esculenta

<400> SEQUENCE: 2

Asn Ile Pro Phe Thr Asn Asn Leu Leu Phe Ser Gly Gln Val Leu Tyr
1               5                   10                  15

Gly Asp Gly Arg Leu Thr Ala Lys Asn His
            20                  25

<210> SEQ ID NO 3
<211> LENGTH: 4
<212> TYPE: PRT
<213> ORGANISM: Xanthosoma sagittifolium

<400> SEQUENCE: 3

Leu Gly Thr Asn
1

<210> SEQ ID NO 4
<211> LENGTH: 4
<212> TYPE: PRT
<213> ORGANISM: Xanthosoma sagittifolium

<400> SEQUENCE: 4

Asn Ile Pro Phe
1

<210> SEQ ID NO 5
<211> LENGTH: 16
<212> TYPE: PRT
<213> ORGANISM: Colocasia esculenta

<400> SEQUENCE: 5

Leu Gly Thr Asn Tyr Leu Leu Ser Gly Gln Thr Leu Asn Thr Asp Gly
1               5                   10                  15

<210> SEQ ID NO 6
<211> LENGTH: 15
<212> TYPE: PRT
<213> ORGANISM: Colocasia esculenta

<400> SEQUENCE: 6

Asn Ile Pro Phe Thr Asn Asn Leu Leu Phe Ser Gly Gln Val Leu
1               5                   10                  15

<210> SEQ ID NO 7
<211> LENGTH: 253
<212> TYPE: PRT
<213> ORGANISM: Colocasia esculenta

<400> SEQUENCE: 7

Met Ala Lys Leu Leu Leu Phe Leu Leu Pro Ala Ile Leu Gly Leu Leu
1               5                   10                  15

Ile Pro Arg Ser Ala Val Ala Leu Gly Thr Asn Tyr Leu Leu Ser Gly
            20                  25                  30

Gln Thr Leu Asn Thr Asp Gly His Leu Lys Asn Gly Asp Phe Asp Leu
        35                  40                  45

Val Met Gln Asn Asp Cys Asn Leu Val Leu Tyr Asn Gly Asn Trp Gln
    50                  55                  60

Ser Asn Thr Ala Asn Asn Gly Arg Asp Cys Lys Leu Thr Leu Thr Asp
65                  70                  75                  80

Tyr Gly Asp Leu Val Ile Lys Asn Arg Asp Gly Ser Thr Val Trp Arg
                85                  90                  95
```

```
Ser Arg Ala Lys Ser Val Lys Gly Asn Tyr Ala Ala Val Leu His Pro
                100                 105                 110

Asp Gly Arg Leu Val Val Phe Gly Pro Ser Val Phe Lys Asn Asp Pro
            115                 120                 125

Trp Val Pro Gly Leu Asn Ser Leu Ala Phe Arg Asn Ile Pro Ser Pro
130                 135                 140

Thr Thr Cys Ser Ser Pro Gln Val Leu Tyr Gly Asp Gly Arg Leu Thr
145                 150                 155                 160

Ala Lys Asn His Gln Leu Gly His Ala Gly Arg Leu Gln Pro Gly Pro
                165                 170                 175

Ile Arg Leu Val Lys Tyr Gly Trp Gln Ser Asn Thr His Gly Asn Gly
            180                 185                 190

Glu His Cys Phe Leu Arg Leu Asn His Lys Gly Glu Leu Ile Ile Arg
        195                 200                 205

Thr Thr Thr Ser Arg Pro Ser Gly Ala Ala Val Pro Ala Pro Ser Arg
210                 215                 220

Val Thr Thr Phe Ser Thr Ser Arg His Val Arg Arg Ala Leu Arg Pro
225                 230                 235                 240

Ala Ile Trp Arg Pro Ala Arg Ser Ala Pro Leu Leu Thr
                245                 250

<210> SEQ ID NO 8
<211> LENGTH: 253
<212> TYPE: PRT
<213> ORGANISM: Colocasia esculenta

<400> SEQUENCE: 8

Met Ala Lys Leu Leu Phe Leu Leu Pro Ala Ile Leu Gly Leu Leu
1               5                   10                  15

Ile Pro Arg Ser Ala Val Ala Leu Gly Thr Asn Tyr Leu Leu Ser Gly
            20                  25                  30

Gln Thr Leu Asn Thr Asp Gly His Leu Lys Asn Gly Asp Phe Asp Leu
        35                  40                  45

Val Met Gln Asn Asp Cys Asn Leu Val Leu Tyr Asn Gly Asn Trp Gln
50                  55                  60

Ser Asn Thr Ala Asn Asn Gly Arg Asp Cys Lys Leu Thr Leu Thr Asp
65                  70                  75                  80

Tyr Gly Asp Leu Val Ile Lys Asn Arg Asp Gly Ser Thr Val Trp Arg
                85                  90                  95

Ser Arg Ala Lys Ser Val Lys Gly Asn Tyr Ala Ala Val Leu His Pro
                100                 105                 110

Asp Gly Arg Leu Val Val Phe Gly Pro Ser Val Phe Lys Asn Asp Pro
            115                 120                 125

Trp Val Pro Gly Leu Asn Ser Leu Ala Phe Arg Asn Ile Pro Ser Pro
130                 135                 140

Thr Thr Cys Ser Ser Pro Gln Val Leu Tyr Gly Asp Gly Arg Leu Thr
145                 150                 155                 160

Ala Lys Asn His Gln Leu Gly His Ala Gly Arg Leu Gln Pro Gly Pro
                165                 170                 175

Ile Arg Leu Val Lys Tyr Gly Trp Gln Ser Asn Thr His Gly Asn Gly
            180                 185                 190

Glu His Cys Phe Leu Arg Leu Asn His Lys Gly Glu Leu Ile Ile Arg
        195                 200                 205

Thr Thr Thr Ser Arg Pro Ser Gly Ala Ala Val Pro Ala Pro Ser Arg
```

```
                210                 215                 220
Val Thr Thr Phe Ser Thr Ser Arg His Val Arg Arg Ala Leu Arg Pro
225                 230                 235                 240

Ala Ile Trp Arg Pro Ala Arg Ser Ala Pro Leu Leu Thr
                245                 250
```

<210> SEQ ID NO 9
<211> LENGTH: 268
<212> TYPE: PRT
<213> ORGANISM: Colocasia esculenta

<400> SEQUENCE: 9

```
Arg His Ile Pro His Gly Gln Ala Ser Pro Leu Pro Pro Gly His
1               5                   10                  15

Pro Arg Pro Arg Ser Trp Ser Ala Val Ala Leu Gly Thr Asn Tyr
                20                  25                  30

Leu Leu Ser Gly Gln Thr Leu Glu Thr Glu Gly His Leu Lys Asn Gly
            35                  40                  45

Asp Phe Asp Leu Val Met Gln Asp Asp Cys Asn Leu Val Leu Tyr Asn
        50                  55                  60

Gly Asn Trp Gln Ser Asn Thr Ala Asn Lys Gly Arg Asp Cys Lys Leu
65                  70                  75                  80

Thr Leu Thr Asp His Gly Glu Leu Val Ile Asn Asn Gly Asp Gly Ser
                85                  90                  95

Thr Val Trp Arg Ser Gly Ala Gln Ser Val Lys Gly Asp Tyr Ala Ala
            100                 105                 110

Val Val His Pro Glu Gly Arg Leu Val Val Phe Ser Pro Ser Val Phe
        115                 120                 125

Lys Ile Asp Pro Ser Val Pro Gly Leu Asn Ser Leu Arg Phe Arg Asn
130                 135                 140

Ile Pro Phe Thr Asn Asn Leu Leu Phe Ser Gly Gln Val Leu Tyr Gly
145                 150                 155                 160

Asp Gly Arg Leu Thr Ala Lys Asn His Gln Leu Val Met Gln Gly Asp
                165                 170                 175

Cys Asn Leu Val Leu Tyr Gly Gly Lys Tyr Gly Trp Gln Ser Asn Thr
            180                 185                 190

His Gly Asn Gly Glu His Cys Phe Leu Arg Leu Asn His Lys Gly Glu
        195                 200                 205

Leu Ile Ile Glu Asp Asp Phe Lys Thr Ile Trp Ser Ser Ser Tyr
210                 215                 220

Ser Ser Lys Gln Gly Asp Tyr Val Leu Ile Leu Arg Asp Asp Gly Val
225                 230                 235                 240

Ala Val Ile Tyr Gly Pro Ala Ile Trp Glu Thr Ser Pro Gln Ala Lys
                245                 250                 255

Glu Lys Met Ile Gly Met Val Thr Ala Gly Lys Leu
            260                 265
```

<210> SEQ ID NO 10
<211> LENGTH: 2
<212> TYPE: PRT
<213> ORGANISM: Colocasia esculenta
<220> FEATURE:
<221> NAME/KEY: misc_feature
<222> LOCATION: (2)..(2)
<223> OTHER INFORMATION: Unspecified number of amino acid residues; SEQ
      ID NOS: 10, 11 and 12 are part of the same peptide

<400> SEQUENCE: 10

Met Xaa
1

<210> SEQ ID NO 11
<211> LENGTH: 11
<212> TYPE: PRT
<213> ORGANISM: Colocasia esculenta
<220> FEATURE:
<221> NAME/KEY: misc_feature
<222> LOCATION: (11)..(11)
<223> OTHER INFORMATION: unspecified number of amino acid residues; SEQ
      ID NOS: 10, 11 and 12 are part of the same peptide

<400> SEQUENCE: 11

Ser Ala Val Ala Leu Gly Thr Asn Tyr Leu Xaa
1               5                   10

<210> SEQ ID NO 12
<211> LENGTH: 9
<212> TYPE: PRT
<213> ORGANISM: Colocasia esculenta
<220> FEATURE:
<221> NAME/KEY: misc_feature
<222> LOCATION: (9)..(9)
<223> OTHER INFORMATION: unspecified number of amino acid residues; SEQ
      ID NOS: 10, 11 and 12 are part of the same peptide

<400> SEQUENCE: 12

Phe Arg Asn Ile Pro Phe Thr Asn Xaa
1               5

<210> SEQ ID NO 13
<211> LENGTH: 2
<212> TYPE: PRT
<213> ORGANISM: Colocasia esculenta
<220> FEATURE:
<221> NAME/KEY: misc_feature
<222> LOCATION: (2)..(2)
<223> OTHER INFORMATION: unspecified number of amino acids; SEQ ID NOS:
      13 and 14 are part of the same peptide

<400> SEQUENCE: 13

Met Xaa
1

<210> SEQ ID NO 14
<211> LENGTH: 4
<212> TYPE: PRT
<213> ORGANISM: Colocasia esculenta

<400> SEQUENCE: 14

Ser Ala Val Ala
1

<210> SEQ ID NO 15
<211> LENGTH: 7
<212> TYPE: PRT
<213> ORGANISM: Colocasia esculenta
<220> FEATURE:
<221> NAME/KEY: misc_feature
<222> LOCATION: (7)..(7)
<223> OTHER INFORMATION: unspecified number of amino acids; SEQ ID NOS:
      15 and 16 are part of the same peptide

<400> SEQUENCE: 15

Leu Gly Thr Asn Tyr Leu Xaa
1               5

```
<210> SEQ ID NO 16
<211> LENGTH: 9
<212> TYPE: PRT
<213> ORGANISM: Colocasia esculenta
<220> FEATURE:
<221> NAME/KEY: misc_feature
<222> LOCATION: (9)..(9)
<223> OTHER INFORMATION: unspecified number of amino acid residues; SEQ
      ID NOS: 15 and 16 are part of the same peptide

<400> SEQUENCE: 16

Phe Arg Asn Ile Pro Phe Thr Asn Xaa
1               5

<210> SEQ ID NO 17
<211> LENGTH: 7
<212> TYPE: PRT
<213> ORGANISM: Colocasia esculenta
<220> FEATURE:
<221> NAME/KEY: misc_feature
<222> LOCATION: (7)..(7)
<223> OTHER INFORMATION: unspecified number of amino acid residues; SEQ
      ID NOS: 17 and 18 are part of the same peptide

<400> SEQUENCE: 17

Leu Gly Thr Asn Tyr Leu Xaa
1               5

<210> SEQ ID NO 18
<211> LENGTH: 3
<212> TYPE: PRT
<213> ORGANISM: Colocasia esculenta
<220> FEATURE:
<221> NAME/KEY: misc_feature
<222> LOCATION: (1)..(1)
<223> OTHER INFORMATION: unspecified number of amino acid residues; SEQ
      ID NOS: 17 and 18 are part of the same peptide

<400> SEQUENCE: 18

Xaa Phe Arg
1

<210> SEQ ID NO 19
<211> LENGTH: 7
<212> TYPE: PRT
<213> ORGANISM: Colocasia esculenta
<220> FEATURE:
<221> NAME/KEY: misc_feature
<222> LOCATION: (7)..(7)
<223> OTHER INFORMATION: unspecified number of amino acid residues

<400> SEQUENCE: 19

Asn Ile Pro Phe Thr Asn Xaa
1               5
```

What is claimed is:

1. A method of treating breast cancer by inhibiting metastasis in a subject in need thereof, comprising administering to the subject a composition comprising a therapeutically effective amount of an isolated polypeptide from Taro (*Colocasia esculenta*), wherein the isolated polypeptide comprises SEQ ID NO:1 and SEQ ID NO:2, wherein the isolated polypeptide has an approximate molecular weight of 30 KD based on size exclusion chromatography.

2. The method of claim 1, wherein the isolated polypeptide is administered with a carrier molecule.

3. The method of claim 1, wherein the subject is a human.

4. The method of claim 1, wherein the composition is administered parenterally.

* * * * *